United States Patent
Fischer et al.

(10) Patent No.: US 8,039,014 B2
(45) Date of Patent: Oct. 18, 2011

(54) 3'-ALKOXYSPIROCYCLOPENTYL-SUBSTITUTED TETRAMIC AND TETRONIC ACIDS

(75) Inventors: Reiner Fischer, Monheim (DE); Stefan Lehr, Liederbach (DE); Dieter Feucht, Eschborn (DE); Eva-Maria Franken, Leichlingen (DE); Olga Malsam, Rösrath (DE); Guido Bojack, Wiesbaden (DE); Christian Arnold, Langenfeld (DE); Martin Jeffrey Hills, Idstein (DE); Heinz Kehne, Hofheim (DE); Christopher Hugh Rosinger, Hofheim (DE); Jan Dittgen, Frankfurt (DE)

(73) Assignee: Bayer Cropscience AG, Monheim (DE)

( * ) Notice: Subject to any disclaimer, the term of this patent is extended or adjusted under 35 U.S.C. 154(b) by 209 days.

(21) Appl. No.: 12/097,046

(22) PCT Filed: Dec. 11, 2006

(86) PCT No.: PCT/EP2006/011911
§ 371 (c)(1),
(2), (4) Date: Nov. 3, 2008

(87) PCT Pub. No.: WO2007/073856
PCT Pub. Date: Jul. 5, 2007

(65) Prior Publication Data
US 2010/0004127 A1 Jan. 7, 2010

(30) Foreign Application Priority Data
Dec. 15, 2005 (DE) .......... 10 2005 059 891

(51) Int. Cl.
C07D 207/46 (2006.01)
C07D 491/10 (2006.01)
C07D 307/94 (2006.01)
A01P 13/00 (2006.01)

(52) U.S. Cl. ......... 424/405; 504/283; 548/408; 549/331
(58) Field of Classification Search ................. 548/408; 549/331
See application file for complete search history.

(56) References Cited

U.S. PATENT DOCUMENTS

| | | | |
|---|---|---|---|
| 2,842,476 A | 7/1958 | Schreiber | |
| 4,021,224 A | 5/1977 | Pallos et al. | |
| 4,186,130 A | 1/1980 | Teach | |
| 4,623,727 A | 11/1986 | Huebele | |
| 4,639,266 A | 1/1987 | Heubach et al. | |
| 4,844,734 A | 7/1989 | Iwasaki et al. | |
| 4,881,966 A | 11/1989 | Nyffeler et al. | |
| 4,888,049 A | 12/1989 | Iwasaki et al. | |
| 4,891,057 A | 1/1990 | Sohn et al. | |
| 4,902,340 A | 2/1990 | Hubele | |
| 5,164,179 A | 11/1992 | Hioki et al. | |
| 5,258,527 A | 11/1993 | Krauskopf et al. | |
| 5,262,383 A | 11/1993 | Fischer et al. | |
| 5,298,501 A | 3/1994 | Cummings | |
| 5,314,863 A | 5/1994 | Loeher et al. | |
| 5,380,852 A | 1/1995 | Schuetze et al. | |
| 5,401,700 A | 3/1995 | Sohn et al. | |
| 5,407,897 A | 4/1995 | Cary et al. | |
| 5,462,912 A | 10/1995 | Hioki et al. | |
| 5,462,913 A | 10/1995 | Fischer et al. | |
| 5,504,057 A | 4/1996 | Fischer et al. | |
| 5,516,750 A | 5/1996 | Willms et al. | |
| 5,538,937 A | 7/1996 | Hasebe et al. | |
| 5,567,671 A | 10/1996 | Fischer et al. | |
| 5,589,469 A | 12/1996 | Fischer et al. | |
| 5,610,122 A | 3/1997 | Fischer et al. | |

(Continued)

FOREIGN PATENT DOCUMENTS

| | | |
|---|---|---|
| DE | 2 218 097 | 11/1972 |
| DE | 2 350 547 | 4/1974 |
| DE | 196 21 522 A1 | 12/1997 |
| EP | 0 036 106 A2 | 2/1981 |
| EP | 0 086 750 A2 | 2/1983 |

(Continued)

OTHER PUBLICATIONS

J. Patrick Parkman. Pest Management Strategic Plan for Beef Cattle in Tennessee and Kentucky. Summary of Workshops held in Jan. 2005 Princeton, KY and Nashville, TN (2005).*

(Continued)

Primary Examiner — Shawquia Young
(74) Attorney, Agent, or Firm — Baker Donelson Bearnan, Caldwell & Berkowitz, PC

(57) ABSTRACT

The invention relates to novel compounds of the formula (I)

(I)

in which
W, X, Y, Z, A, B, D, $Q^1$, $Q^2$ and G are as defined above, to a plurality of processes for their preparation and to their use as pesticides and/or herbicides and/or fungicides and also to selective herbicidal compositions comprising, firstly, the 3'-alkoxyspirocyclopentyl-substituted tetramic and tetronic acids of the formula (I) and, secondly, at least one crop plant compatibility-improving compound, and also to boosting the activity of crop protection compositions comprising active compounds from the class of the 3'-alkoxyspirocyclopentyl-substituted tetramic and tetronic acids of the formula (I) by adding ammonium salts and/or phosphonium salts or by adding ammonium salts and/or phosphonium salts and penetrants, to the corresponding compositions, to processes for their preparation and to their use in crop protection.

23 Claims, No Drawings

U.S. PATENT DOCUMENTS

| | | |
|---|---|---|
| 5,622,917 A | 4/1997 | Fischer et al. |
| 5,700,758 A | 12/1997 | Roesch et al. |
| 5,703,132 A | 12/1997 | Sagenmuller et al. |
| 5,705,476 A | 1/1998 | Hoffarth |
| 5,739,079 A | 4/1998 | Holdgruen et al. |
| 5,830,825 A | 11/1998 | Fischer et al. |
| 5,830,826 A | 11/1998 | Fischer et al. |
| 5,981,567 A | 11/1999 | Fischer et al. |
| 6,114,374 A | 9/2000 | Lieb et al. |
| 6,140,358 A | 10/2000 | Lieb et al. |
| 6,200,932 B1 | 3/2001 | Fischer et al. |
| 6,235,680 B1 | 5/2001 | Ziemer et al. |
| 6,251,827 B1 | 6/2001 | Ziemer et al. |
| 6,251,830 B1 | 6/2001 | Fischer et al. |
| 6,288,102 B1 | 9/2001 | Hagemann et al. |
| 6,316,486 B1 | 11/2001 | Lieb et al. |
| 6,358,887 B1 | 3/2002 | Fisher et al. |
| 6,417,370 B1 | 7/2002 | Lieb et al. |
| 6,451,843 B1 | 9/2002 | Lieb et al. |
| 6,458,965 B1 | 10/2002 | Lieb et al. |
| 6,472,419 B1 | 10/2002 | Fischer et al. |
| 6,511,940 B1 | 1/2003 | Ziemer et al. |
| 6,511,942 B1 | 1/2003 | Lieb et al. |
| 6,589,976 B1 | 7/2003 | Fischer et al. |
| 6,602,823 B1 | 8/2003 | Roechling et al. |
| 6,608,211 B1 | 8/2003 | Hagemann et al. |
| 6,645,914 B1 | 11/2003 | Woznica et al. |
| 6,861,391 B1 | 3/2005 | Fischer et al. |
| 6,894,005 B1 | 5/2005 | Maetzke et al. |
| 7,638,547 B2 | 12/2009 | Himmler et al. |
| 7,727,933 B2 | 6/2010 | Fischer et al. |
| 7,754,654 B2 | 7/2010 | Fischer et al. |
| 2002/0188136 A1* | 12/2002 | Lieb et al. ............ 548/368.4 |
| 2003/0216260 A1 | 11/2003 | Ruther et al. |
| 2003/0224939 A1 | 12/2003 | Miles |
| 2005/0009880 A1 | 1/2005 | Cottrell et al. |
| 2005/0054535 A1 | 3/2005 | Fischer et al. |
| 2005/0096386 A1 | 5/2005 | Cottrell et al. |
| 2006/0160847 A1 | 7/2006 | Fischer et al. |
| 2006/0166829 A1 | 7/2006 | Fischer et al. |
| 2007/0015664 A1 | 1/2007 | Fischer et al. |
| 2007/0129252 A1 | 6/2007 | Fischer et al. |
| 2007/0225170 A1 | 9/2007 | Fischer et al. |
| 2007/0244007 A1 | 10/2007 | Fischer et al. |
| 2007/0298968 A1 | 12/2007 | Bretschneider et al. |
| 2008/0305955 A1 | 12/2008 | Bretschneider et al. |
| 2009/0029858 A1 | 1/2009 | Fischer et al. |
| 2010/0174084 A1 | 7/2010 | Fischer et al. |
| 2010/0240924 A1 | 9/2010 | Fischer et al. |
| 2010/0261934 A1 | 10/2010 | Fischer et al. |

FOREIGN PATENT DOCUMENTS

| | | |
|---|---|---|
| EP | 0 094 349 A2 | 5/1983 |
| EP | 0 174 562 A2 | 8/1985 |
| EP | 0 191 736 A2 | 2/1986 |
| EP | 0 269 806 A1 | 9/1987 |
| EP | 0 333 131 A1 | 3/1989 |
| EP | 0 346 620 A1 | 5/1989 |
| EP | 0 456 063 A2 | 4/1991 |
| EP | 0 453 086 A2 | 10/1991 |
| EP | 0 492 366 A2 | 12/1991 |
| EP | 0 521 334 A1 | 6/1992 |
| EP | 0 528 156 A1 | 7/1992 |
| EP | 0 582 198 A2 | 7/1993 |
| EP | 0 596 298 A2 | 10/1993 |
| EP | 0 613 618 A1 | 2/1994 |
| EP | 0 613 884 A2 | 2/1994 |
| EP | 0 613 885 A2 | 2/1994 |
| EP | 0 647 637 A1 | 8/1994 |
| EP | 0 664 081 A2 | 1/1995 |
| EP | 0 668 267 A1 | 1/1995 |
| EP | 0 681 865 A2 | 4/1995 |
| FR | 2 600 494 A1 | 12/1987 |
| WO | 91/07874 A1 | 6/1991 |
| WO | 91/08202 A1 | 6/1991 |
| WO | 92/16108 A1 | 10/1992 |
| WO | 95/01358 A1 | 1/1995 |
| WO | 95/07897 A1 | 3/1995 |
| WO | 95/20572 A1 | 8/1995 |
| WO | 95/26954 A1 | 10/1995 |
| WO | 96/20196 A1 | 7/1996 |
| WO | 96/25395 A1 | 8/1996 |
| WO | 96/35664 A1 | 11/1996 |
| WO | 97/01535 A1 | 1/1997 |
| WO | 97/02243 A1 | 1/1997 |
| WO | 97/36868 A1 | 10/1997 |
| WO | 98/05638 A2 | 2/1998 |
| WO | 98/06721 A1 | 2/1998 |
| WO | 98/25923 A1 | 6/1998 |
| WO | 98/25928 A1 | 6/1998 |
| WO | 98/35553 A1 | 8/1998 |
| WO | 99/16748 A1 | 4/1999 |
| WO | 99/24437 A1 | 5/1999 |
| WO | 99/43649 A1 | 9/1999 |
| WO | 99/48869 A1 | 9/1999 |
| WO | 99/55673 A1 | 11/1999 |
| WO | 99/66795 A1 | 12/1999 |
| WO | 00/35278 A1 | 6/2000 |
| WO | 01/17972 A2 | 3/2001 |
| WO | 01/23354 A2 | 4/2001 |
| WO | 01/74770 A1 | 10/2001 |
| WO | 02/46128 A2 | 6/2002 |
| WO | 03/013249 A1 | 2/2003 |
| WO | 2004/007448 A1 | 1/2004 |
| WO | 2004/024688 A1 | 3/2004 |
| WO | 2004/065366 A1 | 8/2004 |
| WO | 2004/080962 A1 | 9/2004 |
| WO | 2004/111042 A1 | 12/2004 |
| WO | 2005/044791 A2 | 5/2005 |
| WO | 2005/044796 A1 | 5/2005 |
| WO | 2005/048710 A1 | 6/2005 |
| WO | 2005/049569 A1 | 6/2005 |
| WO | 2005/066125 A1 | 7/2005 |
| WO | 2005/092897 A2 | 10/2005 |
| WO | 2006/000355 A1 | 1/2006 |
| WO | 2006/029799 A1 | 3/2006 |
| WO | 2006/056281 A1 | 6/2006 |
| WO | 2006/056282 A1 | 6/2006 |
| WO | 2006/089633 A2 | 8/2006 |

OTHER PUBLICATIONS

Harrison et al., "Use of molecular sieves in the methyl esterification of carboxylic acids," Chemistry and Industry, Nov. 1, 1968, p. 1568.

Sonntag N. "The Reactions of Aliphatic Acid Chlorides," Chem. Reviews, 52 (1953) pp. 237-416.

Bhattacharya B. "Isoquinoline Derivatives: Part XVIII—Formation of I-Alkyl-(or alkaryl or aryl)-3-methyl-7-chloro-(or 5-chloro)-isoquinolines," Indian J. Chem, 6 (1968) pp. 341-345.

Baur et al., "Polydisperse Ethoxylated Fatty Alcohol Surfactants as Accelerators of Cuticular Penetration. 1. Effects of Ethoxy Chain Length and the Size of the Penetrants," Pesticide Science51 (1997) pp. 131-152.

Ma et al., "Stereospecific synthesis of (1S,3R)-1-aminocyclopentane-1,3-dicarboxylic acid, a selective agonist of metabotropic glutamate receptors," Tetrahedron: Asymmetry, vol. 8, No. 6 (1997) pp. 825-827.

* cited by examiner

3'-ALKOXYSPIROCYCLOPENTYL-SUBSTITUTED TETRAMIC AND TETRONIC ACIDS

CROSS REFERENCE TO RELATED APPLICATIONS

This application claims priority from PCT/EP2006/011911 filed Dec. 11, 2006, which claims priority from DE 10 2005 059 891.9 filed Dec. 15, 2005 the content of which is incorporated herein by reference.

BACKGROUND OF THE INVENTION

1. Field of the Invention

The present invention relates to novel 3'-alkoxyspirocyclopentyl-substituted cyclic ketoenols, to a plurality of processes for their preparation and to their use as pesticides, microbicides and/or herbicides. The invention also provides selective herbicidal compositions comprising, firstly, the 3'-alkoxyspirocyclopentyl-substituted cyclic ketoenols and, secondly, a crop plant compatibility-improving compound.

2. Description of Related Art

The present invention further relates to the boosting of the action of crop protection compositions comprising, in particular, 3'-alkoxyspirocyclopentyl-substituted tetramic and tetronic acids, through the addition of ammonium salts or phosphonium salts and optionally penetrants, to the corresponding compositions, to processes for producing them and to their application in crop protection as insecticides and/or acaricides and/or for preventing unwanted plant growth.

1-H-Arylpyrrolidinedione derivatives having herbicidal, insecticidal or acaricidal action are known: EP-A-456 063, EP-A-521 334, EP-A-613 884, EP-A-613 885, WO 95/01358, WO 98/06721, WO 98/25928, WO 99/16748, WO 99/24437, WO 01/17972, WO 05/044791 or WO 05/048710.

Also known are alkoxy-substituted spirocyclic 1H-arylpyrrolidinedione derivatives: EP-A-596 298, WO 95/26954, WO 95/20572, EP-A-0 668 267, WO 96/25395, WO 96/35664, WO 97/01535, WO 97/02243, WO 97/36868, WO 98/05638, WO 99/43649, WO 99/48869, WO 99/55673, WO 01/23354, WO 01/74770, WO 01/17972, WO 03/013249, WO 04/024688, WO 04/065366, WO 04/080962, WO 04/007448, WO 04/111042, WO 05/044796, WO 05/049569, WO 05/066125, WO 05/092897, WO 06/000355, WO 06/029799, WO 06/056281, WO 06/056282, WO 06/089633.

It is known that certain $\Delta^3$-dihydrofuran-2-one derivatives have herbicidal, insecticidal or acaricidal properties: EP-A-528 156, EP-A-647 637, WO 95/26954, WO 96/20196, WO 96/25395, WO 96/35664, WO 97/01535, WO 97/02243, WO 97/36868, WO 98/05638, WO 98/06721, WO 99/16748, WO 98/25928, WO 99/43649, WO 99/48869, WO 99/55673, WO 01/23354, WO 01/74770, WO 01/17972, WO 2004/024688, WO 2004/080962, WO 04/111042, WO 05/092897, WO 06/000355, WO 06/029799, WO 06/089633.

However, the herbicidal and/or acaricidal and/or insecticidal activity and/or the activity spectrum and/or the compatibility of the known compounds with plants, in particular with crop plants, is not always sufficient.

SUMMARY OF THE INVENTION

This invention now provides novel compounds of the formula (I)

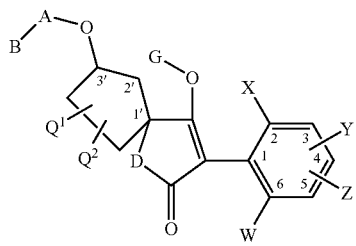

in which
W represents hydrogen, alkyl, alkenyl, alkynyl, halogen, alkoxy, haloalkyl, haloalkoxy or cyano,
X represents halogen, alkyl, alkenyl, alkynyl, alkoxy, alkoxyalkoxy, haloalkyl, haloalkoxy or cyano,
Y represents hydrogen, halogen, alkyl, alkenyl, alkynyl, alkoxy, cyano, haloalkyl, haloalkoxy, represents in each case optionally substituted phenyl or hetaryl,
Z represents hydrogen, halogen, alkyl, haloalkyl, cyano, alkoxy or haloalkoxy,
A represents an optionally substituted alkanediyl group or represents cycloalkyl which is optionally substituted and/or optionally interrupted by a heteroatom,
B represents hydrogen or in each case optionally substituted alkyl, alkenyl, alkoxy, alkoxy-alkoxy, phenyl, hetaryl or represents cycloalkyl which is optionally substituted and/or optionally interrupted by heteroatoms and/or C=O, or A represents a bond and B represents hydrogen,
D represents NH or oxygen,
$Q^1$ represents hydrogen, represents in each case optionally substituted alkyl, alkoxy, alkoxyalkyl or alkylthioalkyl, represents in each case optionally substituted cycloalkyl in which optionally one methylene group is replaced by heteroatoms or represents optionally substituted phenyl, hetaryl, phenylalkyl or hetarylalkyl,
$Q^2$ represents hydrogen or alkyl,
$Q^1$ and $Q^2$ together with the carbon to which they are attached represent an optionally substituted $C_3$-$C_6$-ring which may optionally be interrupted by a heteroatom, or
$Q^1$ and $Q^2$ together with the carbon atoms to which they are attached represent an optionally substituted $C_3$-$C_6$-ring which may optionally be interrupted by a heteroatom,
G represents hydrogen (a) or represents one of the groups (b)
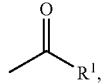

(c)
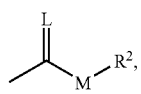

(d)
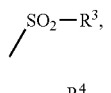

(e)

(f)
E, or (g)
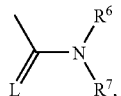

in which

E represents a metal ion or an ammonium ion,

L represents oxygen or sulfur,

M represents oxygen or sulfur, $R^1$ represents in each case optionally halogen- or cyano-substituted alkyl, alkenyl, alkoxyalkyl, alkylthioalkyl or polyalkoxyalkyl or represents in each case optionally halogen-, alkyl- or alkoxy-substituted cycloalkyl or heterocyclyl or represents in each case optionally substituted phenyl, phenylalkyl, hetaryl, phenoxyalkyl or hetaryloxyalkyl, $R^2$ represents in each case optionally halogen- or cyano-substituted alkyl, alkenyl, alkoxyalkyl or polyalkoxyalkyl or represents in each case optionally substituted cycloalkyl, phenyl or benzyl, $R^3$, $R^4$ and $R^5$ independently of one another represent in each case optionally halogen-substituted alkyl, alkoxy, alkylamino, dialkylamino, alkylthio, alkenylthio or cycloalkylthio or represent in each case optionally substituted phenyl, benzyl, phenoxy or phenylthio, $R^6$ and $R^7$ independently of one another represent hydrogen, represent in each case optionally halogen- or cyano-substituted alkyl, cycloalkyl, alkenyl, alkoxy, alkoxyalkyl, represent in each case optionally substituted phenyl or benzyl, or together with the N atom to which they are attached form an optionally substituted cycle which optionally contains oxygen or sulfur.

DETAILED DESCRIPTION OF A PREFERRED EMBODIMENT

Depending inter alia on the nature of the substituents, the compounds of the formula (I) may be present as optical isomers or isomer mixtures of varying composition which, if appropriate, may be separated in a customary manner. The present invention provides for the pure isomers and the isomer mixtures, their preparation and use and compositions comprising them. However, for the sake of simplicity, hereinbelow only compounds of the formula (I) are referred to, although what is meant are both the pure compounds and, if appropriate, mixtures having various proportions of isomeric compounds.

Including D for NH (1) and D for O (2), the following principal structures (I-1) to (I-2) result:

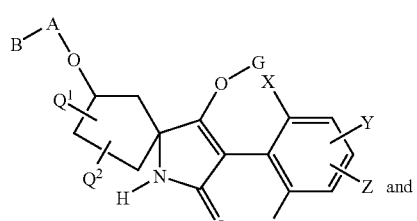
(I-1)

and

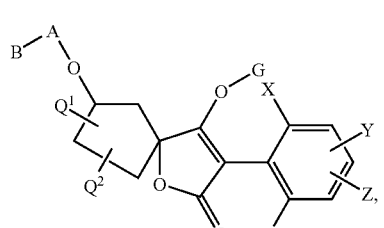
(I-2)

in which
A, B, G, $Q^1$, $Q^2$, W, X, Y and Z are as defined above.

Including the different meanings (a), (b), (c), (d), (e), (f) and (g) of group G, the following principal structures (I-1-a) to (I-1-g) result if D represents NH (1)

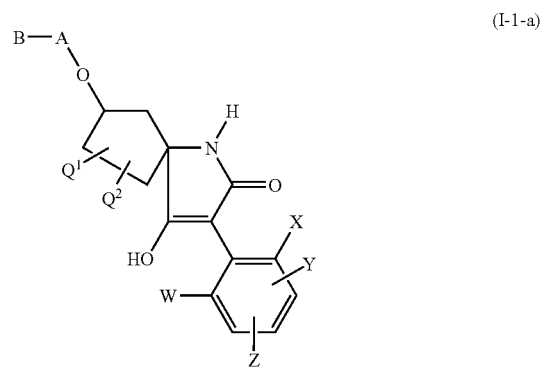
(I-1-a)

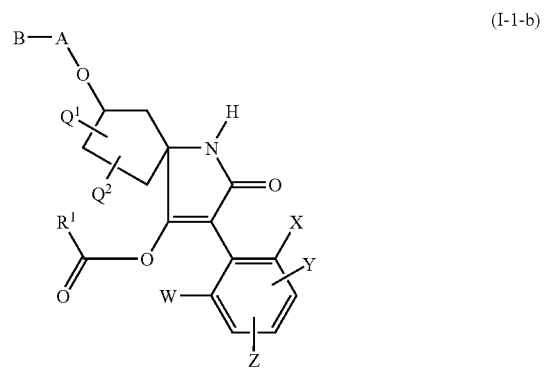
(I-1-b)

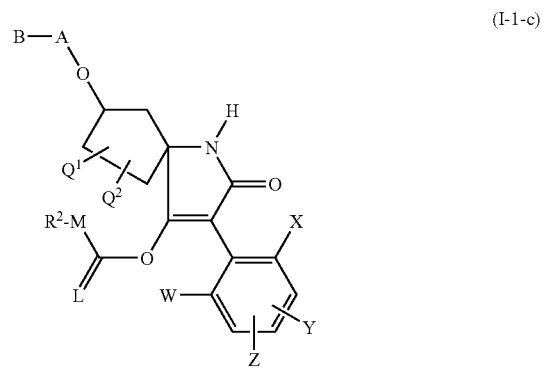
(I-1-c)

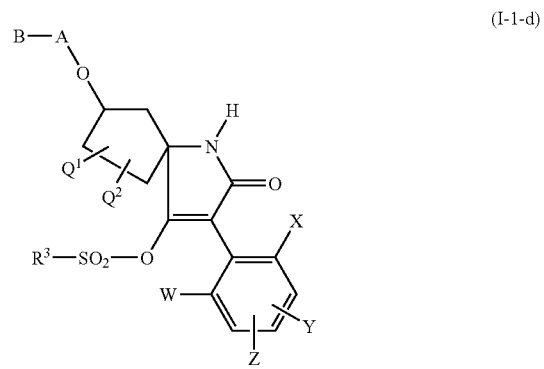
(I-1-d)

(I-1-e)
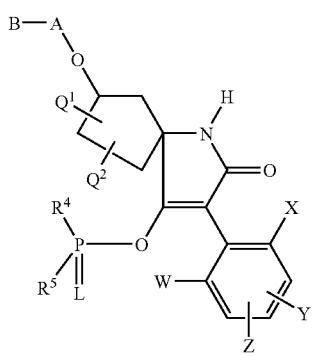
(I-1-f)
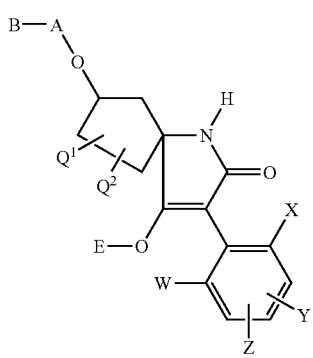
(I-1-g)
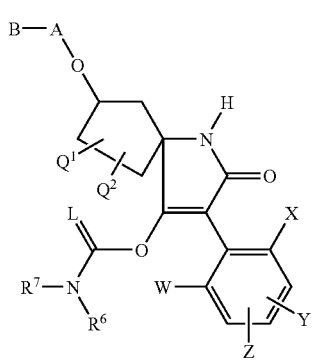
in which
A, B, E, L, M, Q¹, Q², W, X, Y, Z, R¹, R², R³, R⁴, R⁵, R⁶ and R⁷ are as defined above.
Including the different meanings (a), (b), (c), (d), (e), (f) and (g) of group G, the following principal structures (I-2-a) to (I-2-g) result if D represents O (2)
(I-2-a)
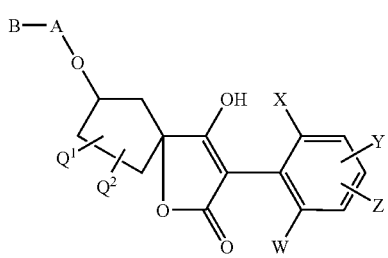
(I-2-b)
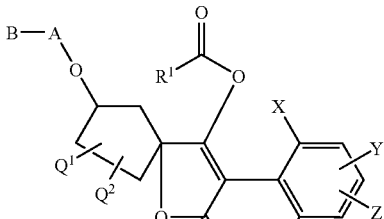
(I-2-c)
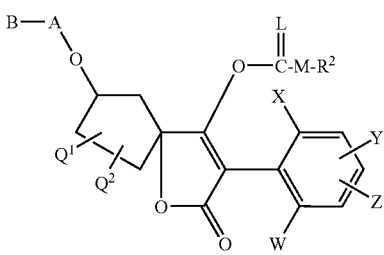
(I-2-d)
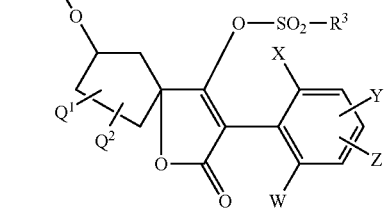
(I-2-e)
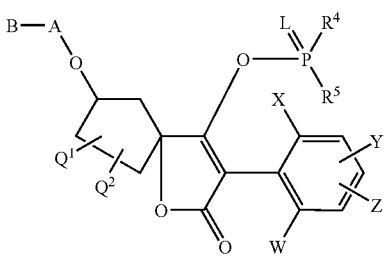
(I-2-f)
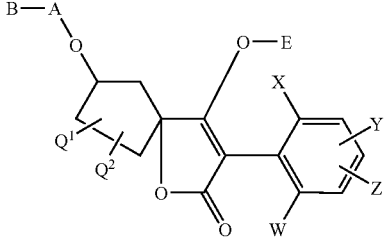
(I-2-g)
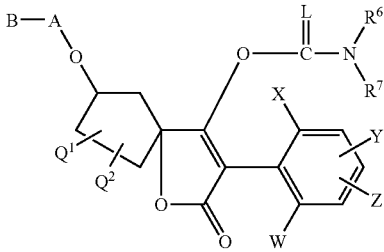
in which
A, B, E, L, M, Q¹, Q², W, X, Y, Z, R¹, R², R³, R⁴, R⁵, R⁶ and R⁷ are as defined above.

Furthermore, it has been found that the novel compounds of the formula (I) are obtained by the processes described below:

(A) Compounds of the formula (I-1-a)

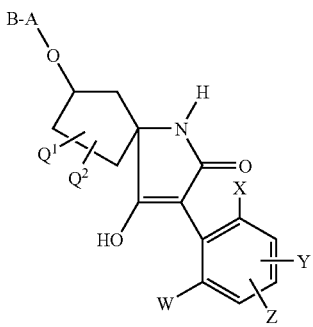
(I-1-a)

in which
A, B, $Q^1$, $Q^2$, W, X, Y and Z are as defined above
are obtained when
compounds of the formula (II)

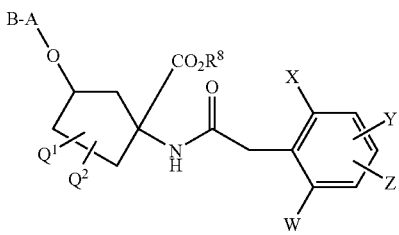
(II)

in which
A, B, $Q^1$, $Q^2$, W, X, Y and Z are as defined above
and
$R^8$ represents alkyl (preferably $C_1$-$C_6$-alkyl)
are condensed intramolecularly in the presence of a diluent and in the presence of a base.

(B) Moreover, it has been found that compounds of the formula (I-2-a)

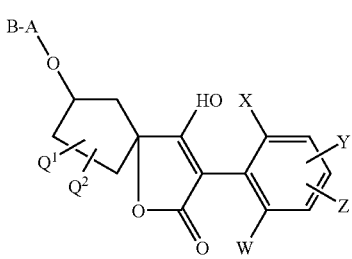
(I-2-a)

in which
A, B, $Q^1$, $Q^2$, W, X, Y and Z are as defined above
are obtained when
compounds of the formula (III)

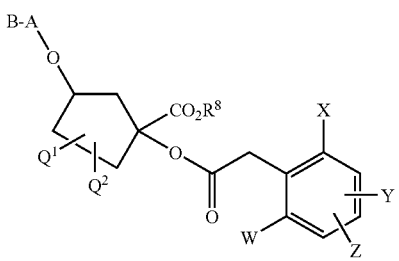
(III)

in which
A, B, $Q^1$, $Q^2$, W, X, Y, Z and $R^8$ are as defined above,
are condensed intramolecularly in the presence of a diluent and in the presence of a base.

Moreover, it has been found
(C) that the compounds of the formulae (I-1-b) to (I-2-b) shown above in which $R^1$, A, B, $Q^1$, $Q^2$, W, X, Y and Z are as defined above are obtained when compounds of the formulae (I-1-a) to (I-2-a) shown above in which A, B, $Q^1$, $Q^2$, W, X, Y and Z are as defined above are in each case
α) reacted with compounds of the formula (IV)

(IV)

in which
$R^1$ is as defined above and
Hal represents halogen (in particular chlorine or bromine)
or
β) reacted with carboxylic anhydrides of the formula (V)

$R^1$—CO—O—CO—$R^1$ (V)

in which
$R^1$ is as defined above,
if appropriate in the presence of a diluent and if appropriate in the presence of an acid binder;

(D) that the compounds of the formulae (I-1-c) to (I-2-c) shown above in which $R^2$, A, B, $Q^1$, $Q^2$, W, M, X, Y and Z are as defined above and L represents oxygen are obtained when compounds of the formulae (I-1-a) to (I-2-a) shown above in which A, B, $Q^1$, $Q^2$, W, X, Y and Z are as defined above are in each case
reacted with chloroformic esters or chloroformic thioesters of the formula (VI)

$R^2$-M-CO—Cl (VI)

in which
$R^2$ and M are as defined above,
if appropriate in the presence of a diluent and if appropriate in the presence of an acid binder;

(E) that compounds of the formulae (I-1-c) to (I-2-c) shown above in which $R^2$, A, B, $Q^1$, $Q^2$, W, M, X, Y and Z are as defined above and L represents sulfur are obtained when compounds of the formulae (I-1-a) to (I-2-a) shown above in which A, B, $Q^1$, $Q^2$, W, X, Y and Z are as defined above are in each case
reacted with chloromonothioformic esters or chlorodithioformic esters of the formula (VII)

(VII)

in which
M and $R^2$ are as defined above,
if appropriate in the presence of a diluent and if appropriate in the presence of an acid binder, (F) that compounds of the formulae (I-1-d) to (I-2-d) shown above in which $R^3$, A, B, W, $Q^1$, $Q^2$, X, Y and Z are as defined above are obtained when compounds of the formulae (I-1-a) to (I-2-a) shown above in which A, B, $Q^1$, $Q^2$, W, X, Y and Z are as defined above are in each case reacted with sulfonyl chlorides of the formula (VIII)

$$R^3—SO_2—Cl \quad (VIII)$$

in which
$R^3$ is as defined above,
if appropriate in the presence of a diluent and if appropriate in the presence of an acid binder, (G) that compounds of the formulae (I-1-e) to (I-2-e) shown above in which L, $R^4$, $R^5$, A, B, $Q^1$, $Q^2$, W, X, Y and Z are as defined above are obtained when compounds of the formulae (I-1-a) to (I-2-a) shown above in which A, B, $Q^1$, $Q^2$, W, X, Y and Z are as defined above are in each case reacted with phosphorus compounds of the formula (IX)

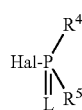

(IX)

in which
L, $R^4$ and $R^5$ are as defined above and
Hal represents halogen (in particular chlorine or bromine),
if appropriate in the presence of a diluent and if appropriate in the presence of an acid binder, (H) that compounds of the formulae (I-1-f) to (I-2-f) shown above in which E, A, B, $Q^1$, $Q^2$, W, X, Y and Z are as defined above are obtained when compounds of the formulae (I-1-a) to (I-2-a) shown above in which A, B, $Q^1$, $Q^2$, W, X, Y and Z are as defined above are in each case reacted with metal compounds or amines of the formulae (X) and (XI), respectively $$Me(OR^{10})_t \quad (X)$$

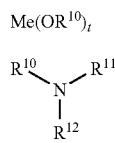

(XI)

in which
Me represents a mono- or divalent metal (preferably an alkali metal or alkaline earth metal, such as lithium, sodium, potassium, magnesium or calcium),
t represents the number 1 or 2 and
$R^{10}$, $R^{11}$, $R^{12}$ independently of one another represent hydrogen or alkyl (preferably $C_1$-$C_8$-alkyl),
if appropriate in the presence of a diluent, (I) that compounds of the formulae (I-1-g) to (I-2-g) shown above in which L, $R^6$, $R^7$, A, B, $Q^1$, $Q^2$, W, X, Y and Z are as defined above are obtained when compounds of the formulae (I-1-a) to (I-2-a) shown above in which A, B, $Q^1$, $Q^2$, W, X, Y and Z are as defined above are in each case
α) reacted with isocyanates or isothiocyanates of the formula (XII)

$$R^6—N=C=L \quad (XII)$$

in which
$R^6$ and L are as defined above,
if appropriate in the presence of a diluent and if appropriate in the presence of a catalyst, or
β) reacted with carbamoyl chlorides or thiocarbamoyl chlorides of the formula (XIII)

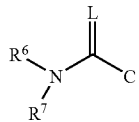

(XIII)

in which
L, $R^6$ and $R^7$ are as defined above,
if appropriate in the presence of a diluent and if appropriate in the presence of an acid binder.

Furthermore, it has been found that the novel compounds of the formula (I) are very effective as pesticides, preferably as insecticides, acaricides and/or fungicides and/or herbicides, and additionally frequently tolerated very well by plants, in particular by crop plants.

Surprisingly, it has now also been found that certain substituted cyclic ketoenols, when used together with the crop plant compatibility-improving compounds (safeners/antidotes) described below, efficiently prevent damage to the crop plants and can be used in a particularly advantageous manner as broad-spectrum combination preparations for the selective control of unwanted plants in crops of useful plants, such as, for example, in cereals, but also in maize, soya beans and rice.

The invention also provides selective herbicidal compositions comprising an effective amount of an active compound combination comprising, as components, (a') at least one compound of the formula (I) in which A, B, D, G, $Q^1$, $Q^2$, W, X, Y and Z are as defined above
and (b') at least one crop plant compatibility-improving compound from the following group of compounds:
4-dichloroacetyl-1-oxa-4-azaspiro[4.5]decane (AD-67, MON-4660), 1-dichloroacetylhexahydro-3,3,8a-trimethylpyrrolo[1,2-a]pyrimidin-6(2H)-one (dicyclonon, BAS-145138), 4-dichloroacetyl-3,4-dihydro-3-methyl-2H-1,4-benzoxazine (benoxacor), 1-methylhexyl 5-chloroquinoline-8-oxyacetate (cloquintocet-mexyl—cf. also related compounds in EP-A-86750, EP-A-94349, EP-A-191736, EP-A-492366), 3-(2-chlorobenzyl)-1-(1-methyl-1-phenylethyl)urea (cumyluron), α-(cyanomethoximino)phenylacetonitrile (cyometrinil), 2,4-dichlorophenoxyacetic acid (2,4-D), 4-(2,4-dichlorophenoxy)butyric acid (2,4-DB), 1-(1-methyl-1-phenylethyl)-3-(4-methylphenyl)urea (daimuron, dymron), 3,6-dichloro-2-methoxybenzoic acid (dicamba), S-1-methyl-1-phenylethyl piperidine-1-thiocarboxylate (dimepiperate), 2,2-dichloro-N-(2-oxo-2-(2-propenylamino)ethyl)-N-(2-propenyl)acetamide (DKA-24), 2,2-dichloro-N,N-di-2-propenylacetamide (dichlormid), 4,6-dichloro-2-phenylpyrimidine (fenclorim), ethyl 1-(2,4-dichlorophenyl)-5-trichloromethyl-1H-1,2,4-triazole-3-carboxylate (fenchlorazole-ethyl—cf. also related compounds in EP-A-174562 and EP-A-346620), phenylmethyl 2-chloro-4-trifluoromethylthiazole-5-carboxylate (flurazole), 4-chloro-N-(1,3-dioxolan-2-ylmethoxy)-α-trifluoroacetophenone oxime (fluxofenim), 3-dichloroacetyl-5-(2-furanyl)-2,2-dimethyloxazolidine (furilazole, MON-13900), ethyl 4,5-dihydro-5,5-diphenyl-3-isoxazolecarboxylate (isoxadifen-ethyl—cf. also related compounds in WO-A-95/07897), 1-(ethoxycarbonyl)ethyl 3,6-dichloro-2-methoxybenzoate (lactidichlor), (4-chloro-o-tolyloxy)acetic acid (MCPA), 2-(4-chloro-o-tolyloxy)propionic acid (mecoprop), diethyl 1-(2,4-dichlorophenyl)-4,5-dihydro-5-methyl-1H-pyrazole-3,5-dicarboxylate (mefenpyr-diethyl—cf. also related compounds in WO-A-91/07874), 2-dichloromethyl-2-methyl-1,3-dioxolane (MG-191), 2-propenyl-1-oxa-4-azaspiro[4.5]decane-4-carbodithioate (MG-838), 1,8-naphthalic anhydride, α-(1,3-dioxolan-2-ylmethoximino)phenylacetonitrile (oxabetrinil), 2,2-dichloro-N-(1,3-dioxolan-2-ylmethyl)-N-(2-propenyl)acetamide (PPG-1292), 3-dichloroacetyl-2,2- dimethyloxazolidine (R-28725), 3-dichloroacetyl-2,2,5-trimethyloxazolidine (R-29148), 4-(4-chloro-o-tolyl)butyric acid, 4-(4-chlorophenoxy)butyric acid, diphenylmethoxyacetic acid, methyl diphenylmethoxyacetate, ethyl diphenylmethoxyacetate, methyl 1-(2-chlorophenyl)-5-phenyl-1H-pyrazole-3-carboxylate, ethyl 1-(2,4-dichlorophenyl)-5-methyl-1H-pyrazole-3-carboxylate, ethyl 1-(2,4-dichlorophenyl)-5-isopropyl-1H-pyrazole-3-carboxylate, ethyl 1-(2,4-dichlorophenyl)-5-(1,1-dimethylethyl)-1H-pyrazole-3-carboxylate, ethyl 1-(2,4-dichlorophenyl)-5-phenyl-1H-pyrazole-3-carboxylate (cf. also related compounds in EP-A-269806 and EP-A-333131), ethyl 5-(2,4-dichlorobenzyl)-2-isoxazoline-3-carboxylate, ethyl 5-phenyl-2-isoxazoline-3-carboxylate, ethyl 5-(4-fluorophenyl)-5-phenyl-2-isoxazoline-3-carboxylate (cf. also related compounds in WO-A-91/08202), 1,3-dimethylbut-1-yl 5-chloroquinoline-8-oxyacetate, 4-allyloxybutyl 5-chloroquinoline-8-oxyacetate, 1-allyloxyprop-2-yl 5-chloroquinoline-8-oxyacetate, methyl 5-chloroquinoxaline-8-oxyacetate, ethyl 5-chloroquinoline-8-oxyacetate, allyl 5-chloroquinoxaline-8-oxyacetate, 2-oxoprop-1-yl 5-chloroquinoline-8-oxyacetate, diethyl 5-chloroquinoline-8-oxymalonate, diallyl 5-chloroquinoxaline-8-oxymalonate, diethyl 5-chloroquinoline-8-oxymalonate (cf. also related compounds in EP-A-582198), 4-carboxychroman-4-ylacetic acid (AC-304415, cf. EP-A-613618), 4-chlorophenoxyacetic acid, 3,3'-dimethyl-4-methoxybenzophenone, 1-bromo-4-chloromethylsulfonylbenzene, 1-[4-(N-2-methoxybenzoylsulfamoyl)phenyl]-3-methylurea (also known as N-(2-methoxybenzoyl)-4-[(methylaminocarbonyl)amino]benzenesulfonamide), 1-[4-(N-2-methoxybenzoylsulfamoyl)phenyl]-3,3-dimethylurea, 1-[4-(N-4,5-dimethylbenzoylsulfamoyl)phenyl]-3-methylurea, 1-[4-(N-naphthylsulfamoyl)phenyl]-3,3-dimethylurea, N-(2-methoxy-5-methylbenzoyl)-4-(cyclopropylaminocarbonyl)benzenesulfonamide, and/or one of the following compounds, defined by general formulae of the general formula (IIa)

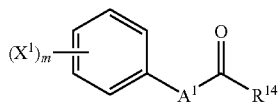

or of the general formula (IIb)

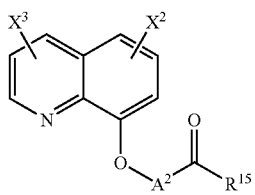

or of the formula (IIc)

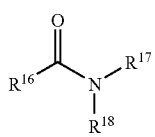

where m represents a number 0, 1, 2, 3, 4 or 5, $A^1$ represents one of the divalent heterocyclic groupings shown below,

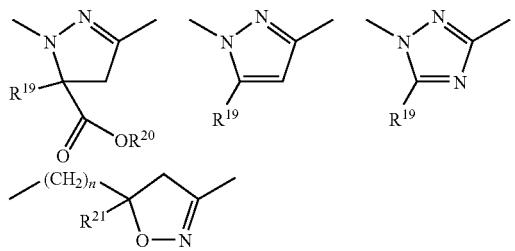

n represents a number 0, 1, 2, 3, 4 or 5, $A^2$ represents optionally $C_1$-$C_4$-alkyl- and/or $C_1$-$C_4$-alkoxycarbonyl- and/or $C_1$-$C_4$-alkenyloxy-carbonyl-substituted alkanediyl having 1 or 2 carbon atoms, $R^{14}$ represents hydroxyl, mercapto, amino, $C_1$-$C_6$-alkoxy, $C_1$-$C_6$-alkylthio, $C_1$-$C_6$-alkylamino or di($C_1$-$C_4$-alkyl)-amino, $R^{15}$ represents hydroxyl, mercapto, amino, $C_1$-$C_7$-alkoxy, $C_1$-$C_6$-alkenyloxy, $C_1$-$C_6$-alkenyloxy-$C_1$-$C_6$-alkoxy, $C_1$-$C_6$-alkylthio, $C_1$-$C_6$-alkylamino or di($C_1$-$C_4$-alkyl)-amino, $R^{16}$ represents optionally fluorine-, chlorine- and/or bromine-substituted $C_1$-$C_4$-alkyl, $R^{17}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, $R^{18}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, $R^{17}$ and $R^{18}$ also together represent $C_3$-$C_6$-alkanediyl or $C_2$-$C_5$-oxaalkanediyl, each of which is optionally substituted by $C_1$-$C_4$-alkyl, phenyl, furyl, a fused benzene ring or by two substituents which, together with the C atom to which they are attached, form a 5- or 6-membered carbocycle, $R^{19}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $R^{20}$ represents hydrogen, in each case optionally hydroxyl-, cyano-, halogen- or $C_1$-$C_4$-alkoxy-substituted $C_1$-$C_6$-alkyl, $C_3$-$C_6$-cycloalkyl or tri-($C_1$-$C_4$-alkyl)-silyl, $R^{21}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $X^1$ represents nitro, cyano, halogen, $C_1$-$C_4$-alkyl, $C_1$-$C_4$-haloalkyl, $C_1$-$C_4$-alkoxy or $C_1$-$C_4$-haloalkoxy, $X^2$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, $X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, and/or the following compounds, defined by general formulae of the general formula (IId)

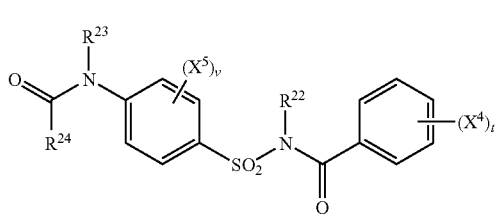

(IId)

or of the general formula (IIe)

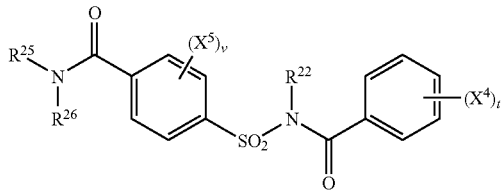

(IIe)

where t represents a number 0, 1, 2, 3, 4 or 5,
v represents a number 0, 1, 2, 3, 4 or 5,
$R^{22}$ represents hydrogen or $C_1$-$C_4$-alkyl,
$R^{23}$ represents hydrogen or $C_1$-$C_4$-alkyl,
$R^{24}$ represents hydrogen, in each case optionally cyano-, halogen- or $C_1$-$C_4$-alkoxy-substituted $C_1$-$C_6$-alkyl, $C_1$-$C_6$-alkoxy, $C_1$-$C_6$-alkylthio, $C_1$-$C_6$-alkylamino or di($C_1$-$C_4$-alkyl)-amino, or in each case optionally cyano-, halogen- or $C_1$-$C_4$-alkyl-substituted $C_3$-$C_6$-cycloalkyl, $C_3$-$C_6$-cycloalkyloxy, $C_3$-$C_6$-cycloalkylthio or $C_3$-$C_6$-cycloalkylamino,
$R^{25}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, or optionally cyano-, halogen- or $C_1$-$C_4$-alkyl-substituted $C_3$-$C_6$-cycloalkyl,
$R^{26}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, optionally cyano-, halogen- or $C_1$-$C_4$-alkyl-substituted $C_3$-$C_6$-cycloalkyl, or optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted phenyl, or together with $R^{25}$ represents in each case optionally $C_1$-$C_4$-alkyl-substituted $C_2$-$C_6$-alkanediyl or $C_2$-$C_5$-oxaalkanediyl,
$X^4$ represents nitro, cyano, carboxyl, carbamoyl, formyl, sulfamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy, and
$X^5$ represents nitro, cyano, carboxyl, carbamoyl, formyl, sulfamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy.

The formula (I) provides a general definition of the compounds according to the invention. Preferred substituents or ranges of the radicals listed in the formulae mentioned above and below are illustrated below:

W preferably represents hydrogen, $C_1$-$C_6$-alkyl, $C_2$-$C_6$-alkenyl, $C_2$-$C_6$-alkynyl, halogen, $C_1$-$C_6$-alkoxy, $C_1$-$C_4$-haloalkyl, $C_1$-$C_4$-haloalkoxy or cyano, X preferably represents hydrogen, $C_1$-$C_6$-alkyl, $C_2$-$C_6$-alkenyl, $C_2$-$C_6$-alkynyl, $C_1$-$C_6$-alkoxy, $C_1$-$C_6$-alkoxy-$C_1$-$C_4$-alkoxy, $C_1$-$C_4$-haloalkyl, $C_1$-$C_4$-haloalkoxy or cyano, Y preferably represents hydrogen, halogen, $C_1$-$C_6$-alkyl, $C_2$-$C_6$-alkenyl, $C_2$-$C_6$-alkynyl, $C_1$-$C_6$-alkoxy, cyano, $C_1$-$C_4$-haloalkyl, haloalkoxy, represents $V^1$- and $V^2$-substituted phenyl or pyridyl, $V^1$ preferably represents halogen, $C_1$-$C_{12}$-alkyl, $C_1$-$C_6$-alkoxy, $C_1$-$C_4$-haloalkyl, $C_1$-$C_4$-haloalkoxy, cyano or nitro, $V^2$ preferably represents hydrogen, halogen, $C_1$-$C_6$-alkyl, $C_1$-$C_6$-alkoxy or $C_1$-$C_4$-haloalkyl, $V^1$ and $V^2$ together preferably represent $C_3$-$C_4$-alkanediyl which may optionally be substituted by halogen and/or $C_1$-$C_2$-alkyl and which may optionally be interrupted by one or two oxygen atoms, Z preferably represents hydrogen, halogen, $C_1$-$C_6$-alkyl, $C_1$-$C_4$-haloalkyl, cyano, $C_1$-$C_6$-alkoxy or $C_1$-$C_4$-haloalkoxy, A preferably represents an optionally $C_1$-$C_4$-alkyl-substituted $C_1$-$C_4$-alkanediyl group or represents optionally $C_1$-$C_4$-alkyl-substituted $C_5$-$C_8$-cycloalkyl in which optionally one methylene group is replaced by oxygen, B preferably represents hydrogen or represents in each case optionally halogen-substituted $C_1$-$C_8$-alkyl, $C_2$-$C_8$-alkenyl, $C_1$-$C_6$-alkoxy, $C_1$-$C_6$-alkoxy-$C_1$-$C_4$-alkoxy, $C_1$-$C_4$-alkoxy-bis-$C_1$-$C_4$-alkoxy, represents optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl, represents optionally halogen-, $C_1$-$C_4$-alkyl- or $C_1$-$C_2$-haloalkyl-substituted pyridyl, pyrimidyl, thiazolyl or thienyl or represents optionally halogen-, $C_1$-$C_4$-alkyl-, $C_1$-$C_4$-alkoxy- or $C_1$-$C_2$-haloalkyl-substituted $C_3$-$C_8$-cycloalkyl in which optionally one or two not directly adjacent methylene groups are replaced by oxygen, two methylene groups are replaced by the radical —O—CO— or three methylene groups are replaced by the radical —O—CO—O—, or A preferably represents a bond and B represents hydrogen, D preferably represents NH or oxygen, $Q^1$ preferably represents hydrogen or represents in each case optionally halogen-substituted $C_1$-$C_6$-alkyl, $C_1$-$C_6$-alkoxy, $C_1$-$C_4$-alkoxy-$C_1$-$C_4$-alkyl, $C_1$-$C_4$-alkylthio-$C_1$-$C_4$-alkyl or represents optionally halogen-, $C_1$-$C_4$-alkyl- or $C_1$-$C_4$-alkoxy-substituted $C_3$-$C_6$-cycloalkyl in which optionally one methylene group is replaced by oxygen or represents phenyl, phenyl-$C_1$-$C_2$-alkyl or hetaryl, each of which is optionally mono- or disubstituted by halogen, $C_1$-$C_4$-alkyl, $C_1$-$C_4$-alkoxy, $C_1$-$C_4$-haloalkyl or $C_1$-$C_4$-haloalkoxy, $Q^2$ preferably represents hydrogen or $C_1$-$C_6$-alkyl, or $Q^1$ and $Q^2$ together with the carbon to which they are attached preferably represent a $C_3$-$C_6$-ring which is optionally mono- or disubstituted by fluorine, chlorine, $C_1$-$C_4$-alkyl, $C_1$-$C_4$-alkoxy or trifluoromethyl and in which optionally one methylene group may be replaced by oxygen, or $Q^1$ and $Q^2$ together with the carbon atoms to which they are attached preferably represent a $C_3$-$C_6$-ring which is optionally mono- or disubstituted by fluorine, chlorine, $C_1$-$C_4$-alkyl, $C_1$-$C_4$-alkoxy or trifluoromethyl and in which optionally one methylene group may be replaced by oxygen.

G preferably represents hydrogen (a) or represents one of the groups

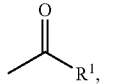 (b)

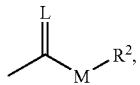 (c)

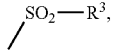 (d)

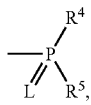 (e)

E, or (f)

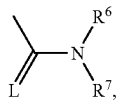 (g)

in which

E represents a metal ion or an ammonium ion,

L represents oxygen or sulfur and

M represents oxygen or sulfur, $R^1$ preferably represents in each case optionally halogen- or cyano-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl or poly-$C_1$-$C_8$-alkoxy-$C_1$-$C_8$-alkyl or represents optionally halogen-, $C_1$-$C_6$-alkyl- or $C_1$-$C_6$-alkoxy-substituted $C_3$-$C_8$-cycloalkyl in which optionally one or two not directly adjacent methylene groups are replaced by oxygen and/or sulfur, preferably represents optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkylsulfonyl-substituted phenyl, preferably represents optionally halogen-, nitro-, cyano-, $C_1$-$C_6$-alkyl-, $C_1$-$C_6$-alkoxy-, $C_1$-$C_6$-haloalkyl- or $C_1$-$C_6$-haloalkoxy-substituted phenyl-$C_1$-$C_6$-alkyl, preferably represents optionally halogen- or $C_1$-$C_6$-alkyl-substituted 5- or 6-membered hetaryl having one or two heteroatoms from the group consisting of oxygen, sulfur and nitrogen, preferably represents optionally halogen- or $C_1$-$C_6$-alkyl-substituted phenoxy-$C_1$-$C_6$-alkyl or preferably represents optionally halogen-, amino- or $C_1$-$C_6$-alkyl-substituted 5- or 6-membered hetaryloxy-$C_1$-$C_6$-alkyl having one or two heteroatoms from the group consisting of oxygen, sulfur and nitrogen, $R^2$ preferably represents in each case optionally halogen- or cyano-substituted $C_1$-$C_{20}$-alkyl, $C_2$-$C_{20}$-alkenyl, $C_1$-$C_8$-alkoxy-$C_2$-$C_8$-alkyl or poly-$C_1$-$C_8$-alkoxy-$C_2$-$C_8$-alkyl, preferably represents optionally halogen-, $C_1$-$C_6$-alkyl- or $C_1$-$C_6$-alkoxy-substituted $C_3$-$C_8$-cycloalkyl or preferably represents in each case optionally halogen-, cyano-, nitro-, $C_1$-$C_6$-alkyl-, $C_1$-$C_6$-alkoxy-, $C_1$-$C_6$-haloalkyl- or $C_1$-$C_6$-haloalkoxy-substituted phenyl or benzyl, $R^3$ preferably represents optionally halogen-substituted $C_1$-$C_8$-alkyl or in each case optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl, $R^4$ and $R^5$ independently of one another preferably represent in each case optionally halogen-substituted $C_1$-$C_8$-alkyl, $C_1$-$C_8$-alkoxy, $C_1$-$C_8$-alkylamino, di-($C_1$-$C_8$-alkyl)amino, $C_1$-$C_8$-alkylthio or $C_3$-$C_8$-alkenylthio or represent in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkyl- or $C_1$-$C_4$-haloalkyl-substituted phenyl, phenoxy or phenylthio, $R^6$ and $R^7$ independently of one another preferably represent hydrogen, represent in each case optionally halogen- or cyano-substituted $C_1$-$C_8$-alkyl, $C_3$-$C_8$-cycloalkyl, $C_1$-$C_8$-alkoxy, $C_3$-$C_8$-alkenyl or $C_1$-$C_8$-alkoxy-$C_2$-$C_8$-alkyl, represent in each case optionally halogen-, $C_1$-$C_8$-alkyl-, $C_1$-$C_8$-haloalkyl- or $C_1$-$C_8$-alkoxy-substituted phenyl or benzyl or together represent an optionally $C_1$-$C_6$-alkyl-substituted $C_3$-$C_6$-alkylene radical in which optionally one methylene group is replaced by oxygen or sulfur.

In the radical definitions mentioned as being preferred, halogen represents fluorine, chlorine, bromine and iodine, in particular fluorine, chlorine and bromine.

W particularly preferably represents hydrogen, chlorine, bromine, iodine, $C_1$-$C_4$-alkyl, $C_2$-$C_4$-alkenyl, $C_2$-$C_4$-alkynyl, $C_1$-$C_4$-alkoxy, $C_1$-$C_2$-haloalkyl or $C_1$-$C_2$-haloalkoxy, X particularly preferably represents chlorine, bromine, iodine, $C_1$-$C_4$-alkyl, $C_2$-$C_4$-alkenyl, $C_2$-$C_4$-alkynyl, $C_1$-$C_4$-alkoxy, $C_1$-$C_4$-alkoxy-$C_1$-$C_3$-alkoxy, $C_1$-$C_2$-haloalkyl, $C_1$-$C_2$-haloalkoxy or cyano, Y particularly preferably in the 4-position represents hydrogen, fluorine, chlorine, bromine, iodine, methoxy, ethoxy, cyano, trifluoromethyl, difluoromethoxy or trifluoromethoxy, Z particularly preferably represents hydrogen.

W also particularly preferably represents hydrogen, chlorine, bromine or $C_1$-$C_4$-alkyl, X also particularly preferably represents chlorine, bromine, $C_1$-$C_4$-alkyl, $C_1$-$C_4$-alkoxy, $C_1$-$C_2$-haloalkyl, $C_1$-$C_2$-haloalkoxy or cyano, Y also particularly preferably in the 4-position represents $C_2$-$C_4$-alkenyl, $C_2$-$C_4$-alkynyl or represents the radical

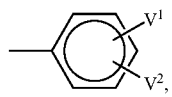

Z also particularly preferably represents hydrogen, $V^1$ also particularly preferably represents fluorine, chlorine, $C_1$-$C_4$-alkyl, $C_1$-$C_4$-alkoxy, $C_1$-$C_2$-haloalkyl or $C_1$-$C_2$-haloalkoxy, $V^2$ also particularly preferably represents hydrogen, fluorine, chlorine, $C_1$-$C_4$-alkyl, $C_1$-$C_4$-alkoxy or $C_1$-$C_2$-haloalkyl, $V^1$ and $V^2$ together also particularly preferably represent —O—$CH_2$—O— and —O—$CF_2$—O—.

W likewise particularly preferably represents hydrogen, chlorine, bromine or $C_1$-$C_4$-alkyl, X likewise particularly preferably represents chlorine, bromine, $C_1$-$C_4$-alkyl or $C_1$-$C_2$-haloalkyl, Y likewise particularly preferably in the 5-position represents $C_2$-$C_4$-alkenyl, $C_2$-$C_4$-alkynyl, represents the radical

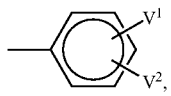

Z likewise particularly preferably in the 4-position represents hydrogen, $C_1$-$C_4$-alkyl or chlorine, $V^1$ likewise particularly preferably represents fluorine, chlorine, $C_1$-$C_4$-alkyl, $C_1$-$C_4$-alkoxy, $C_1$-$C_2$-haloalkyl or $C_1$-$C_2$-haloalkoxy, $V^2$ likewise particularly preferably represents hydrogen, fluorine, chlorine, $C_1$-$C_4$-alkyl, $C_1$-$C_4$-alkoxy or $C_1$-$C_2$-haloalkyl, $V^1$ and $V^2$ together likewise particularly preferably represent —O—CH$_2$—O— or —O—CF$_2$—O—.

W moreover particularly preferably represents hydrogen, $C_1$-$C_4$-alkyl, $C_2$-$C_4$-alkenyl, $C_2$-$C_4$-alkynyl, $C_1$-$C_4$-alkoxy, chlorine, bromine, iodine or trifluoromethyl, X moreover particularly preferably represents chlorine, bromine, iodine, $C_1$-$C_4$-alkyl, $C_2$-$C_4$-alkenyl, $C_2$-$C_4$-alkynyl, $C_1$-$C_4$-alkoxy, $C_1$-$C_4$-alkoxy-$C_1$-$C_3$-alkoxy, $C_1$-$C_2$-haloalkyl, $C_1$-$C_2$-haloalkoxy or cyano, Y moreover particularly preferably in the 4-position represents $C_1$-$C_4$-alkyl, Z moreover particularly preferably represents hydrogen.

W furthermore particularly preferably represents hydrogen, chlorine, bromine, iodine, $C_1$-$C_4$-alkyl or $C_1$-$C_4$-alkoxy, X furthermore particularly preferably represents chlorine, bromine, iodine, $C_1$-$C_4$-alkyl, $C_1$-$C_4$-alkoxy, $C_1$-$C_2$-haloalkyl, $C_1$-$C_2$-haloalkoxy or cyano, Y furthermore particularly preferably in the 4-position represents hydrogen, chlorine, bromine, $C_1$-$C_4$-alkyl, $C_1$-$C_2$-haloalkyl or $C_1$-$C_2$-haloalkoxy, Z furthermore particularly preferably in the 3- or 5-position represents fluorine, chlorine, bromine, iodine, $C_1$-$C_4$-alkyl, $C_1$-$C_2$-haloalkyl, $C_1$-$C_4$-alkoxy or $C_1$-$C_2$-haloalkoxy.

A particularly preferably represents an optionally $C_1$-$C_2$-alkyl-substituted by $C_1$-$C_3$-alkanediyl group or represents $C_5$-$C_6$-cycloalkyl in which optionally one methylene group is replaced by oxygen, B particularly preferably represents hydrogen or $C_1$-$C_6$-alkyl, $C_2$-$C_6$-alkenyl, $C_1$-$C_4$-alkoxy, $C_1$-$C_4$-alkoxy-$C_1$-$C_3$-alkoxy, $C_1$-$C_4$-alkoxy-bis-$C_1$-$C_3$-alkoxy, each of which is optionally mono- to trisubstituted by fluorine or chlorine, represents phenyl which is optionally mono- to trisubstituted by fluorine, chlorine, bromine, $C_1$-$C_4$-alkyl, $C_1$-$C_4$-alkoxy, $C_1$-$C_2$-haloalkyl, $C_1$-$C_2$-haloalkoxy, cyano or nitro, represents pyridyl, pyrimidyl, thiazolyl or thienyl, each of which is optionally mono- or disubstituted by fluorine, chlorine, bromine, methyl, ethyl or trifluoromethyl or represents $C_3$-$C_6$-cycloalkyl which is optionally mono- or disubstituted by fluorine, chlorine, methyl, methoxy or trifluoromethyl, in which optionally one or two not directly adjacent methylene groups are replaced by oxygen, or A particularly preferably represents a bond and B represents hydrogen.

D particularly preferably represents NH or oxygen.

$Q^1$ particularly preferably represents hydrogen, represents $C_1$-$C_4$-alkyl which is optionally mono- to trisubstituted by fluorine, $Q^2$ particularly preferably represents hydrogen or $C_1$-$C_4$-alkyl.

$Q^1$ and $Q^2$ together with the carbon atom to which they are attached particularly preferably represent a $C_3$-$C_6$-ring which is optionally monosubstituted by fluorine, methyl, methoxy or trifluoromethyl and in which one methylene group may be replaced by oxygen, or $Q^1$ and $Q^2$ together with the carbon atoms to which they are attached particularly preferably represent a $C_3$-$C_6$-ring which is optionally monosubstituted by fluorine, methyl, methoxy or trifluoromethyl and in which one methylene group may be replaced by oxygen.

G particularly preferably represents hydrogen (a) or represents one of the groups

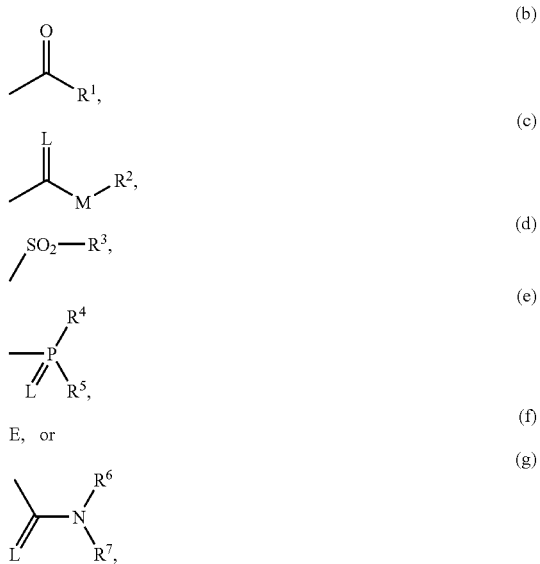

in which

E represents a metal ion or an ammonium ion,

L represents oxygen or sulfur and

M represents oxygen or sulfur.

$R^1$ particularly preferably represents $C_1$-$C_{16}$-alkyl, $C_2$-$C_{16}$-alkenyl, $C_1$-$C_6$-alkoxy-$C_1$-$C_4$-alkyl, $C_1$-$C_6$-alkylthio-$C_1$-$C_4$-alkyl or poly-$C_1$-$C_6$-alkoxy-$C_1$-$C_4$-alkyl, each of which is optionally mono- to trisubstituted by fluorine or chlorine, or represents $C_3$-$C_7$-cycloalkyl which is optionally mono- to disubstituted by fluorine, chlorine, $C_1$-$C_5$-alkyl or $C_1$-$C_5$-alkoxy and in which optionally one or two not directly adjacent methylene groups are replaced by oxygen and/or sulfur, particularly preferably represents phenyl which is optionally mono- to trisubstituted by fluorine, chlorine, bromine, cyano, nitro, $C_1$-$C_4$-alkyl, $C_1$-$C_4$-alkoxy, $C_1$-$C_3$-haloalkyl, $C_1$-$C_3$-haloalkoxy, $C_1$-$C_4$-alkylthio or $C_1$-$C_4$-alkylsulfonyl, particularly preferably represents phenyl-$C_1$-$C_4$-alkyl which is optionally mono- to disubstituted by fluorine, chlorine, bromine, $C_1$-$C_4$-alkyl, $C_1$-$C_4$-alkoxy, $C_1$-$C_3$-haloalkyl or $C_1$-$C_3$-haloalkoxy, particularly preferably represents pyrazolyl, thiazolyl, pyridyl, pyrimidyl, furanyl or thienyl, each of which is optionally mono- to disubstituted by fluorine, chlorine, bromine or $C_1$-$C_4$-alkyl, particularly preferably represents phenoxy-$C_1$-$C_5$-alkyl which is optionally mono- to disubstituted by fluorine, chlorine, bromine or $C_1$-$C_4$-alkyl or particularly preferably represents pyridyloxy-$C_1$-$C_5$-alkyl, pyrimidyloxy-$C_1$-$C_5$-alkyl or thiazolyloxy-$C_1$-$C_5$-alkyl, each of which is optionally mono- to disubstituted by fluorine, chlorine, bromine, amino or $C_1$-$C_4$-alkyl, $R^2$ particularly preferably represents $C_1$-$C_{16}$-alkyl, $C_2$-$C_{16}$-alkenyl, $C_1$-$C_6$-alkoxy-$C_2$-$C_6$-alkyl or poly-$C_1$-$C_6$-alkoxy-$C_2$-$C_6$-alkyl, each of which is optionally mono- to trisubstituted by fluorine or chlorine, particularly preferably represents $C_3$-$C_7$-cycloalkyl which is optionally mono- to disubstituted by fluorine, chlorine, $C_1$-$C_4$-alkyl or $C_1$-$C_4$-alkoxy or particularly preferably represents phenyl or benzyl, each of which is optionally mono- to trisubstituted by fluorine, chlorine, bromine, cyano, nitro, $C_1$-$C_4$-alkyl, $C_1$-$C_3$-alkoxy, $C_1$-$C_3$-haloalkyl or $C_1$-$C_3$-haloalkoxy, $R^3$ particularly preferably represents $C_1$-$C_6$-alkyl which is optionally mono- to trisubstituted by fluorine or chlorine or represents phenyl or benzyl, each of which is optionally mono- to disubstituted by fluorine, chlorine, bromine, $C_1$-$C_4$-alkyl, $C_1$-$C_4$-alkoxy, $C_1$-$C_2$-haloalkoxy, $C_1$-$C_2$-haloalkyl, cyano or nitro, $R^4$ and $R^5$ independently of one another particularly preferably represent $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio or $C_3$-$C_4$-alkenylthio, each of which is optionally mono- to trisubstituted by fluorine or chlorine, or represent phenyl, phenoxy or phenylthio, each of which is optionally mono- to disubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl or $C_1$-$C_3$-haloalkyl, $R^6$ and $R^7$ independently of one another particularly preferably represent hydrogen, represent $C_1$-$C_6$-alkyl, $C_3$-$C_6$-cycloalkyl, $C_1$-$C_6$-alkoxy, $C_3$-$C_6$-alkenyl or $C_1$-$C_6$-alkoxy-$C_2$-$C_6$-alkyl, each of which is optionally mono- to trisubstituted by fluorine or chlorine, represent phenyl or benzyl, each of which is optionally mono- to trisubstituted by fluorine, chlorine, bromine, $C_1$-$C_5$-haloalkyl, $C_1$-$C_5$-alkyl or $C_1$-$C_5$-alkoxy, or together represent an optionally $C_1$-$C_4$-alkyl-substituted $C_3$-$C_6$-alkylene radical in which optionally one methylene group is replaced by oxygen or sulfur.

In the radical definitions mentioned as being particularly preferred, halogen represents fluorine, chlorine and bromine, in particular fluorine and chlorine.

W very particularly preferably represents hydrogen, chlorine, bromine, iodine, methyl, ethyl, methoxy, ethoxy or trifluoromethyl, X very particularly preferably represents chlorine, bromine, iodine, methyl, ethyl, propyl, methoxy, ethoxy, propoxy, methoxyethoxy, ethoxyethoxy, trifluoromethyl, difluoromethoxy, trifluoromethoxy or cyano, Y in the 4-position very particularly preferably represents hydrogen, chlorine, bromine, iodine, trifluoromethyl or trifluoromethoxy, Z very particularly preferably represents hydrogen.

W also very particularly preferably represents hydrogen, chlorine, bromine, methyl or ethyl, X also very particularly preferably represents chlorine, bromine, methyl, ethyl, propyl, methoxy, trifluoromethyl, difluoromethoxy or cyano, Y also very particularly preferably in the 4-position represents vinyl, ethynyl, propynyl or represents the radical

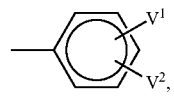

Z also very particularly preferably represents hydrogen, $V^1$ also very particularly preferably represents fluorine, chlorine, methyl, methoxy, trifluoromethyl or trifluoromethoxy, $V^2$ also very particularly preferably represents hydrogen, fluorine, chlorine, methyl, methoxy or trifluoromethyl.

W likewise very particularly preferably represents hydrogen, chlorine or methyl, X likewise very particularly preferably represents chlorine, methyl or trifluoromethyl, Y likewise very particularly preferably in the 5-position represents vinyl, ethynyl, propynyl or represents the radical

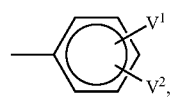

Z likewise very particularly preferably in the 4-position represents hydrogen or methyl, $V^1$ likewise very particularly preferably represents fluorine, chlorine, methyl, methoxy, trifluoromethyl or trifluoromethoxy, $V^2$ likewise very particularly preferably represents hydrogen, fluorine, chlorine, methyl, methoxy or trifluoromethyl.

W moreover very particularly preferably represents hydrogen, methyl, ethyl, methoxy, ethoxy, chlorine, bromine or iodine, X moreover very particularly preferably represents chlorine, bromine, iodine, methyl, ethyl, propyl, methoxy, ethoxy, propoxy, methoxy-ethoxy, ethoxy-ethoxy, trifluoromethyl, difluoromethoxy, trifluoromethoxy or cyano, Y moreover very particularly preferably in the 4-position represents methyl or ethyl, Z moreover very particularly preferably represents hydrogen.

W furthermore very particularly preferably represents hydrogen, chlorine, bromine, iodine, methyl or ethyl, X furthermore very particularly preferably represents chlorine, bromine, iodine, methyl, ethyl, methoxy, trifluoromethyl, difluoromethoxy or trifluoromethoxy, Y furthermore very particularly preferably in the 4-position represents hydrogen, chlorine, bromine, iodine, methyl or ethyl, Z furthermore very particularly preferably in the 3- or 5-position represents fluorine, chlorine, bromine, iodine, methyl, ethyl, trifluoromethyl or trifluoromethoxy.

A very particularly preferably represents —$CH_2$—, —$CHCH_3$—, —$CH_2$—$CH_2$—, —$CH_2$—$CHCH_3$—, —$CH_2$—$CH_2$—$CH_2$—.

B very particularly preferably represents hydrogen, methyl, ethyl, propyl, isopropyl, butyl, isobutyl, $C_2$-$C_4$-alkenyl, methoxy, ethoxy, propoxy, isopropoxy, butoxy, isobutoxy, methoxy-ethoxy, ethoxy-ethoxy, represents phenyl which is optionally mono- or disubstituted by fluorine, chlorine, bromine, methyl, methoxy, trifluoromethyl, trifluoromethoxy, cyano or nitro, represents cyclopropyl, represents cyclopentyl or cyclohexyl in which optionally one methylene group is replaced by oxygen, or A very particularly preferably represents a bond and B represents hydrogen.

D very particularly preferably represents NH or oxygen.
Q¹ very particularly preferably represents hydrogen, methyl or ethyl.
Q² very particularly preferably represents hydrogen, methyl or ethyl.
Q¹ and Q² together with the carbon atom to which they are attached very particularly preferably represent cyclopropyl, cyclopentyl or cyclohexyl, or
Q¹ and Q² together with the carbon atoms to which they are attached very particularly preferably represent a $C_5$-$C_6$- ring which is optionally interrupted by oxygen.
G very particularly preferably represents hydrogen (a) or represents one of the groups

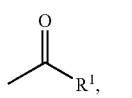
(b)

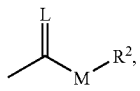
(c)

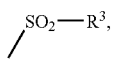
(d)

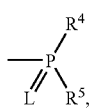
(e)

E or
(f)

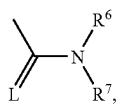
(g)

in which
E represents a metal ion or an ammonium ion,
L represents oxygen or sulfur and
M represents oxygen or sulfur.
R¹ very particularly preferably represents $C_1$-$C_{10}$-alkyl, $C_2$-$C_{10}$-alkenyl, $C_1$-$C_4$-alkoxy-$C_1$-$C_2$-alkyl, $C_1$-$C_4$-alkylthio-$C_1$-$C_2$-alkyl, each of which is optionally mono- to trisubstituted by fluorine or chlorine, or represents $C_3$-$C_6$-cycloalkyl which is optionally monosubstituted by fluorine, chlorine, methyl, ethyl or methoxy,
very particularly preferably represents phenyl which is optionally mono- to disubstituted by fluorine, chlorine, bromine, cyano, nitro, methyl, ethyl, n-propyl, isopropyl, methoxy, ethoxy, trifluoromethyl or trifluoromethoxy,
very particularly preferably represents furanyl, thienyl or pyridyl, each of which is optionally monosubstituted by chlorine, bromine or methyl,
R² very particularly preferably represents $C_1$-$C_{10}$-alkyl, $C_2$-$C_{10}$-alkenyl or $C_1$-$C_4$-alkoxy-$C_2$-$C_4$-alkyl, each of which is optionally mono- to trisubstituted by fluorine or chlorine,
very particularly preferably represents cyclopentyl or cyclohexyl
or very particularly preferably represents phenyl or benzyl, each of which is optionally mono- to disubstituted by fluorine, chlorine, cyano, nitro, methyl, ethyl, methoxy, trifluoromethyl or trifluoromethoxy,
R³ very particularly preferably represents methyl, ethyl, propyl or isopropyl, each of which is optionally mono- to trisubstituted by fluorine or chlorine, or represents phenyl which is optionally monosubstituted by fluorine, chlorine, bromine, methyl, ethyl, isopropyl, tert-butyl, methoxy, ethoxy, isopropoxy, trifluoromethyl, trifluoromethoxy, cyano or nitro,
R⁴ and R⁵ independently of one another very particularly preferably represent $C_1$-$C_4$-alkoxy or $C_1$-$C_4$-alkylthio or represent phenyl, phenoxy or phenylthio, each of which is optionally monosubstituted by fluorine, chlorine, bromine, nitro, cyano, methyl, methoxy, trifluoromethyl or trifluoromethoxy,
R⁶ and R⁷ independently of one another very particularly preferably represent hydrogen, represent $C_1$-$C_4$-alkyl, $C_3$-$C_6$-cycloalkyl, $C_1$-$C_4$-alkoxy, $C_3$-$C_4$-alkenyl or $C_1$-$C_4$-alkoxy-$C_2$-$C_4$-alkyl, represent phenyl which is optionally mono- to disubstituted by fluorine, chlorine, bromine, methyl, methoxy or trifluoromethyl, or together represent a $C_5$-$C_6$-alkylene radical in which optionally one methylene group is replaced by oxygen or sulfur.
W especially preferably represents methyl, ethyl or methoxy,
X especially preferably represents chlorine, methyl, ethyl or methoxy,
Y especially preferably in the 4-position represents chlorine or bromine,
Z especially preferably represents hydrogen.
W likewise especially preferably represents hydrogen,
X likewise especially preferably represents methyl,
Y likewise especially preferably in the 5-position represents the radical

Z especially preferably in the 4-position represents hydrogen.
W moreover especially preferably represents methyl or ethyl,
X moreover especially preferably represents chlorine, bromine or methyl,
Y moreover especially preferably in the 4-position represents methyl,
Z moreover especially preferably represents hydrogen.
A especially preferably represents —CH₂— or —CH₂—CH₂—,
B especially preferably represents hydrogen, methyl, ethyl, propyl, methoxy or cyclopropyl,
or A especially preferably represents a bond and B represents hydrogen.
D especially preferably represents NH.
Q¹ especially preferably represents hydrogen.
Q² especially preferably represents hydrogen.
G especially preferably represents hydrogen (a) or represents one of the groups

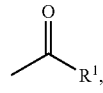
(b)

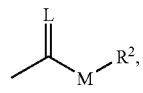
(c)

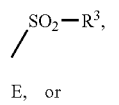
(d)

E, or
(f)

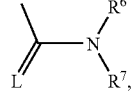
(g)

most preference is given to hydrogen, groups (b) and (c), in which

E represents a metal ion,
L represents oxygen and
M represents oxygen.

$R^1$ especially preferably represents $C_1$-$C_1$-alkyl,
  represents phenyl which is optionally monosubstituted by chlorine,
$R^2$ especially preferably represents $C_1$-$C_{10}$-alkyl or $C_2$-$C_{10}$-alkenyl,
$R^3$ especially preferably represents methyl.
$R^6$ and $R^7$ together especially preferably represent a $C_5$-$C_6$-alkylene radical in which optionally one methylene group is replaced by oxygen.

The general or preferred radical definitions or illustrations listed above can be combined with one another as desired, i.e. including combinations between the respective ranges and preferred ranges. They apply both to the end products and, correspondingly, to precursors and intermediates.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred. Special preference according to the invention is given to the compounds of the formula (I) which contain a combination of the meanings listed above as being especially preferred.

Saturated or unsaturated hydrocarbon radicals, such as alkyl, alkanediyl or alkenyl, can in each case be straight-chain or branched as far as this is possible, including in combination with heteroatoms, such as, for example, in alkoxy.

Unless indicated otherwise, optionally substituted radicals may be mono- or polysubstituted, where in the case of polysubstitutions the substituents may be identical or different.

In addition to the compounds mentioned in the Preparation Examples, the following compounds of the formula (I-1-a) may be specifically mentioned:

TABLE 1

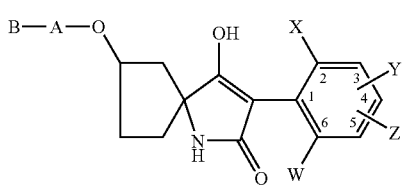

(I-1-a)

| A | B | X | W | Y | Z |
|---|---|---|---|---|---|
| $CH_2$ | H | $CH_3$ | H | H | H |
| $CH_2$ | H | Br | H | H | H |
| $CH_2$ | H | Cl | H | H | H |
| $CH_2$ | H | $CF_3$ | H | H | H |
| $CH_2$ | H | $OCH_3$ | H | H | H |
| $CH_2$ | H | $OC_2H_5$ | H | H | H |
| $CH_2$ | H | Br | H | 4-Cl | H |
| $CH_2$ | H | Cl | H | 4-Br | H |
| $CH_2$ | H | Cl | H | 4-Cl | H |
| $CH_2$ | H | Cl | H | 4-$CH_3$ | H |
| $CH_2$ | H | $CH_3$ | H | 4-Cl | H |
| $CH_2$ | H | $CH_3$ | H | 4-$CH_3$ | H |
| $CH_2$ | H | Cl | Cl | H | H |
| $CH_2$ | H | Cl | $OCH_3$ | H | H |
| $CH_2$ | H | Cl | $CH_3$ | H | H |
| $CH_2$ | H | Cl | $OC_2H_5$ | H | H |
| $CH_2$ | H | $OCH_3$ | $OCH_3$ | H | H |
| $CH_2$ | H | $CH_3$ | $CH_3$ | H | H |
| $CH_2$ | H | Br | $CH_3$ | 4-Br | H |
| $CH_2$ | H | Cl | Cl | 4-$CH_3$ | H |
| $CH_2$ | H | $CH_3$ | Br | 4-$CH_3$ | H |
| $CH_2$ | H | $CH_3$ | Cl | 4-$CH_3$ | H |
| $CH_2$ | H | $OCH_3$ | $CH_3$ | 4-$CH_3$ | H |
| $CH_2$ | H | $OC_2H_5$ | $CH_3$ | 4-$CH_3$ | H |
| $CH_2$ | H | $OC_3H_7$ | $CH_3$ | 4-$CH_3$ | H |
| $CH_2$ | H | $CH_3$ | $CH_3$ | 4-$CH_3$ | H |
| $CH_2$ | H | Br | Br | 4-$CH_3$ | H |
| $CH_2$ | H | $CH_3$ | $CH_3$ | 4-Br | H |
| $CH_2$ | H | $C_2H_5$ | $CH_3$ | H | H |
| $CH_2$ | H | $C_2H_5$ | $C_2H_5$ | H | H |
| $CH_2$ | H | $OCH_3$ | $C_2H_5$ | 4-$CH_3$ | H |
| $CH_2$ | H | $CH_3$ | $CH_3$ | 4-$OCH_3$ | H |
| $CH_2$ | H | Br | Cl | 4-$CH_3$ | H |
| $CH_2$ | H | Br | $CH_3$ | 4-Cl | H |
| $CH_2$ | H | Cl | $CH_3$ | 4-Br | H |
| $CH_2$ | H | $CH_3$ | $CH_3$ | 4-Cl | H |
| $CH_2$ | H | $C_2H_5$ | $CH_3$ | 4-$CH_3$ | H |
| $CH_2$ | H | $C_2H_5$ | $CH_3$ | 4-$C_2H_5$ | H |
| $CH_2$ | H | $C_2H_5$ | $C_2H_5$ | 4-$CH_3$ | H |
| $CH_2$ | H | $C_2H_5$ | $C_2H_5$ | 4-$C_2H_5$ | H |
| $CH_2$ | H | $C_2H_5$ | $CH_3$ | 4-Cl | H |
| $CH_2$ | H | $C_2H_5$ | $C_2H_5$ | 4-Cl | H |
| $CH_2$ | H | $C_2H_5$ | $CH_3$ | 4-Br | H |
| $CH_2$ | H | $C_2H_5$ | $C_2H_5$ | 4-Br | H |
| $CH_2$ | H | $C_2H_5$ | Cl | 4-$CH_3$ | H |
| $CH_2$ | H | $C_2H_5$ | Br | 4-$CH_3$ | H |
| $CH_2$ | H | $C_2H_5$ | Cl | 4-Cl | H |
| $CH_2$ | H | $C_2H_5$ | Br | 4-Br | H |
| $CH_2$ | H | $C_2H_5$ | Cl | 4-Br | H |
| $CH_2$ | H | $C_2H_5$ | Br | 4-Cl | H |
| $CH_2$ | H | $OCH_3$ | $CH_3$ | 4-Cl | H |
| $CH_2$ | H | $OCH_3$ | $C_2H_5$ | 4-Cl | H |
| $CH_2$ | H | $OC_2H_5$ | $CH_3$ | 4-Cl | H |
| $CH_2$ | H | $OC_2H_5$ | $C_2H_5$ | 4-Cl | H |
| $CH_2$ | H | Cl | $OCH_3$ | 4-$CH_3$ | H |
| $CH_2$ | H | Cl | $OC_2H_5$ | 4-$CH_3$ | H |
| $CH_2$ | H | Cl | Cl | 4-Cl | H |
| $CH_2$ | H | Cl | H | 4-Cl | 5-Cl |
| $CH_2$ | H | $CH_3$ | H | 4-$CH_3$ | 5-$CH_3$ |
| $CH_2$ | H | $CH_3$ | H | 4-Cl | 5-$CH_3$ |
| $CH_2$ | H | Br | H | 4-Cl | 5-$CH_3$ |
| $CH_2$ | H | Br | H | 4-$CH_3$ | 5-$CH_3$ |
| $CH_2$ | H | Cl | H | 4-Br | 5-$CH_3$ |
| $CH_2$ | H | Cl | H | 4-Cl | 5-$CH_3$ |
| $CH_2$ | H | $CH_3$ | H | 4-Br | 5-$CH_3$ |
| $CH_2$ | H | Cl | H | 4-$CH_3$ | 5-Cl |
| $CH_2$ | H | $CH_3$ | H | H | 5-$CH_3$ |
| $CH_2$ | H | Cl | H | H | 5-$CH_3$ |
| $CH_2$ | H | Br | H | H | 5-$CH_3$ |
| $CH_2$ | H | $CH_3$ | H | H | 5-Cl |
| $CH_2$ | H | $CH_3$ | H | H | 5-Br |
| $CH_2$ | H | $CH_3$ | $CH_3$ | 4-$CH_3$ | 5-$CH_3$ |
| $CH_2$ | H | $CH_3$ | $CH_3$ | 4-$CH_3$ | 5-Cl |
| $CH_2$ | H | $CH_3$ | $CH_3$ | 4-$CH_3$ | 5-Br |
| $CH_2$ | H | $CH_3$ | $CH_3$ | H | 3-Cl |
| $CH_2$ | H | $CH_3$ | $CH_3$ | H | 3-Br |
| $CH_2$ | H | Cl | Cl | H | 3-Br |

TABLE 1-continued (I-1-a)

B—A—O, OH, X, Y, Z structure with numbered positions 1-6, W, NH, O

| A | B | X | W | Y | Z |
|---|---|---|---|---|---|
| CH$_2$ | H | CH$_3$ | CH$_3$ | 4-(4-Cl-C$_6$H$_4$) | H |
| CH$_2$ | H | C$_2$H$_5$ | CH$_3$ | 4-(4-Cl-C$_6$H$_4$) | H |
| CH$_2$ | H | C$_2$H$_5$ | C$_2$H$_5$ | 4-(4-Cl-C$_6$H$_4$) | H |
| CH$_2$ | H | Cl | CH$_3$ | 4-(4-Cl-C$_6$H$_4$) | H |
| CH$_2$ | H | Cl | C$_2$H$_5$ | 4-(4-Cl-C$_6$H$_4$) | H |
| CH$_2$ | H | CH$_3$ | H | 5-(4-Cl-C$_6$H$_4$) | H |
| CH$_2$ | H | CH$_3$ | CH$_3$ | 5-(4-Cl-C$_6$H$_4$) | H |
| CH$_2$ | H | CH$_3$ | H | 5-(4-Cl-C$_6$H$_4$) | 4-CH$_3$ |
| CH$_2$ | H | CH$_3$ | CH$_3$ | 5-(4-Cl-C$_6$H$_4$) | 4-CH$_3$ |
| CH$_2$ | H | Cl | H | 5-(4-Cl-C$_6$H$_4$) | H |
| CH$_2$ | H | O—(CH$_2$)$_2$—OCH$_3$ | CH$_3$ | 4-Cl | H |
| CH$_2$ | H | O—(CH$_2$)$_2$—OCH$_3$ | C$_2$H$_5$ | 4-Cl | H |
| CH$_2$ | H | O—CH$_3$ | CH$_3$ | 4-Br | H |
| CH$_2$ | H | O—CH$_3$ | C$_2$H$_5$ | 4-Br | H |
| CH$_2$ | H | O—C$_2$H$_5$ | CH$_3$ | 4-Br | H |
| CH$_2$ | H | O—C$_2$H$_5$ | C$_2$H$_5$ | 4-Br | H |
| CH$_2$ | H | I | H | H | H |
| CH$_2$ | H | I | H | 4-CH$_3$ | H |
| CH$_2$ | H | I | CH$_3$ | H | H |
| CH$_2$ | H | I | C$_2$H$_5$ | H | H |
| CH$_2$ | H | CH$_3$ | H | H | 5-I |
| CH$_2$ | H | CH$_3$ | H | 4-CH$_3$ | 5-I |
| CH$_2$ | H | I | CH$_3$ | 4-CH$_3$ | H |
| CH$_2$ | H | I | C$_2$H$_5$ | 4-CH$_3$ | H |
| CH$_2$ | H | I | CH$_3$ | 4-Cl | H |
| CH$_2$ | H | I | C$_2$H$_5$ | 4-Cl | H |
| CH$_2$ | H | I | Cl | 4-CH$_3$ | H |
| CH$_2$ | H | I | H | 4-CH$_3$ | 5-CH$_3$ |
| CH$_2$ | H | CH$_3$ | H | 4-I | H |
| CH$_2$ | H | C$_2$H$_5$ | H | 4-I | H |
| CH$_2$ | H | CH$_3$ | CH$_3$ | 4-I | H |
| CH$_2$ | H | C$_2$H$_5$ | CH$_3$ | 4-I | H |
| CH$_2$ | H | C$_2$H$_5$ | C$_2$H$_5$ | 4-I | H |
| CH$_2$ | H | Cl | CH$_3$ | 4-I | H |
| CH$_2$ | H | Cl | C$_2$H$_5$ | 4-I | H |
| CH$_2$ | H | CH$_3$ | H | 4-I | 5-CH$_3$ |
| CH$_2$ | H | CH$_3$ | CH$_3$ | H | 3-I |
| CH$_2$ | H | I | H | H | 5-CH$_3$ |

Table 2: A, W, X, Y and Z as stated in Table 1
 B=CH$_3$
Table 3: A, W, X, Y and Z as stated in Table 1
 B=C$_2$H$_5$
Table 4: A, W, X, Y and Z as stated in Table 1
 B=C$_3$H$_7$
Table 5: A, W, X, Y and Z as stated in Table 1
 B=i-C$_3$H$_7$
Table 6: A, W, X, Y and Z as stated in Table 1

B = 

Table 7: A, W, X, Y and Z as stated in Table 1

B = 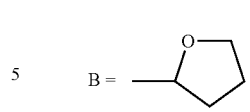

Table 8: A, W, X, Y and Z as stated in Table 1
 A=—CH$_2$—CH$_2$—; B=OCH$_3$
Table 9: A, W, X, Y and Z as stated in Table 1
 A=—CH$_2$—CH$_2$—; B=OC$_2$H$_5$ In addition to the compounds mentioned in the Preparation Examples, the following compounds of the formula (I-2-a) may be specifically mentioned:

TABLE 10

(I-2-a)

B—A—O, OH, X, Y, Z structure with numbered positions 1-6, W, O, O

| A | B | X | W | Y | Z |
|---|---|---|---|---|---|
| CH$_2$ | H | CH$_3$ | H | H | H |
| CH$_2$ | H | Br | H | H | H |
| CH$_2$ | H | Cl | H | H | H |
| CH$_2$ | H | CF$_3$ | H | H | H |
| CH$_2$ | H | OCH$_3$ | H | H | H |
| CH$_2$ | H | Br | H | 4-Cl | H |
| CH$_2$ | H | Cl | H | 4-Br | H |
| CH$_2$ | H | Cl | H | 4-Cl | H |
| CH$_2$ | H | Cl | H | 4-CH$_3$ | H |
| CH$_2$ | H | CH$_3$ | H | 4-Cl | H |
| CH$_2$ | H | CH$_3$ | H | 4-CH$_3$ | H |
| CH$_2$ | H | Cl | Cl | H | H |
| CH$_2$ | H | Cl | OCH$_3$ | H | H |
| CH$_2$ | H | Cl | CH$_3$ | H | H |
| CH$_2$ | H | Cl | OC$_2$H$_5$ | H | H |
| CH$_2$ | H | OCH$_3$ | OCH$_3$ | H | H |
| CH$_2$ | H | CH$_3$ | CH$_3$ | H | H |
| CH$_2$ | H | C$_2$H$_5$ | CH$_3$ | H | H |
| CH$_2$ | H | C$_2$H$_5$ | C$_2$H$_5$ | H | H |
| CH$_2$ | H | Br | CH$_3$ | 4-Br | H |
| CH$_2$ | H | Cl | Cl | 4-CH$_3$ | H |
| CH$_2$ | H | CH$_3$ | Br | 4-CH$_3$ | H |
| CH$_2$ | H | CH$_3$ | Cl | 4-CH$_3$ | H |
| CH$_2$ | H | OCH$_3$ | CH$_3$ | 4-CH$_3$ | H |
| CH$_2$ | H | OCH$_3$ | C$_2$H$_5$ | 4-CH$_3$ | H |
| CH$_2$ | H | OC$_2$H$_5$ | CH$_3$ | 4-CH$_3$ | H |
| CH$_2$ | H | OC$_3$H$_7$ | CH$_3$ | 4-CH$_3$ | H |
| CH$_2$ | H | CH$_3$ | CH$_3$ | 4-CH$_3$ | H |
| CH$_2$ | H | Br | Br | 4-CH$_3$ | H |
| CH$_2$ | H | Cl | Cl | 4-CH$_3$ | H |
| CH$_2$ | H | CH$_3$ | CH$_3$ | 4-Br | H |
| CH$_2$ | H | CH$_3$ | CH$_3$ | 4-OCH$_3$ | H |
| CH$_2$ | H | Br | Cl | 4-CH$_3$ | H |
| CH$_2$ | H | Br | CH$_3$ | 4-Cl | H |
| CH$_2$ | H | Cl | CH$_3$ | 4-Br | H |
| CH$_2$ | H | CH$_3$ | CH$_3$ | 4-Cl | H |
| CH$_2$ | H | C$_2$H$_5$ | CH$_3$ | 4-CH$_3$ | H |
| CH$_2$ | H | C$_2$H$_5$ | C$_2$H$_5$ | 4-CH$_3$ | H |
| CH$_2$ | H | C$_2$H$_5$ | CH$_3$ | 4-C$_2$H$_5$ | H |
| CH$_2$ | H | C$_2$H$_5$ | C$_2$H$_5$ | 4-C$_2$H$_5$ | H |
| CH$_2$ | H | C$_2$H$_5$ | CH$_3$ | 4-Cl | H |
| CH$_2$ | H | C$_2$H$_5$ | C$_2$H$_5$ | 4-Cl | H |
| CH$_2$ | H | C$_2$H$_5$ | CH$_3$ | 4-Br | H |
| CH$_2$ | H | C$_2$H$_5$ | C$_2$H$_5$ | 4-Br | H |
| CH$_2$ | H | C$_2$H$_5$ | Cl | 4-CH$_3$ | H |
| CH$_2$ | H | C$_2$H$_5$ | Br | 4-CH$_3$ | H |
| CH$_2$ | H | C$_2$H$_5$ | Cl | 4-Cl | H |
| CH$_2$ | H | C$_2$H$_5$ | Br | 4-Br | H |

TABLE 10-continued (I-2-a)

| A | B | X | W | Y | Z |
|---|---|---|---|---|---|
| CH₂ | H | C₂H₅ | Cl | 4-Br | H |
| CH₂ | H | C₂H₅ | Br | 4-Cl | H |
| CH₂ | H | OCH₃ | CH₃ | 4-Cl | H |
| CH₂ | H | OCH₃ | C₂H₅ | 4-Cl | H |
| CH₂ | H | OC₂H₅ | CH₃ | 4-Cl | H |
| CH₂ | H | OC₂H₅ | C₂H₅ | 4-Cl | H |
| CH₂ | H | Cl | OCH₃ | 4-CH₃ | H |
| CH₂ | H | Cl | OC₂H₅ | 4-CH₃ | H |
| CH₂ | H | CH₃ | CH₃ | 4-Cl | H |
| CH₂ | H | Cl | H | 4-Cl | 5-Cl |
| CH₂ | H | CH₃ | H | 4-CH₃ | 5-CH₃ |
| CH₂ | H | CH₃ | H | 4-Cl | 5-CH₃ |
| CH₂ | H | Br | H | 4-Cl | 5-CH₃ |
| CH₂ | H | Br | H | 4-CH₃ | 5-CH₃ |
| CH₂ | H | Cl | H | 4-Br | 5-CH₃ |
| CH₂ | H | Cl | H | 4-Cl | 5-CH₃ |
| CH₂ | H | CH₃ | H | 4-Br | 5-CH₃ |
| CH₂ | H | Cl | H | 4-CH₃ | 5-Cl |
| CH₂ | H | CH₃ | H | H | 5-CH₃ |
| CH₂ | H | Cl | H | H | 5-CH₃ |
| CH₂ | H | Br | H | H | 5-CH₃ |
| CH₂ | H | CH₃ | H | H | 5-Cl |
| CH₂ | H | CH₃ | H | H | 5-Br |
| CH₂ | H | CH₃ | CH₃ | 4-CH₃ | 5-CH₃ |
| CH₂ | H | CH₃ | CH₃ | 4-CH₃ | 5-Cl |
| CH₂ | H | CH₃ | CH₃ | 4-CH₃ | 5-Br |
| CH₂ | H | CH₃ | CH₃ | H | 3-Cl |
| CH₂ | H | CH₃ | CH₃ | H | 3-Br |
| CH₂ | H | Cl | Cl | H | 3-Br |
| CH₂ | H | CH₃ | CH₃ | 4-(4-Cl-C₆H₄) | H |
| CH₂ | H | C₂H₅ | CH₃ | 4-(4-Cl-C₆H₄) | H |
| CH₂ | H | C₂H₅ | C₂H₅ | 4-(4-Cl-C₆H₄) | H |
| CH₂ | H | Cl | CH₃ | 4-(4-Cl-C₆H₄) | H |
| CH₂ | H | Cl | C₂H₅ | 4-(4-Cl-C₆H₄) | H |
| CH₂ | H | CH₃ | H | 5-(4-Cl-C₆H₄) | H |
| CH₂ | H | CH₃ | CH₃ | 5-(4-Cl-C₆H₄) | H |
| CH₂ | H | CH₃ | H | 5-(4-Cl-C₆H₄) | 4-CH₃ |
| CH₂ | H | CH₃ | CH₃ | 5-(4-Cl-C₆H₄) | 4-CH₃ |
| CH₂ | H | Cl | H | 5-(4-Cl-C₆H₄) | H |
| CH₂ | H | I | H | H | H |
| CH₂ | H | I | H | 4-CH₃ | H |
| CH₂ | H | I | CH₃ | H | H |
| CH₂ | H | I | C₂H₅ | H | H |
| CH₂ | H | CH₃ | H | H | 5-I |
| CH₂ | H | CH₃ | H | 4-CH₃ | 5-I |
| CH₂ | H | I | CH₃ | 4-CH₃ | H |
| CH₂ | H | I | C₂H₅ | 4-CH₃ | H |
| CH₂ | H | I | CH₃ | 4-Cl | H |
| CH₂ | H | I | C₂H₅ | 4-Cl | H |
| CH₂ | H | I | Cl | 4-CH₃ | H |
| CH₂ | H | I | H | 4-CH₃ | 5-CH₃ |
| CH₂ | H | CH₃ | H | 4-I | H |
| CH₂ | H | C₂H₅ | H | 4-I | H |
| CH₂ | H | CH₃ | CH₃ | 4-I | H |
| CH₂ | H | C₂H₅ | CH₃ | 4-I | H |
| CH₂ | H | C₂H₅ | C₂H₅ | 4-I | H |
| CH₂ | H | Cl | CH₃ | 4-I | H |
| CH₂ | H | Cl | C₂H₅ | 4-I | H |
| CH₂ | H | CH₃ | H | 4-I | 5-CH₃ |
| CH₂ | H | CH₃ | CH₃ | H | 3-I |
| CH₂ | H | I | H | H | 5-CH₃ |

Table 11: A, W, X, Y and Z as stated in Table 10
B=CH₃
Table 12: A, W, X, Y and Z as stated in Table 10
B=C₂H₅
Table 13: A, W, X, Y and Z as stated in Table 10
B=C₃H₇
Table 14: A, W, X, Y and Z as stated in Table 10
B=i-C₃H₇
Table 15: A, W, X, Y and Z as stated in Table 10

B = ▷

Table 16: A, W, X, Y and Z as stated in Table 10

B = (tetrahydrofuran-2-yl)

Table 17: W, X, Y and Z as stated in Table 10
A=—CH₂—CH₂—; B=OCH₃
Table 18: W, X, Y and Z as stated in Table 10
A=—CH₂—CH₂—; B=OC₂H₅

Preferred definitions of the groups listed above in connection with the crop plant compatibility-improving compounds ("herbicide safeners") of the formulae (IIa), (IIb), (IIc), (IId) and (IIe) are defined below.

m preferably represents the numbers 0, 1, 2, 3 or 4.

A¹ preferably represents one of the divalent heterocyclic groupings shown below n preferably represents the numbers 0, 1, 2, 3 or 4.

A² preferably represents in each case optionally methyl-, ethyl-, methoxycarbonyl-, ethoxycarbonyl- or allyloxycarbonyl-substituted methylene or ethylene.

R¹⁴ preferably represents hydroxyl, mercapto, amino, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino.

R¹⁵ preferably represents hydroxyl, mercapto, amino, methoxy, ethoxy, n- or i-propoxy, n-, i-, s- or t-butoxy, 1-methylhexyloxy, allyloxy, 1-allyloxymethylethoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino.

$R^{16}$ preferably represents in each case optionally fluorine-, chlorine-, and/or bromine-substituted methyl, ethyl, n- or i-propyl.

$R^{17}$ preferably represents hydrogen, in each case optionally fluorine- and/or chlorine-substituted methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furyl-methyl, thienyl, thiazolyl, piperidinyl, or optionally fluorine-, chlorine-, methyl-, ethyl-, n- or i-propyl-, n-, i-, s- or t-butyl-substituted phenyl.

$R^{18}$ preferably represents hydrogen, in each case optionally fluorine- and/or chlorine-substituted methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furyl-methyl, thienyl, thiazolyl, piperidinyl, or optionally fluorine-, chlorine-, methyl-, ethyl-, n- or i-propyl-, n-, i-, s- or t-butyl-substituted phenyl, or together with $R^{17}$ represents one of the radicals —CH$_2$—O—CH$_2$—CH$_2$— and —CH$_2$—CH$_2$—O—CH$_2$—CH$_2$— which are optionally substituted by methyl, ethyl, furyl, phenyl, a fused benzene ring or by two substituents which, together with the C atom to which they are attached, form a 5- or 6-membered carbocycle.

$R^{19}$ preferably represents hydrogen, cyano, fluorine, chlorine, bromine, or represents in each case optionally fluorine-, chlorine- and/or bromine-substituted methyl, ethyl, n- or i-propyl, cyclopropyl, cyclobutyl, cyclopentyl, cyclohexyl or phenyl.

$R^{20}$ preferably represents hydrogen, in each case optionally hydroxyl-, cyano-, fluorine-, chlorine-, methoxy-, ethoxy-, n- or i-propoxy-substituted methyl, ethyl, n- or i-propyl, n-, i-, s- or t-butyl.

$R^{21}$ preferably represents hydrogen, cyano, fluorine, chlorine, bromine, or represents in each case optionally fluorine-, chlorine- and/or bromine-substituted methyl, ethyl, n- or i-propyl, n-, i-, s- or t-butyl, cyclopropyl, cyclobutyl, cyclopentyl, cyclohexyl or phenyl.

$X^1$ preferably represents nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

$X^2$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

$X^3$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

t preferably represents the numbers 0, 1, 2, 3 or 4.
v preferably represents the numbers 0, 1, 2, 3 or 4.

$R^{22}$ preferably represents hydrogen, methyl, ethyl, n- or i-propyl.

$R^{23}$ preferably represents hydrogen, methyl, ethyl, n- or i-propyl.

$R^{24}$ preferably represents hydrogen, in each case optionally cyano-, fluorine-, chlorine-, methoxy-, ethoxy-, n- or i-propoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino, or in each case optionally cyano-, fluorine-, chlorine-, bromine-, methyl-, ethyl-, n- or i-propyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino or cyclohexylamino.

$R^{25}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, or in each case optionally cyano-, fluorine-, chlorine-, bromine-, methyl-, ethyl-, n- or i-propyl-substituted cyclopropyl, cyclobutyl, cyclopentyl or cyclohexyl.

$R^{26}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, in each case optionally cyano-, fluorine-, chlorine-, bromine-, methyl-, ethyl-, n- or i-propyl-substituted cyclopropyl, cyclobutyl, cyclopentyl or cyclohexyl, or optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, or together with $R^{25}$ represents in each case optionally methyl- or ethyl-substituted butane-1,4-diyl (trimethylene), pentane-1,5-diyl, 1-oxabutane-1,4-diyl or 3-oxapentane-1,5-diyl.

$X^4$ preferably represents nitro, cyano, carboxyl, carbamoyl, formyl, sulfamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy.

$X^5$ preferably represents nitro, cyano, carboxyl, carbamoyl, formyl, sulfamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy.

Examples of the compounds of the formula (IIa) which are very particularly preferred as herbicide safeners according to the invention are listed in Table 19 below.

TABLE 19

(IIa)

Examples of the compounds of the formula (IIa)

| Example No. | (Positions) $(X^1)_m$ | $A^1$ | $R^{14}$ |
| --- | --- | --- | --- |
| IIa-1 | (2) Cl, (4) Cl | 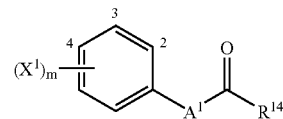 | OCH$_3$ |

TABLE 19-continued

Examples of the compounds of the formula (IIa)

| Example No. | (Positions) $(X^1)_m$ | $A^1$ | $R^{14}$ |
|---|---|---|---|
| IIa-2 | (2) Cl, (4) Cl | 1-methyl-3-methyl-5-(CH3)-pyrazoline-5-carboxylate ethyl ester | OCH3 |
| IIa-3 | (2) Cl, (4) Cl | 1-methyl-3-methyl-5-(CH3)-pyrazoline-5-carboxylate methyl ester | OC2H5 |
| IIa-4 | (2) Cl, (4) Cl | 1-methyl-3-methyl-5-(CH3)-pyrazoline-5-carboxylate ethyl ester | OC2H5 |
| IIa-5 | (2) Cl | 1-methyl-3-methyl-5-phenyl-pyrazole | OCH3 |
| IIa-6 | (2) Cl, (4) Cl | 1-methyl-3-methyl-5-phenyl-pyrazole | OCH3 |
| IIa-7 | (2) F | 1-methyl-3-methyl-5-phenyl-pyrazole | OCH3 |
| IIa-8 | (2) F | 1-methyl-3-methyl-5-(2-chlorophenyl)-pyrazole | OCH3 |
| IIa-9 | (2) Cl, (4) Cl | 1-methyl-3-methyl-5-CCl3-triazole | OC2H5 |
| IIa-10 | (2) Cl, (4) CF3 | 1-methyl-3-methyl-5-phenyl-triazole | OCH3 |
| IIa-11 | (2) Cl | 1-methyl-3-methyl-5-(2-fluorophenyl)-pyrazole | OCH3 |
| IIa-12 | — | 3-methyl-5-methyl-5-phenyl-isoxazoline | OC2H5 |
| IIa-13 | (2) Cl, (4) Cl | 1-methyl-3-methyl-5-CH3-pyrazole | OC2H5 |
| IIa-14 | (2) Cl, (4) Cl | 1-methyl-3-methyl-5-(i-C3H7)-pyrazole | OC2H5 |
| IIa-15 | (2) Cl, (4) Cl | 1-methyl-3-methyl-5-(t-C4H9)-pyrazole | OC2H5 |
| IIa-16 | (2) Cl, (4) Cl | 3-methyl-5-ethyl-isoxazoline | OC2H5 |
| IIa-17 | (2) Cl, (4) Cl | 3-methyl-5-methyl-isoxazoline | OC2H5 |

TABLE 19-continued

Examples of the compounds of the formula (IIa)

| Example No. | (Positions) $(X^1)_m$ | $A^1$ | $R^{14}$ |
|---|---|---|---|
| IIa-18 | — | 3-methyl-5-phenyl-4,5-dihydroisoxazol-5-yl | OH |

Examples of the compounds of the formula (IIb) which are very particularly preferred as herbicide safeners according to the invention are listed in Table 20 below.

TABLE 20

Examples of the compounds of the formula (IIb)

| Example No. | (Position) $X^2$ | (Position) $X^3$ | $A^2$ | $R^{15}$ |
|---|---|---|---|---|
| IIb-1 | (5) Cl | — | $CH_2$ | OH |
| IIb-2 | (5) Cl | — | $CH_2$ | $OCH_3$ |
| IIb-3 | (5) Cl | — | $CH_2$ | $OC_2H_5$ |
| IIb-4 | (5) Cl | — | $CH_2$ | $OC_3H_7$-n |
| IIb-5 | (5) Cl | — | $CH_2$ | $OC_3H_7$-i |
| IIb-6 | (5) Cl | — | $CH_2$ | $OC_4H_9$-n |
| IIb-7 | (5) Cl | — | $CH_2$ | $OCH(CH_3)$ $C_5H_{11}$-n |
| IIb-8 | (5) Cl | (2) F | $CH_2$ | OH |
| IIb-9 | (5) Cl | (2) Cl | $CH_2$ | OH |
| IIb-10 | (5) Cl | — | $CH_2$ | $OCH_2CH=CH_2$ |
| IIb-11 | (5) Cl | — | $CH_2$ | $OC_4H_9$-i |
| IIb-12 | (5) Cl | — | $CH_2$ | (1,3-dioxolan-2-yl)methoxy / acetal ether group |
| IIb-13 | (5) Cl | — | $=CH_2$ (on CH) | $OCH_2CH=CH_2$ |
| IIb-14 | (5) Cl | — | $C_2H_5$ | $OC_2H_5$ |
| IIb-15 | (5) Cl | — | $CH_3$ | $OCH_3$ |

Examples of the compounds of the formula (IIc) which are very particularly preferred as herbicide safeners according to the invention are listed in Table 21 below.

TABLE 21

Examples of the compounds of the formula (IIc)

| Example No. | $R^{16}$ | $N(R^{17}, R^{18})$ |
|---|---|---|
| IIc-1 | $CHCl_2$ | $N(CH_2CH=CH_2)_2$ |
| IIc-2 | $CHCl_2$ | 2,2,3-trimethyl-1,3-oxazolidin-3-yl |
| IIc-3 | $CHCl_2$ | 2,2,5-trimethyl-1,3-oxazolidin-3-yl |

TABLE 21-continued (IIc)

Examples of the compounds of the formula (IIc)

| Example No. | $R^{16}$ | $N(R^{17}, R^{18})$ |
|---|---|---|
| IIc-4 | $CHCl_2$ | (N-methyl-1-oxa-4-azaspiro[4.5]decane) |
| IIc-5 | $CHCl_2$ | (3,2,2-trimethyl-5-phenyl-oxazolidine) |
| IIc-6 | $CHCl_2$ | (3,4-dimethyl-3,4-dihydro-2H-1,4-benzoxazine) |
| IIc-7 | $CHCl_2$ | (3,2,2-trimethyl-5-(furan-2-yl)-oxazolidine) |

Examples of the compounds of the formula (IId) which are very particularly preferred as herbicide safeners according to the invention are listed in Table 22 below.

TABLE 22

(IId)

Examples of the compounds of the formula (IId)

| Example No. | $R^{22}$ | $R^{23}$ | $R^{24}$ | (Positions) $(X^4)_t$ | (Positions) $(X^5)_y$ |
|---|---|---|---|---|---|
| IId-1 | H | H | $CH_3$ | (2) $OCH_3$ | — |
| IId-2 | H | H | $C_2H_5$ | (2) $OCH_3$ | — |
| IId-3 | H | H | $C_3H_7$-n | (2) $OCH_3$ | — |
| IId-4 | H | H | $C_3H_7$-i | (2) $OCH_3$ | — |
| IId-5 | H | H | cyclopropyl | (2) $OCH_3$ | — |
| IId-6 | H | H | $CH_3$ | (2) $OCH_3$ | (5) $CH_3$ |
| IId-7 | H | H | $C_2H_5$ | (2) $OCH_3$ | (5) $CH_3$ |
| IId-8 | H | H | $C_3H_7$-n | (2) $OCH_3$ | (5) $CH_3$ |
| IId-9 | H | H | $C_3H_7$-i | (2) $OCH_3$ | (5) $CH_3$ |
| IId-10 | H | H | cyclopropyl | (2) $OCH_3$ | (5) $CH_3$ |
| IId-11 | H | H | $OCH_3$ | (2) $OCH_3$ | (5) $CH_3$ |
| IId-12 | H | H | $OC_2H_5$ | (2) $OCH_3$ | (5) $CH_3$ |
| IId-13 | H | H | $OC_3H_{7\text{-}i}$ | (2) $OCH_3$ | (5) $CH_3$ |
| IId-14 | H | H | $SCH_3$ | (2) $OCH_3$ | (5) $CH_3$ |
| IId-15 | H | H | $SC_2H_5$ | (2) $OCH_3$ | (5) $CH_3$ |
| IId-16 | H | H | $SC_3H_7$-i | (2) $OCH_3$ | (5) $CH_3$ |
| IId-17 | H | H | $NHCH_3$ | (2) $OCH_3$ | (5) $CH_3$ |
| IId-18 | H | H | $NHC_2H_5$ | (2) $OCH_3$ | (5) $CH_3$ |
| IId-19 | H | H | $NHC_3H_7$-i | (2) $OCH_3$ | (5) $CH_3$ |
| IId-20 | H | H | N-methyl-cyclopropylamino | (2) $OCH_3$ | (5) $CH_3$ |
| IId-21 | H | H | $NHCH_3$ | (2) $OCH_3$ | — |
| IId-22 | H | H | $NHC_3H_7$-i | (2) $OCH_3$ | — |
| IId-23 | H | H | $N(CH_3)_2$ | (2) $OCH_3$ | — |
| IId-24 | H | H | $N(CH_3)_2$ | (3) $CH_3$ (4) $CH_3$ | — |
| IId-25 | H | H | $CH_2$—O—$CH_3$ | (2) $OCH_3$ | — |

Examples of the compounds of the formula (IIe) which are very particularly preferred as herbicide safeners according to the invention are listed in Table 23 below.

TABLE 23

(IIe)

Examples of the compounds of the formula (IIe)

| Example No. | $R^{22}$ | $R^{25}$ | $R^{26}$ | (Positions) $(X^4)_t$ | (Positions) $(X^5)_v$ |
|---|---|---|---|---|---|
| IIe-1 | H | H | $CH_3$ | (2) $OCH_3$ | — |
| IIe-2 | H | H | $C_2H_5$ | (2) $OCH_3$ | — |
| IIe-3 | H | H | $C_3H_7$-n | (2) $OCH_3$ | — |
| IIe-4 | H | H | $C_3H_7$-i | (2) $OCH_3$ | — |
| IIe-5 | H | H | cyclopropyl | (2) $OCH_3$ | — |
| IIe-6 | H | $CH_3$ | $CH_3$ | (2) $OCH_3$ | — |
| IIe-7 | H | H | $CH_3$ | (2) $OCH_3$ (5) $CH_3$ | — |
| IIe-8 | H | H | $C_2H_5$ | (2) $OCH_3$ (5) $CH_3$ | — |
| IIe-9 | H | H | $C_3H_7$-n | (2) $OCH_3$ (5) $CH_3$ | — |
| IIe-10 | H | H | $C_3H_7$-i | (2) $OCH_3$ (5) $CH_3$ | — |
| IIe-11 | H | H | cyclopropyl | (2) $OCH_3$ (5) $CH_3$ | — |
| IIe-12 | H | $CH_3$ | $CH_3$ | (2) $OCH_3$ (5) $CH_3$ | — |

Most preferred as crop plant compatibility-improving compound [component (b')] are cloquintocet-mexyl, fenchlorazole-ethyl, isoxadifen-ethyl, mefenpyr-diethyl, furilazole, fenclorim, cumyluron, dymron, dimepiperate and the compounds IIe-5 (cyprosulfamide) and IIe-11, and particular emphasis is given to cloquintocet-mexyl and mefenpyr-diethyl, and also isoxadifen-ethyl sand cyprosulfamide.

The compounds of the general formula (IIa) to be used as safeners according to the invention are known and/or can be prepared by processes known per se (cf. WO-A-91/07874, WO-A-95/07897).

The compounds of the general formula (IIb) to be used as safeners according to the invention are known and/or can be prepared by processes known per se (cf. EP-A-191736).

The compounds of the general formula (IIc) to be used as safeners according to the invention are known and/or can be prepared by processes known per se (cf. DE-A-2218097, DE-A-2350547).

The compounds of the general formula (IId) to be used as safeners according to the invention are known and/or can be prepared by processes known per se (cf. DE-A-19621522/ U.S. Pat. No. 6,235,680).

The compounds of the general formula (IIe) to be used as safeners according to the invention are known and can be prepared by processes known per se (cf. WO-A-99/66795/ U.S. Pat. No. 6,251,827).

Examples of the selective herbicidal combinations according to the invention comprising in each case one active compound of the formula (I) and one of the safeners defined above are listed in Table 24 below.

TABLE 24

Examples of combinations according to the invention

| Active compounds of the formula (I) | Safener |
|---|---|
| I-1-a | cloquintocet-mexyl |
| I-1-a | fenchlorazole-ethyl |
| I-1-a | isoxadifen-ethyl |
| I-1-a | mefenpyr-diethyl |
| I-1-a | furilazole |
| I-1-a | fenclorim |
| I-1-a | cumyluron |
| I-1-a | daimuron/dymron |
| I-1-a | dimepiperate |
| I-1-a | IIe-11 |
| I-1-a | IIe-5 |
| I-1-b | cloquintocet-mexyl |
| I-1-b | fenchlorazole-ethyl |
| I-1-b | isoxadifen-ethyl |
| I-1-b | mefenpyr-diethyl |
| I-1-b | furilazole |
| I-1-b | fenclorim |
| I-1-b | cumyluron |
| I-1-b | daimuron/dymron |
| I-1-b | dimepiperate |
| I-1-b | IIe-11 |
| I-1-b | IIe-5 |
| I-1-c | cloquintocet-mexyl |
| I-1-c | fenchlorazole-ethyl |
| I-1-c | isoxadifen-ethyl |
| I-1-c | mefenpyr-diethyl |
| I-1-c | furilazole |
| I-1-c | fenclorim |
| I-1-c | cumyluron |
| I-1-c | daimuron/dymron |
| I-1-c | dimepiperate |
| I-1-c | IIe-5 |
| I-1-c | IIe-11 |
| I-1-d | cloquintocet-mexyl |
| I-1-d | fenchlorazole-ethyl |
| I-1-d | isoxadifen-ethyl |
| I-1-d | mefenpyr-diethyl |
| I-1-d | furilazole |
| I-1-d | fenclorim |
| I-1-d | cumyluron |
| I-1-d | daimuron/dymron |
| I-1-d | dimepiperate |
| I-1-d | IIe-11 |
| I-1-d | IIe-5 |
| I-1-e | cloquintocet-mexyl |
| I-1-e | fenchlorazole-ethyl |
| I-1-e | isoxadifen-ethyl |
| I-1-e | mefenpyr-diethyl |
| I-1-e | furilazole |
| I-1-e | fenclorim |
| I-1-e | cumyluron |
| I-1-e | daimuron/dymron |
| I-1-e | dimepiperate |
| I-1-e | IIe-5 |
| I-1-e | IIe-11 |
| I-1-f | cloquintocet-mexyl |
| I-1-f | fenchlorazole-ethyl |
| I-1-f | isoxadifen-ethyl |
| I-1-f | mefenpyr-diethyl |
| I-1-f | furilazole |
| I-1-f | fenclorim |
| I-1-f | cumyluron |
| I-1-f | daimuron/dymron |
| I-1-f | dimepiperate |
| I-1-f | IIe-5 |
| I-1-f | IIe-11 |
| I-1-g | cloquintocet-mexyl |
| I-1-g | fenchlorazole-ethyl |
| I-1-g | isoxadifen-ethyl |
| I-1-g | mefenpyr-diethyl |
| I-1-g | furilazole |
| I-1-g | fenclorim |
| I-1-g | cumyluron |
| I-1-g | daimuron/dymron |
| I-1-g | dimepiperate |

TABLE 24-continued

Examples of combinations according to the invention

| Active compounds of the formula (I) | Safener |
|---|---|
| I-1-g | IIe-5 |
| I-1-g | IIe-11 |

TABLE 25

Examples of combinations according to the invention

| Active compounds of the formula (I) | Safener |
|---|---|
| I-2-a | cloquintocet-mexyl |
| I-2-a | fenchlorazole-ethyl |
| I-2-a | isoxadifen-ethyl |
| I-2-a | mefenpyr-diethyl |
| I-2-a | furilazole |
| I-2-a | fenclorim |
| I-2-a | cumyluron |
| I-2-a | daimuron/dymron |
| I-2-a | dimepiperate |
| I-2-a | IIe-11 |
| I-2-a | IIe-5 |
| I-2-b | cloquintocet-mexyl |
| I-2-b | fenchlorazole-ethyl |
| I-2-b | isoxadifen-ethyl |
| I-2-b | mefenpyr-diethyl |
| I-2-b | furilazole |
| I-2-b | fenclorim |
| I-2-b | cumyluron |
| I-2-b | daimuron/dymron |
| I-2-b | dimepiperate |
| I-2-b | IIe-11 |
| I-2-b | IIe-5 |
| I-2-c | cloquintocet-mexyl |
| I-2-c | fenchlorazole-ethyl |
| I-2-c | isoxadifen-ethyl |
| I-2-c | mefenpyr-diethyl |
| I-2-c | furilazole |
| I-2-c | fenclorim |
| I-2-c | cumyluron |
| I-2-c | daimuron/dymron |
| I-2-c | dimepiperate |
| I-2-c | IIe-5 |
| I-2-c | IIe-11 |
| I-2-d | cloquintocet-mexyl |
| I-2-d | fenchlorazole-ethyl |
| I-2-d | isoxadifen-ethyl |
| I-2-d | mefenpyr-diethyl |
| I-2-d | furilazole |
| I-2-d | fenclorim |
| I-2-d | cumyluron |
| I-2-d | daimuron/dymron |
| I-2-d | dimepiperate |
| I-2-d | IIe-11 |
| I-2-d | IIe-5 |
| I-2-e | cloquintocet-mexyl |
| I-2-e | fenchlorazole-ethyl |
| I-2-e | isoxadifen-ethyl |
| I-2-e | mefenpyr-diethyl |
| I-2-e | furilazole |
| I-2-e | fenclorim |
| I-2-e | cumyluron |
| I-2-e | daimuron/dymron |
| I-2-e | dimepiperate |
| I-2-e | IIe-5 |
| I-2-e | IIe-11 |
| I-2-f | cloquintocet-mexyl |
| I-2-f | fenchlorazole-ethyl |
| I-2-f | isoxadifen-ethyl |
| I-2-f | mefenpyr-diethyl |
| I-2-f | furilazole |
| I-2-f | fenclorim |
| I-2-f | cumyluron |
| I-2-f | daimuron/dymron |
| I-2-f | dimepiperate |
| I-2-f | IIe-5 |
| I-2-f | IIe-11 |
| I-2-g | cloquintocet-mexyl |
| I-2-g | fenchlorazole-ethyl |
| I-2-g | isoxadifen-ethyl |
| I-2-g | mefenpyr-diethyl |
| I-2-g | furilazole |
| I-2-g | fenclorim |
| I-2-g | cumyluron |
| I-2-g | daimuron/dymron |
| I-2-g | dimepiperate |
| I-2-g | IIe-5 |
| I-2-g | IIe-11 |

Surprisingly, it has now been found that the active compound combinations, defined above, of substituted cyclic ketoenols of the general formula (I) and safeners (antidotes) from group (b') listed above, whilst being very well tolerated by useful plants, have a particularly high herbicidal activity and can be used in various crops, in particular in cereals (especially wheat), but also in soya beans, potatoes, maize and rice, for the selective control of weeds.

Here, it has to be considered surprising that, from a large number of known safeners or antidotes capable of antagonizing the harmful effect of a herbicide on crop plants, those suitable are in particular the compounds of group (b') listed above which eliminate the harmful effect of substituted cyclic ketoenols on the crop plants virtually completely without having a major adverse effect on the herbicidal activity against the weeds.

Emphasis may be given here to the particularly advantageous effect of the particularly and most preferred combination partners from group (b'), in particular with respect to sparing cereal plants, such as, for example, wheat, barley and rye, but also maize and rice, as crop plants.

In the literature it has already been described how the action of various active compounds can be boosted by addition of ammonium salts. The salts in question, however, are detersive salts (e.g. WO 95/017817) or salts which have relatively long alkyl substituents and/or aryl substituents and which have a permeabilizing action or which increase the active compound's solubility (e.g. EP-A 0 453 086, EP-A 0 664 081, FR-A 2 600 494, U.S. Pat. No. 4,844,734, U.S. Pat. No. 5,462,912, U.S. Pat. No. 5,538,937, US-A 03/0224939, US-A 05/0009880, US-A 05/0096386). Moreover, the prior art describes the action only for particular active compounds and/or particular applications of the corresponding compositions. In other cases, in turn, the salts in question are those of sulfonic acids, where the acids themselves have a paralytic action on insects (U.S. Pat. No. 2,842,476). A boost to action by ammonium sulfate, for example, is described by way of example for the herbicides glyphosate and phosphinothricin (U.S. Pat. No. 6,645,914, EP-A2 0 036 106). A corresponding action in the case of insecticides is neither disclosed nor suggested by this prior art.

The use of ammonium sulfate as a formulating assistant has also been described for certain active compounds and applications (WO 92/16108), but its purpose therein is to stabilize the formulation, not to boost the action.

It has now been found, entirely surprisingly, that the action of insecticides and/or acaricides and/or herbicides from the class of the 3'-alkoxyspirocyclopentyl-substituted tetramic and tetronic acids can be boosted significantly through the addition of ammonium salts or phosphonium salts to the application solution or through the incorporation of these salts into a formulation comprising 3'-alkoxyspirocyclopentyl-substituted. The present invention therefore provides for the use of ammonium salts or phosphonium salts for boosting the action of crop protection compositions which comprise as their active compound tetramic and tetronic acids insecticidal and/or acaricidal 3'-alkoxyspirocyclopentyl-substituted tetramic and tetronic acids. The invention likewise provides compositions which comprise insecticidal 3'-alkoxyspirocyclopentyl-substituted tetramic and tetronic acids and action-boosting ammonium salts or phosphonium salts, including not only formulated active compounds but also ready-to-use compositions (spray liquors). The invention further provides, finally, for the use of these compositions for controlling insect pests and/or spider mites and/or unwanted vegetation. These compositions may also comprise the crop plant compatibility-improving compounds mentioned above.

The active compounds can be used in the compositions of the invention in a broad concentration range. The concentration of the active compounds in the formulation is typically 0.1%-50% by weight.

Ammonium salts and phosphonium salts which inventively boost the activity of crop protection compositions comprising fatty acid biosynthesis inhibitors are defined by formula (III')

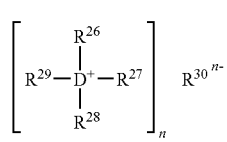

(III')

in which
D represents nitrogen or phosphorus,
D preferably represents nitrogen,
$R^{26}$, $R^{27}$, $R^{28}$ and $R^{29}$ independently of one another represent hydrogen or in each case optionally substituted $C_1$-$C_8$-alkyl or mono- or polyunsaturated, optionally substituted $C_1$-$C_8$-alkylene, the substituents being selectable from halogen, nitro and cyano,
$R^{26}$, $R^{27}$, $R^{28}$ and $R^{29}$ independently of one another preferably represent hydrogen or in each case optionally substituted $C_1$-$C_4$-alkyl, the substituents being selectable from halogen, nitro and cyano,
$R^{26}$, $R^{27}$, $R^{28}$ and $R^{29}$ independently of one another particularly preferably represent hydrogen, methyl, ethyl, n-propyl, isopropyl, n-butyl, isobutyl, sec-butyl or tert-butyl,
$R^{26}$, $R^{27}$, $R^{28}$ and $R^{29}$ very particularly preferably represent hydrogen,
n represents 1, 2, 3 or 4,
n preferably represents 1 or 2,
$R^{30}$ represents an organic or inorganic anion,
$R^{30}$ preferably represents hydrogencarbonate, tetraborate, fluoride, bromide, iodide, chloride, monohydrogenphosphate, dihydrogenphosphate, hydrogensulfate, tartrate, sulfate, nitrate, thiosulfate, thiocyanate, formate, lactate, acetate, propionate, butyrate, pentanoate or oxalate,
$R^{30}$ particularly preferably represents lactate, sulfate, nitrate, thiosulfate, thiocyanate, oxalate or formate.
$R^{30}$ very particularly preferably represents sulfate.

The ammonium salts and phosphonium salts of the formula (III') can be used in a broad concentration range to boost the activity of crop protection compositions comprising ketoenols. In general the ammonium salts or phosphonium salts are used in the ready-to-use crop protection composition in a concentration of 0.5 to 80 mmol/l, preferably 0.75 to 37.5 mmol/l, more preferably 1.5 to 25 mmol/l. In the case of a formulated product the ammonium salt and/or phosphonium salt concentration in the formulation is chosen such that it is within these stated general, preferred or particularly preferred ranges after the formulation has been diluted to the desired active-ingredient concentration. The concentration of the salt in the formulation is typically 1%-50% by weight.

In one preferred embodiment of the invention the activity is boosted by adding to the crop protection compositions not only an ammonium salt and/or phosphonium salt but also, additionally, a penetrant. It is considered entirely surprising that even in these cases an even greater boost to activity is observed. The present invention therefore likewise provides for the use of a combination of penetrant and ammonium salts and/or phosphonium salts to boost the activity of crop protection compositions which comprise insecticidal 3'-alkoxyspirocyclopentyl-substituted tetramic and tetronic acids as active compound. The invention likewise provides compositions which comprise herbicidal and/or acaricidal and/or insecticidal 3'-alkoxyspirocyclopentyl-substituted tetramic and tetronic acids, penetrants and ammonium salts and/or phosphonium salts, including specifically not only formulated active compounds but also ready-to-use compositions (spray liquors). The invention additionally provides, finally, for the use of these compositions for controlling insect pests.

Suitable penetrants in the present context include all those substances which are typically used to enhance the penetration of active agrochemical compounds into plants. Penetrants are defined in this context by their ability to penetrate from the aqueous spray liquor and/or from the spray coating into the cuticle of the plant and thereby to increase the mobility of active compounds in the cuticle. The method described in the literature (Baur et al., 1997, Pesticide Science 51, 131-152) can be used in order to determine this property.

Examples of suitable penetrants include alkanol alkoxylates. Penetrants of the invention are alkanol alkoxylates of the formula (IV')

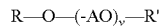

(IV')

in which
R represents straight-chain or branched alkyl having 4 to 20 carbon atoms,
R' represents hydrogen, methyl, ethyl, n-propyl, isopropyl, n-butyl, isobutyl, tert-butyl, n-pentyl or n-hexyl,
AO represents an ethylene oxide radical, a propylene oxide radical, a butylene oxide radical or is mixtures of ethylene oxide and propylene oxide radicals or butylene oxide radicals, and
v represents a number from 2 to 30.

One preferred group of penetrants are alkanol alkoxylates of the formula

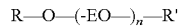

(IV'-a)

in which
R is as defined above,
R' is as defined above,
EO represents —$CH_2$—$CH_2$—O—, and
n represents a number from 2 to 20.

A further preferred group of penetrants are alkanol alkoxylates of the formula

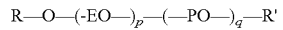

(IV'-b)

in which
R is as defined above,
R' is as defined above,
EO represents —CH$_2$—CH$_2$—O—,
PO represents

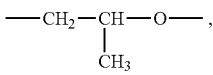

p represents a number from 1 to 10, and
q represents a number from 1 to 10.

A further preferred group of penetrants are alkanol alkoxylates of the formula

R—O—(—PO—)$_r$-(EO—)$_s$—R' (IV'-c)

in which
R is as defined above,
R' is as defined above,
EO represents —CH$_2$—CH$_2$—O—,
PO represents

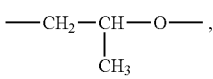

r represents a number from 1 to 10, and
s represents a number from 1 to 10.

A further preferred group of penetrants are alkanol alkoxylates of the formula

R—O—(-EO—)$_p$—(—BO—)$_q$—R' (IV'-d)

in which
R and R' are as defined above,
EO represents CH$_2$—CH$_2$—O—,
BO represents

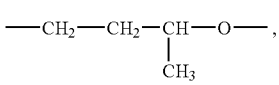

p represents a number from 1 to 10 and
q represents a number from 1 to 10.

A further preferred group of penetrants are alkanol alkoxylates of the formula

R—O—(—BO—)$_r$—(-EO—)$_s$—R' (IV'-e)

in which
R and R' are as defined above,
BO represents

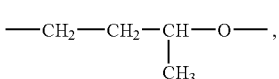

EO represents CH$_2$—CH$_2$—O—,
r represents a number from 1 to 10 and
s represents a number from 1 to 10.

A further preferred group of penetrants are alkanol alkoxylates of the formula

CH$_3$—(CH$_2$)$_t$—CH$_2$—O—(—CH$_2$—CH$_2$—O—)$_u$—R' (IV'-f)

in which
R' is as defined above,
t represents a number from 8 to 13,
u represents a number from 6 to 17.

In the formulae indicated above,
R preferably represents butyl, isobutyl, n-pentyl, isopentyl, neopentyl, n-hexyl, isohexyl, n-octyl, isooctyl, 2-ethylhexyl, nonyl, isononyl, decyl, n-dodecyl, isododecyl, lauryl, myristyl, isotridecyl, trimethylnonyl, palmityl, stearyl or eicosyl.

As an example of an alkanol alkoxylate of the formula (IV'-c) mention may be made of 2-ethylhexyl alkoxylate of the formula

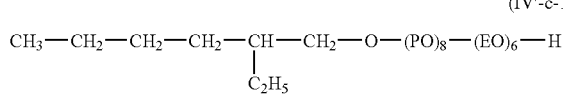

in which
EO represents —CH$_2$—CH$_2$—O—,
PO represents and

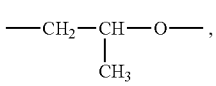

the numbers 8 and 6 represent average values.

As an example of an alkanol alkoxylate of the formula (IV'-d) mention may be made of the formula CH$_3$—(CH$_2$)$_{10}$—O—(-EO—)$_6$—(—BO—)$_2$—CH$_3$ (IV'-d-1)

in which
EO represents CH$_2$—CH$_2$—O—,
BO represents

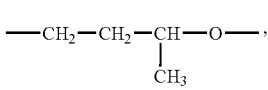

the numbers 10, 6 and 2 represent average values.

Particularly preferred alkanol alkoxylates of the formula (IV'-f) are compounds of this formula in which
t represents a number from 9 to 12 and
u represents a number from 7 to 9.

Mention may be made with very particular preference of alkanol alkoxylate of the formula (IV'-f-1)

CH$_3$—(CH$_2$)$_t$—CH$_2$—O—(—CH$_2$—CH$_2$—O—)$_u$—H (IV'-f-1)

in which
t stands for the average value 10.5 and
u stands for the average value 8.4.

A general definition of the alkanol alkoxylates is given by the formulae above. These substances are mixtures of compounds of the stated type with different chain lengths. The indices therefore have average values which may also deviate from whole numbers.

The alkanol alkoxylates of the formulae stated are known and in some cases are available commercially or can be prepared by known methods (cf. WO 98/35 553, WO 00/35 278 and EP-A 0 681 865).

Suitable penetrants also include, for example, substances which promote the availability of the compounds of the formula (I) in the spray coating. These include, for example, mineral or vegetable oils. Suitable oils are all mineral or vegetable oils—modified or otherwise—which can typically be used in agrochemical compositions. Mention may be made by way of example of sunflower oil, rapeseed oil, olive oil, castor oil, colza oil, maize seed oil, cotton seed oil and soybean oil, or the esters of said oils. Preference is given to rapeseed oil, sunflower oil and their methyl or ethyl esters.

The concentration of penetrant in the compositions of the invention can be varied within a wide range. In the case of a formulated crop protection composition it is in general 1% to 95%, preferably 1% to 55%, more preferably 15%-40% by weight. In the ready-to-use compositions (spray liquors) the concentrations are generally between 0.1 and 10 g/l, preferably between 0.5 and 5 μl.

Crop protection compositions of the invention may also comprise further components, examples being surfactants and/or dispersing assistants or emulsifiers.

Suitable nonionic surfactants and/or dispersing assistants include all substances of this type that can typically be used in agrochemical compositions. Preferably mention may be made of polyethylene oxide-polypropylene oxide block copolymers, polyethylene glycol ethers of linear alcohols, reaction products of fatty acids with ethylene oxide and/or propylene oxide, and also polyvinyl alcohol, polyvinylpyrrolidone, copolymers of polyvinyl alcohol and polyvinylpyrrolidone, and copolymers of (meth)acrylic acid and (meth)acrylic esters, and additionally alkyl ethoxylates and alkylaryl ethoxylates, which optionally may be phosphated and optionally may be neutralized with bases, mention being made, by way of example, of sorbitol ethoxylates, and, as well, polyoxyalkylenamine derivatives.

Suitable anionic surfactants include all substances of this type that can typically be used in agrochemical compositions. Preference is given to alkali metal salts and alkaline earth metal salts of alkylsulfonic acids or alkylarylsulfonic acids.

A further preferred group of anionic surfactants and/or dispersing assistants are the following salts that are of low solubility in plant oil: salts of polystyrenesulfonic acids, salts of polyvinylsulfonic acids, salts of naphthalenesulfonic acid-formaldehyde condensation products, salts of condensation products of naphthalenesulfonic acid, phenolsulfonic acid and formaldehyde, and salts of lignosulfonic acid.

Suitable additives which may be included in the formulations of the invention are emulsifiers, foam inhibitors, preservatives, antioxidants, colorants and inert filling materials.

Preferred emulsifiers are ethoxylated nonylphenols, reaction products of alkylphenols with ethylene oxide and/or propylene oxide, ethoxylated arylalkylphenols, and also ethoxylated and propoxylated arylalkylphenols, and also sulfated or phosphated arylalkyl ethoxylates and/or arylalkyl ethoxypropoxylates, mention being made by way of example of sorbitan derivatives, such as polyethylene oxide-sorbitan fatty acid esters, and sorbitan fatty acid esters.

Using, for example, according to process (A) ethyl N-[(4-chloro-2,6-dimethyl)phenylacetyl]-1-amino-3-methoxycyclopentanecarboxylate as starting material, the course of the process of the invention can be represented by the following reaction scheme:

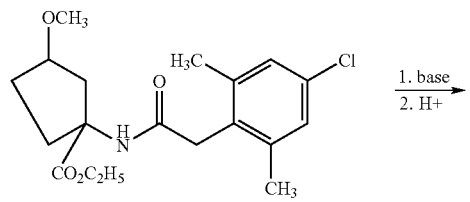

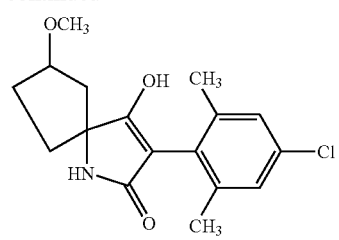

Using, for example, according to process (B) ethyl 0-[(2-chloro-6-methyl)phenylacetyl]-1-hydroxy-3-ethoxycyclopentanecarboxylate, the course of the process of the invention can be represented by the following reaction scheme:

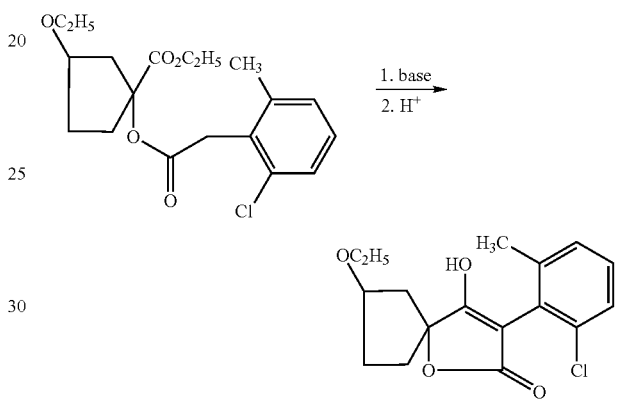

Using, for example, according to process (Cα) 7-butoxy-3-[(4-chloro-2,6-dimethyl)phenyl]-1-azaspiro[4,4]nonane-2,4-dione and pivaloyl chloride as starting materials, the course of the process of the invention can be represented by the following reaction scheme:

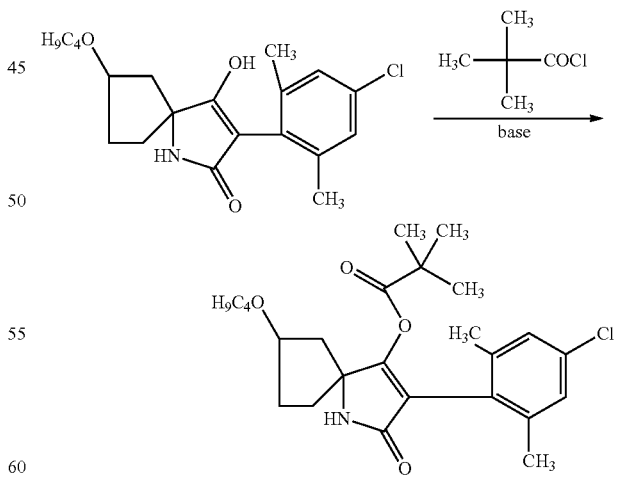

Using, for example, according to process (C) (variant β) 7-ethoxy-3-[(2,4-dichloro)phenyl]-1-oxaspiro-[4,4]-nonane-2,4-dione and acetic anhydride as starting compounds, the course of the process of the invention can be represented by the following reaction scheme:

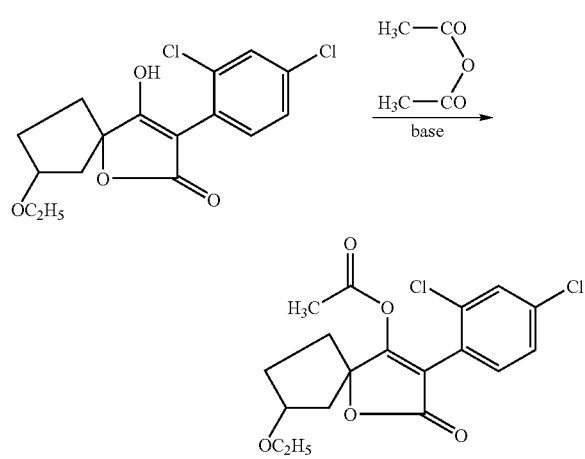

Using, for example, according to process (D) 7-methoxy-3-[(2,4-dichlor-6-methyl)-phenyl]-1-azaspiro[4,4]nonane-2,4-dione and ethyl chloroformate as starting materials, the course of the process of the invention can be represented by the following reaction scheme:

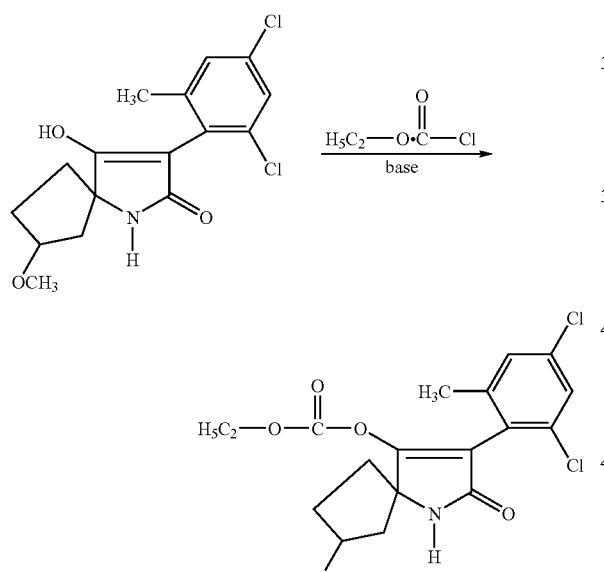

Using, for example, according to process (E) 7-ethoxy-3-[(2,4,6-trimethyl)phenyl]-1-oxa-spiro[4,4]nonane-2,4-dione and methyl chloromonothioformate as starting materials, the course of the reaction can be represented as follows:

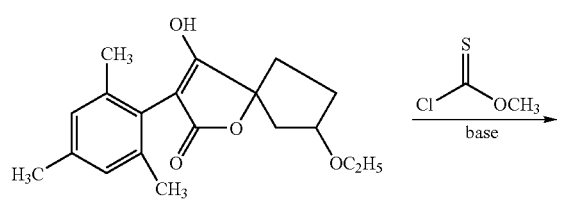

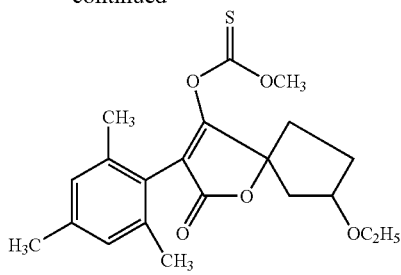

Using, for example, according to process (F) 7-butoxy-3-[(2,4,6-trimethyl)phenyl]-1-azaspiro[4,4]nonane-2,4-dione and methanesulfonyl chloride as starting materials, the course of the reaction can be represented by the following reaction scheme:

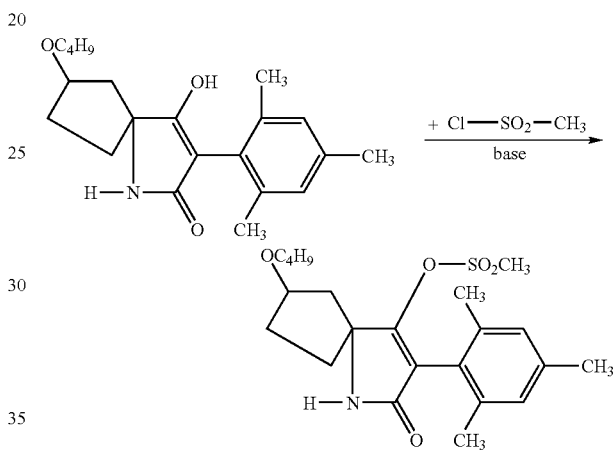

Using, for example, according to process (G) 7-methoxy-3-[(2,4-dichlor-6-methyl)-phenyl]-1-oxaspiro[4,4]nonane-2,4-dione and methanethiophosphonyl chloride 2,2,2-trifluoroethyl ester as starting materials, the course of the reaction can be represented by the following reaction scheme:

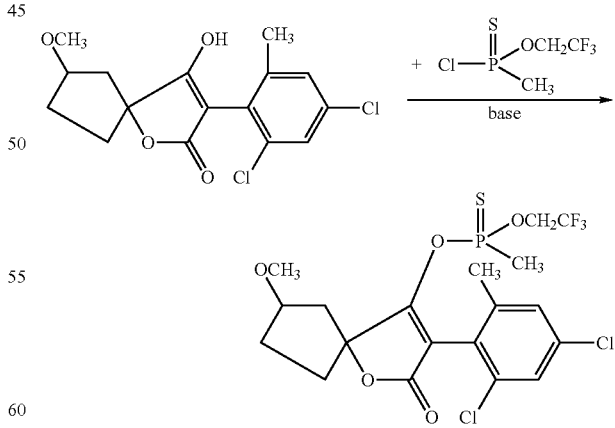

Using, for example, according to process (H) 7-methoxy-3-[(2,3,4,6-tetramethylphenyl]-1-azaspiro[4,4]nonane-2,4-dione and NaOH as components, the course of the process of the invention can be represented by the following reaction scheme:

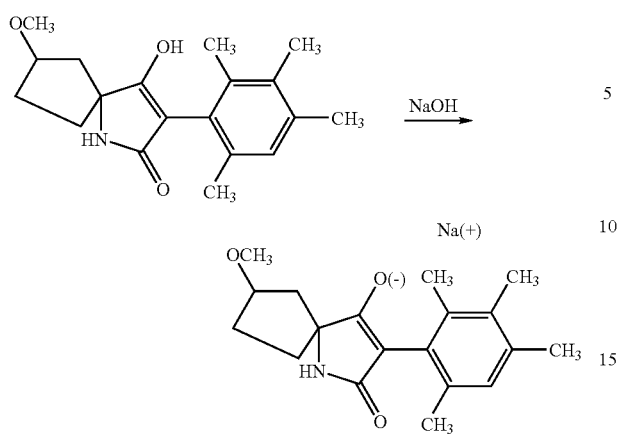

Using, for example, according to process (I) (variant α) 7-ethoxy-3-[(2,4,5-trimethyl)phenyl]-1-oxaspiro[4,4]nonane-2,4-dione and ethyl isocyanate as starting materials, the course of the reaction can be represented by the following reaction scheme:

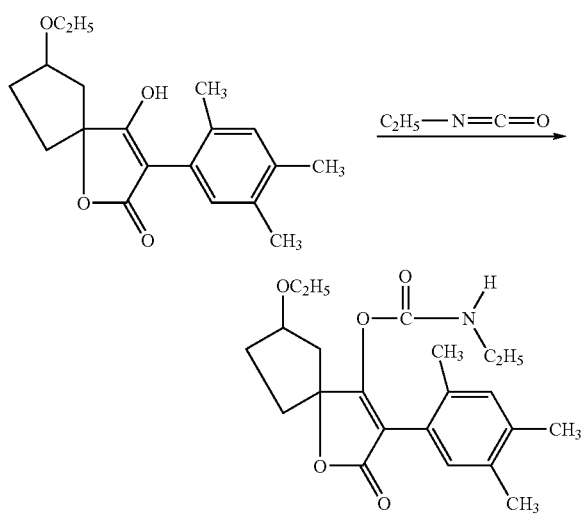

Using, for example, according to process (I) (variant β) 7-butoxy-3-[(2,4,6-trimethyl)phenyl]-1-azaspiro[4,4]nonane-2,4-dione and dimethylcarbamoyl chloride as starting materials, the course of the reaction can be represented by the following scheme:

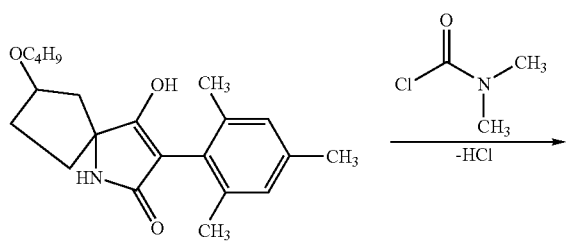

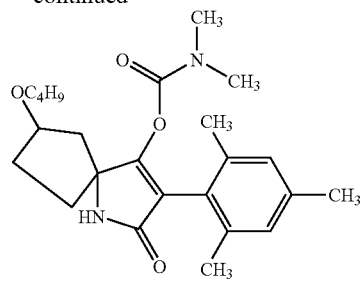

The compounds of the formula (II)

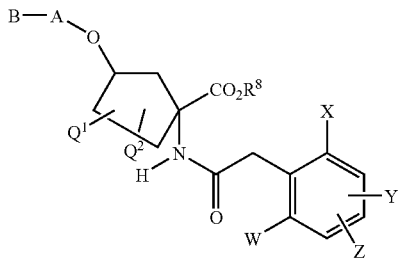

in which
A, B, $Q^1$, $Q^2$, W, X, Y, Z and $R^8$ are as defined above, needed as starting materials for process (A) of the invention, are new.

The acylamino acid esters of the formula (II) are obtained, for example, when amino acid derivatives of the formula (XIV)

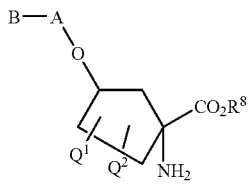

in which
A, B, $Q^1$ and $Q^2$ and $R^8$ are as defined above, are acylated with substituted phenylacetic acid derivatives of the formula (XV)

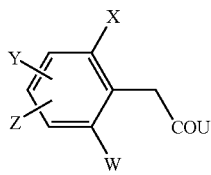

in which
W, X, Y and Z are as defined above and
U is a leaving group introduced by carboxylic acid activating reagents such as carbonyldiimidazole, carbonyldiimides (such as, for example, dicyclohexylcarbodiimide), phosphorylating reagents (such as, for example, $POCl_3$, BOP-Cl), halogenating agents such as, for example, thionyl chloride, oxalyl chloride, phosgene or chloroformic esters, (Chem. Reviews 52, 237-416 (1953); Bhattacharya, Indian J. Chem. 6, 341-5, 1968)
or when acylamino acids of the formula (XVI)

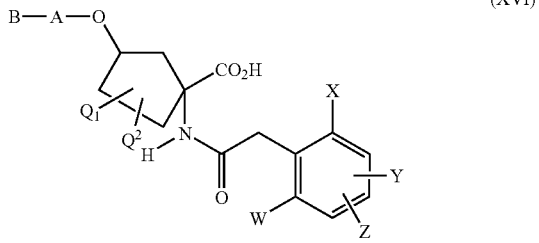

in which
A, B, $Q^1$, $Q^2$, W, X, Y and Z are as defined above,
are esterified (Chem. Ind. (London) 1568 (1968)).

The compounds of the formula (XVI)

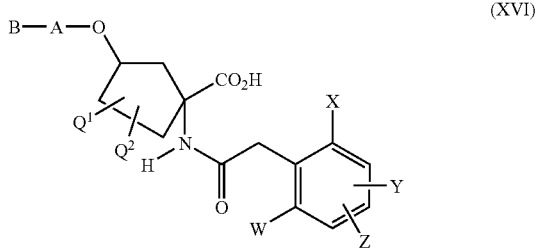

in which
A, B, $Q^1$, $Q^2$, W, X, Y and Z are as defined above,
are novel.

The compounds of the formula (XVI) are obtained, for example, when 1-aminocyclohexanecarboxylic acids of the formula (XVII)

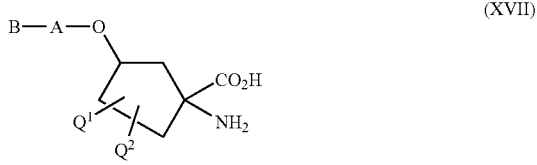

in which
A, B, $Q^1$ and $Q^2$ are as defined above
are acylated with substituted phenylacetic acid derivatives of the formula (XV)

in which
U, W, X, Y and Z are as defined above
in accordance with Schotten-Baumann (Organikum, VEB Deutscher Verlag der Wissenschaften, Berlin 1977, p. 505).

Some of the compounds of the formula (XV) are known, and/or they can be prepared by the known processes of the laid-open publications cited at the outset.

Some of the compounds of the formulae (XIV) and (XVII) are novel, and they can be prepared by known processes (Tetrahedron Assymetry, 8, 825 ff (1997) and WO 02/46128).

The compounds, required as starting materials for the process (B) according to the invention, of the formula (III)

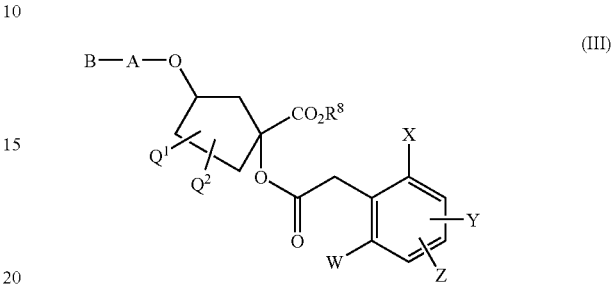

in which
A, B, $Q^1$, $Q^2$, W, X, Y, Z and $R^8$ are as defined above,
are novel.

They can be prepared in a simple manner by methods known in principle.

The compounds of the formula (III) are obtained, for example, when
1-hydroxycyclohexanecarboxylic esters of the formula (XVIII)

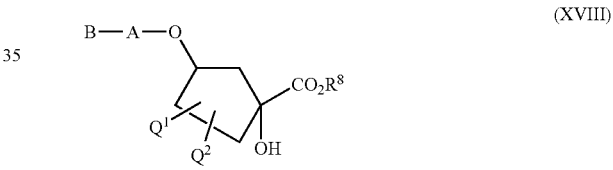

in which
A, B, $Q^1$, $Q^2$ and $R^8$ are as defined above,
are acylated with substituted phenylacetic acid derivatives of the formula (XV)

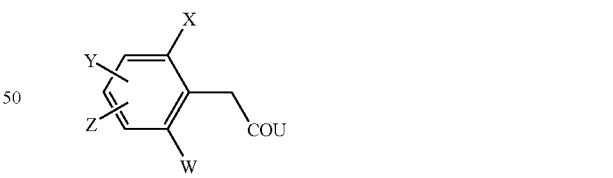

in which
U, W, X, Y and Z are as defined above
(Chem. Reviews 52, 237-416 (1953)).

The 1-hydroxy-3-alkoxycyclopentylcarboxylic esters of the formula (XVIII) are novel. They are obtained, for example, when substituted 1-hydroxy-3-alkoxycyclopentan-ecarbonitriles are reacted in the presence of acids, for example according to Pinner, with alcohols. The cyanohydrin is obtained, for example, by reacting substituted 3-alkoxycyclopentan-1-ones with hydrocyanic acid.

The acid halides of the formula (IV), carboxylic anhydrides of the formula (V), chloroformic esters or chloroformic thioesters of the formula (VI), chloromonothioformic esters or chlorodithioformic esters of the formula (VII), sulfonyl chlorides of the formula (VIII), phosphorus compounds of the formula (IX) and metal hydroxides, metal alkoxides or amines of the formulae (X) and (XI), respectively, and isocyanates of the formula (XII) and carbamoyl chlorides of the formula (XIII) furthermore required as starting materials for carrying out the processes (C), (D), (E), (F), (G), (H) and (I) according to the invention are generally known compounds of organic or inorganic chemistry.

In addition, the compounds of the formula (XV) are known from the patent applications cited at the outset and/or can be prepared by the methods given therein.

The process (A) is characterized in that compounds of the formula (II) in which A, B, $Q^1$, $Q^2$, W, X, Y, Z and $R^8$ are as defined above are subjected to an intramolecular condensation in the presence of a diluent and in the presence of a base.

Suitable diluents for use in the process (A) according to the invention are all organic solvents inert towards the reaction participants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulfoxide, sulfolane, dimethylformamide and N-methylpyrrolidone, and also alcohols, such as methanol, ethanol, propanol, isopropanol, butanol, isobutanol and tert-butanol.

Suitable bases (deprotonating agents) for carrying out the process (A) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which may also be used in the presence of phase-transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is furthermore possible to use alkali metals, such as sodium or potassium. Further, it is possible to employ alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (A) according to the invention, the reaction temperature may be varied within a relatively wide range. In general, the process is carried out at temperatures between –75° C. and 200° C., preferably between –50° C. and 150° C.

The process (A) is generally carried out under atmospheric pressure.

When carrying out the process (A) according to the invention, the reaction component of the formula (II) and the deprotonating base are generally employed in equimolar to about doubly equimolar amounts. However, it is also possible to use a relatively large excess (up to 3 mol) of one component or the other.

The process (B) is characterized in that compounds of the formula (III), in which A, B, $Q^1$, $Q^2$, W, X, Y, Z and $R^8$ are as defined above, are condensed intramolecularly in the presence of a diluent and in the presence of a base.

Suitable diluents for use in the process (B) according to the invention are all organic solvents inert towards the reaction participants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulfoxide, sulfolane, dimethylformamide and N-methylpyrrolidone. It is furthermore possible to use alcohols, such as methanol, ethanol, propanol, isopropanol, butanol, isobutanol and tert-butanol.

Suitable bases (deprotonating agents) for carrying out the process (B) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which may also be used in the presence of phase-transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is furthermore possible to use alkali metals, such as sodium or potassium. Further, use may be made of alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (B) according to the invention, the reaction temperature may be varied within a relatively wide range. In general, the process is carried out at temperatures between –75° C. and 200° C., preferably between –50° C. and 150° C.

The process (B) according to the invention is generally carried out under atmospheric pressure.

When carrying out the process (B) according to the invention, the reaction components of the formula (III) and the deprotonating bases are generally employed in approximately equimolar amounts. However, it is also possible to use a relatively large excess (up to 3 mol) of one component or the other.

The process ($C_\alpha$) is characterized in that compounds of the formulae (I-1-a) to (I-2-a) are in each case reacted with carbonyl halides of the formula (IV), if appropriate in the presence of a diluent and if appropriate in the presence of an acid binder.

Suitable diluents for use in the process ($C_\alpha$) according to the invention are all solvents inert towards the acid halides. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethylformamide, dimethyl sulfoxide and sulfolane. If the acid halide is sufficiently stable to hydrolysis, the reaction can also be carried out in the presence of water.

Suitable acid binders for the reaction according to process ($C_\alpha$) according to the invention are all customary acid acceptors. Preference is given to using tertiary amines, such as triethylamine, pyridine, diazabicyclooctane (DABCO), diazabicycloundecene (DBU), diazabicyclononene (DBN), Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

The reaction temperature in the process ($C_\alpha$) according to the invention can be varied within a relatively wide range. In general, the process is carried out at temperatures between –20° C. and +150° C., preferably between 0° C. and 100° C.

When carrying out the process ($C_\alpha$) according to the invention, the starting materials of the formulae (I-1-a) to (I-2-a) and the carbonyl halide of the formula (IV) are generally each employed in approximately equivalent amounts. However, it is also possible to use a relatively large excess (up to 5 mol) of the carbonyl halide. Work-up is carried out by customary methods.

The process ($C_\beta$) is characterized in that compounds of the formulae (I-1-a) to (I-2-a) are in each case reacted with carboxylic anhydrides of the formula (V), if appropriate in the presence of a diluent and if appropriate in the presence of an acid binder.

Suitable diluents for use in the process ($C_\beta$) according to the invention are, preferably, the diluents which are also preferred when using acid halides. Besides, excess carboxylic anhydride may simultaneously act as diluent.

Suitable acid binders, which are added, if appropriate, for process ($C_\beta$) are, preferably, the acid binders which are also preferred when using acid halides.

The reaction temperature in the process ($C_\beta$) according to the invention may be varied within a relatively wide range. In general, the process is carried out at temperatures between −20° C. and +150° C., preferably between 0° C. and 100° C.

When carrying out the process ($C_\beta$) according to the invention, the starting materials of the formulae (I-1-a) to (I-2-a) and the carboxylic anhydride of the formula (V) are generally each employed in approximately equivalent amounts. However, it is also possible to use a relatively large excess (up to 5 mol) of carboxylic anhydride. Work-up is carried out by customary methods.

In general, diluent and excess carboxylic anhydride and the carboxylic acid formed are removed by distillation or by washing with an organic solvent or with water.

The process (D) is characterized in that compounds of the formulae (I-1-a) to (I-2-a) are in each case reacted with chloroformic esters or chloroformic thioesters of the formula (VI), if appropriate in the presence of a diluent and if appropriate in the presence of an acid binder.

Suitable binders for the process (D) according to the invention are all customary acid acceptors. Preference is given to using tertiary amines, such as triethylamine, pyridine, DABCO, DBU, DBN, Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

Suitable diluents for use in the process (D) according to the invention are all solvents which are inert towards the chloroformic esters or chloroformic thioesters. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, moreover nitriles, such as acetonitrile, and also strongly polar solvents, such as dimethylformamide, dimethyl sulfoxide and sulfolane.

When carrying out the process (D) according to the invention, the reaction temperature can be varied within a relatively wide range. In general, the temperature is between −20° C. and +100° C., preferably between 0° C. and 50° C.

The process (D) according to the invention is generally carried out under atmospheric pressure.

When carrying out the process (D) according to the invention, the starting materials of the formulae (I-1-a) to (I-2-a) and the appropriate chloroformic ester or chloroformic thioester of the formula (VI) are generally each employed in approximately equivalent amounts. However, it is also possible to use a relatively large excess (up to 2 mol) of one component or the other. Work-up is carried out by customary methods. In general, precipitated salts are removed and the reaction mixture that remains is concentrated by removing the diluent under reduced pressure.

The process (E) according to the invention is characterized in that compounds of the formulae (I-1-a) to (I-2-a) are in each case reacted with compounds of the formula (VII) in the presence of a diluent and, if appropriate, in the presence of an acid binder.

In preparation process (E), about 1 mol of chloromonothioformic ester or chlorodithioformic ester of the formula (VII) is employed per mole of the starting material of the formulae (I-1-a) to (I-2-a) at from 0 to 120° C., preferably from 20 to 60° C.

Suitable diluents which are added, if appropriate, are all inert polar organic solvents, such as ethers, amides, sulfones, sulfoxides, and also halogenated alkanes.

Preference is given to using dimethyl sulfoxide, tetrahydrofuran, dimethylformamide, ethyl acetate or methylene chloride.

If, in a preferred embodiment, the enolate salt of the compounds (I-1-a) to (I-2-a) is prepared by addition of strong deprotonating agents, such as, for example, sodium hydride or potassium tert-butoxide, the further addition of acid binders may be dispensed with.

Suitable bases for use in the process (E) are all customary proton acceptors. Preference is given to using alkali metal hydrides, alkali metal alkoxides, alkali metal or alkaline earth metal carbonates or bicarbonates or nitrogen bases. Sodium hydride, sodium methoxide, sodium hydroxide, calcium hydroxide, potassium carbonate, sodium bicarbonate, triethylamine, dibenzylamine, diisopropylamine, pyridine, quinoline, diazabicyclooctane (DABCO), diazabicyclononene (DBN) and diazabicycloundecene (DBU) may be mentioned by way of example.

The reaction may be carried out at atmospheric pressure or under elevated pressure and is preferably carried out at atmospheric pressure. Work-up is carried out by customary methods.

The process (F) according to the invention is characterized in that compounds of the formulae (I-1-a) to (I-2-a) are in each case reacted with sulfonyl chlorides of the formula (VIII), if appropriate in the presence of a diluent and if appropriate in the presence of an acid binder.

In preparation process (F), about 1 mol of sulfonyl chloride of the formula (VIII) is reacted per mole of the starting material of the formula (I-1-a) to (I-2-a), at from −20 to 150° C., preferably from 0 to 70° C.

The process (F) is preferably carried out in the presence of a diluent.

Suitable diluents are all inert polar organic solvents, such as ethers, amides, ketones, carboxylic esters, nitriles, sulfones, sulfoxides or halogenated hydrocarbons, such as methylene chloride.

Preference is given to using dimethyl sulfoxide, tetrahydrofuran, dimethylformamide, ethyl acetate, methylene chloride.

If, in a preferred embodiment, the enolate salt of the compounds (I-1-a) to (I-2-a) is prepared by addition of strongly deprotonating agents (such as, for example, sodium hydride or potassium tert-butoxide), the further addition of acid binders may be dispensed with.

If acid binders are used, these are customary inorganic or organic bases, for example sodium hydroxide, sodium carbonate, potassium carbonate, pyridine and triethylamine.

The reaction may be carried out at atmospheric pressure or under elevated pressure and is preferably carried out at atmospheric pressure. Work-up is carried out by customary methods.

The process (G) according to the invention is characterized in that compounds of the formulae (I-1-a) to (I-2-a) are in each case reacted with phosphorus compounds of the formula (IX), if appropriate in the presence of a diluent and if appropriate in the presence of an acid binder.

In preparation process (G), to obtain compounds of the formulae (I-1-e) to (I-2-e), from 1 to 2, preferably from 1 to 1.3, mol of the phosphorus compound of the formula (IX) are reacted per mole of the compounds (I-1-a) to (I-2-a), at temperatures between −40° C. and 150° C., preferably between −10 and 110° C.

The process (G) is preferably carried out in the presence of a diluent.

Suitable diluents are all inert polar organic solvents, such as ethers, carboxylic esters, halogenated hydrocarbons, ketones, amides, nitriles, sulfones, sulfoxides, etc.

Preference is given to using acetonitrile, dimethyl sulfoxide, tetrahydrofuran, dimethyl-formamide, methylene chloride.

Suitable acid binders which are added, if appropriate, are customary inorganic or organic bases, such as hydroxides, carbonates or amines. Sodium hydroxide, sodium carbonate, potassium carbonate, pyridine and triethylamine may be mentioned by way of example.

The reaction can be carried out at atmospheric pressure or under elevated pressure and is preferably carried out at atmospheric pressure. Work-up is carried out by customary methods of organic chemistry. The end products are preferably purified by crystallization, chromatographic purification or "incipient distillation", i.e. removal of the volatile components under reduced pressure.

The process (H) is characterized in that compounds of the formulae (I-1-a) to (I-2-a) are in each case reacted with metal hydroxides or metal alkoxides of the formula (X) or amines of the formula (XI), if appropriate in the presence of a diluent.

Suitable diluents for use in the process (H) according to the invention are, preferably, ethers, such as tetrahydrofuran, dioxane, diethyl ether, or else alcohols, such as methanol, ethanol, isopropanol, and also water. The process (H) according to the invention is generally carried out under atmospheric pressure. The reaction temperature is generally between −20° C. and 100° C., preferably between 0° C. and 50° C.

The process (I) according to the invention is characterized in that compounds of the formulae (I-1-a) to (I-2-a) are in each case reacted with (Iα) compounds of the formula (XII), if appropriate in the presence of a diluent and if appropriate in the presence of a catalyst, or (Iβ) with compounds of the formula (XIII), if appropriate in the presence of a diluent and if appropriate in the presence of an acid binder.

In preparation process (Iα), about 1 mol of isocyanate of the formula (XII) is reacted per mole of starting material of the formulae (I-1-a) to (I-2-a), at from 0 to 100° C., preferably from 20 to 50° C.

The process (Iα) is preferably carried out in the presence of a diluent.

Suitable diluents are all inert organic solvents, such as aromatic hydrocarbons, halogenated hydrocarbons, ethers, amides, nitriles, sulfones or sulfoxides.

If appropriate, catalysts may be added to accelerate the reaction. Suitable for use as catalysts are, very advantageously, organotin compounds, such as, for example, dibutyltin dilaurate.

The reaction is preferably carried out at atmospheric pressure.

In preparation process (Iβ), about 1 mol of carbamoyl chloride of the formula (XIII) is reacted per mole of starting compound of the formulae (I-1-a) to (I-2-a), at from 0 to 150° C., preferably at from 20 to 70° C.

Suitable diluents which are added, if appropriate, are all inert polar organic solvents, such as ethers, carboxylic esters, nitrites, ketones, amides, sulfones, sulfoxides or halogenated hydrocarbons.

Preference is given to using dimethyl sulfoxide, tetrahydrofuran, dimethylformamide or methylene chloride.

If, in a preferred embodiment, the enolate salt of the compound (I-1-a) to (I-2-a) is prepared by addition of strong deprotonating agents (such as, for example, sodium hydride or potassium tert-butoxide), the further addition of acid binders may be dispensed with.

If acid binders are used, these are customary inorganic or organic bases, for example sodium hydroxide, sodium carbonate, potassium carbonate, triethylamine or pyridine.

The reaction can be carried out at atmospheric pressure or under elevated pressure and is preferably carried out at atmospheric pressure. Work-up is carried out by customary methods.

The active compounds of the invention, in combination with good plant tolerance and favorable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as plant protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp.,

*Atomaria* spp., *Attagenus* spp., *Bruchidius obtectus*, *Bruchus* spp., *Ceuthorhynchus* spp., *Cleonus mendicus*, *Conoderus* spp., *Cosmopolites* spp., *Costelytra zealandica*, *Curculio* spp., *Cryptorhynchus lapathi*, *Dermestes* spp., *Diabrotica* spp., *Epilachna* spp., *Faustinus cubae*, *Gibbium psylloides*, *Heteronychus arator*, *Hylamorpha elegans*, *Hylotrupes bajulus*, *Hypera postica*, *Hypothenemus* spp., *Lachnosterna consanguinea*, *Leptinotarsa decemlineata*, *Lissorhoptrus oryzophilus*, *Lixus* spp., *Lyctus* spp., *Meligethes aeneus*, *Melolontha melolontha*, *Migdolus* spp., *Monochamus* spp., *Naupactus xanthographus*, *Niptus hololeucus*, *Oryctes rhinoceros*, *Oryzaephilus surinamensis*, *Otiorrhynchus sulcatus*, *Oxycetonia jucunda*, *Phaedon cochleariae*, *Phyllophaga* spp., *Popillia japonica*, *Premnotrypes* spp., *Psylliodes chrysocephala*, *Ptinus* spp., *Rhizobius ventralis*, *Rhizopertha dominica*, *Sitophilus* spp., *Sphenophorus* spp., *Stemechus* spp., *Symphyletes* spp., *Tenebrio molitor*, *Tribolium* spp., *Trogoderma* spp., *Tychius* spp., *Xylotrechus* spp., *Zabrus* spp.

From the order of the Collembola, for example, *Onychiurus armatus*.

From the order of the Dermaptera, for example, *Forficula auricularia*.

From the order of the Diplopoda, for example, *Blaniulus guttulatus*.

From the order of the Diptera, for example, *Aedes* spp., *Anopheles* spp., *Bibio hortulanus*, *Calliphora erythrocephala*, *Ceratitis capitata*, *Chrysomyia* spp., *Cochliomyia* spp., *Cordylobia anthropophaga*, *Culex* spp., *Cuterebra* spp., *Dacus oleae*, *Dermatobia hominis*, *Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit*, *Pegomyia hyoscyami*, *Phorbia* spp., *Stomoxys* spp., *Tabanus* spp., *Tannia* spp., *Tipula paludosa*, *Wohlfahrtia* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale*, *Ancylostoma ceylanicum*, *Acylostoma braziliensis*, *Ancylostoma* spp., *Ascaris lubricoides*, *Ascaris* spp., *Brugia malayi*, *Brugia timori*, *Bunostomum* spp., *Chabertia* spp., *Clonorchis* spp., *Cooperia* spp., *Dicrocoelium* spp., *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp., *Strongyloides fuellebomi*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichuria*, *Wuchereria bancrofti*.

It is furthermore possible to control protozoa, such as *Eimeria*.

From the order of the Heteroptera, for example, *Anasa tristis*, *Antestiopsis* spp., *Blissus* spp., *Calocoris* spp., *Campylomma livida*, *Cavelerius* spp., *Cimex* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Nezara* spp., *Oebalus* spp., *Pentomidae*, *Piesma quadrata*, *Piezodorus* spp., *Psallus seriatus*, *Pseudacysta persea*, *Rhodnius* spp., *Sahlbergella singularis*, *Scotinophora* spp., *Stephanitis nashi*, *Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma piri*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Cameocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Clcadulina mbila*, *Coccomytilus halli*, *Coccus* spp., *Cryptomyzus ribis*, *Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus*, *Geococcus coffeae*, *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva fimbriolata*, *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes vaporariorum*, *Trioza* spp., *Typhlocyba* spp., *Unaspis* spp., *Viteus vitifolii*.

From the order of the Hymenoptera, for example, *Diprion* spp., *Hoplocampa* spp., *Lasius* spp., *Monomorium pharaonis*, *Vespa* spp.

From the order of the Isopoda, for example, *Armadillidium vulgare*, *Oniscus asellus*, *Porcellio scaber*.

From the order of the Isoptera, for example, *Reticulitermes* spp., *Odontotermes* spp.

From the order of the Lepidoptera, for example, *Acronicta major*, *Aedia leucomelas*, *Agrotis* spp., *Alabama argillacea*, *Anticarsia* spp., *Barathra brassicae*, *Bucculatrix thurberiella*, *Bupalus piniarius*, *Cacoecia podana*, *Capua reticulana*, *Carpocapsa pomonella*, *Chematobia brumata*, *Chilo* spp., *Choristoneura fumiferana*, *Clysia ambiguella*, *Cnaphalocerus* spp., *Earias insulana*, *Ephestia kuehniella*, *Euproctis chrysorrhoea*, *Euxoa* spp., *Feltia* spp., *Galleria mellonella*, *Helicoverpa* spp., *Heliothis* spp., *Hofmannophila pseudospretella*, *Homona magnanima*, *Hyponomeuta padella*, *Laphygma* spp., *Lithocolletis blancardella*, *Lithophane antennata*, *Loxagrotis albicosta*, *Lymantria* spp., *Malacosoma neustria*, *Mamestra brassicae*, *Mocis repanda*, *Mythimna separata*, *Oria* spp., *Oulema oryzae*, *Panolis flammea*, *Pectinophora gossypiella*, *Phyllocnistis citrella*, *Pieris* spp., *Plutella xylostella*, *Prodenia* spp., *Pseudaletia* spp., *Pseudoplusia includens*, *Pyrausta nubilalis*, *Spodoptera* spp., *Thermesia gemmatalis*, *Tinea pellionella*, *Tineola bisselliella*, *Tortrix viridana*, *Trichoplusia* spp.

From the order of the Orthoptera, for example, *Acheta domesticus*, *Blatta orientalis*, *Blattella germanica*, *Gryllotalpa* spp., *Leucophaea maderae*, *Locusta* spp., *Melanoplus* spp., *Periplaneta americana*, *Schistocerca gregaria*.

From the order of the Siphonaptera, for example, *Ceratophyllus* spp., *Xenopsylla cheopis*.

From the order of the Symphyla, for example, *Scutigerella immaculata*.

From the order of the Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.

From the order of the Thysanura, for example, *Lepisma saccharina*.

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (Mycoplasma-like organisms) and RLO (Rickettsia-like organisms). If appropriate, they can also be employed as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on the surroundings, habitat or storage space by the customary treatment methods, for example by immersion, spraying, evaporation, fogging, scattering, painting on, injection and, in the case of propagation material, in particular in the case of seeds, also by applying one or more coats.

The active compounds can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers. The formulations are prepared either in suitable plants or else before or during the application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulfones and sulfoxides (such as dimethyl sulfoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulfoxide, and also water.

Suitable solid carriers are:

for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and also protein hydrolysates; suitable dispersants are nonionic and/or ionic substances, for example from the classes of the alcohol-POE- and/or -POP-ethers, acid and/or POP-POE esters, alkyl aryl and/or POP-POE ethers, fat- and/or POP-POE adducts, POE- and/or POP-polyol derivatives, POE- and/or POP-sorbitan- or -sugar adducts, alkyl or aryl sulfates, alkyl- or arylsulfonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulfonic acid derivatives, unmodified and modified celluloses, aromatic and/or aliphatic sulfonic acids and their adducts with formaldehyde.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

The formulations generally comprise between 0.01 and 98% by weight of active compound, preferably between 0.5 and 90%.

The active compound according to the invention can be used in its commercially available formulations and in the use forms, prepared from these formulations, as a mixture with other active compounds, such as insecticides, attractants, sterilizing agents, bactericides, acaricides, nematicides, fungicides, growth-regulating substances, herbicides, safeners, fertilizers or semiochemicals.

Particularly favourable mixing components are, for example, the following compounds:

Fungicides:
  Inhibitors of nucleic acid synthesis
    benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid
  Inhibitors of mitosis and cell division
    benomyl, carbendazim, diethofencarb, fuberidazole, pencycuron, thiabendazole, thiophanat-methyl, zoxamide
  Inhibitors of respiratory chain complex I
    diflumetorim
  Inhibitors of respiratory chain complex II
    boscalid, carboxin, fenfuram, flutolanil, furametpyr, mepronil, oxycarboxin, penthiopyrad, thifluzamide
  Inhibitors of respiratory chain complex III
    azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin
  Decouplers
    dinocap, fluazinam
  Inhibitors of ATP production
    fentin acetate, fentin chloride, fentin hydroxide, silthiofam
  Inhibitors of amino acid biosynthesis and protein biosynthesis
    andoprim, blasticidin-S, cyprodinil, kasugamycin, kasugamycin hydrochloride hydrate, mepanipyrim, pyrimethanil
  Inhibitors of signal transduction
    fenpiclonil, fludioxonil, quinoxyfen
  Inhibitors of lipid and membrane synthesis
    chlozolinate, iprodione, procymidone, vinclozolin
    ampropylfos, potassium-ampropylfos, edifenphos, iprobenfos (IBP), isoprothiolane, pyrazophos
    tolclofos-methyl, biphenyl
    iodocarb, propamocarb, propamocarb hydrochloride
  Inhibitors of ergosterol biosynthesis
    fenhexamid,
    azaconazole, bitertanol, bromuconazole, cyproconazole, diclobutrazole, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulfate, oxpoconazole, fenarimol, flurprimidole, nuarimol, pyrifenox, triforine, pefurazoate, prochloraz, triflumizole, viniconazole,
    aldimorph, dodemorph, dodemorph acetate, fenpropimorph, tridemorph, fenpropidin, spiroxamine,
    naftifine, pyributicarb, terbinafine
  Inhibitors of cell wall synthesis
    benthiavalicarb, bialaphos, dimethomorph, flumorph, iprovalicarb, polyoxins, polyoxorim, validamycin A
  Inhibitors of melanin biosynthesis
    capropamid, diclocymet, fenoxanil, phthalid, pyroquilon, tricyclazole
  Resistance inductors
    acibenzolar-S-methyl, probenazole, tiadinil
Multisite
    captafol, captan, chlorothalonil, copper salts such as: copper hydroxide, copper naphthenate, copper oxychloride, copper sulfate, copper oxide, oxine-copper and Bordeaux mixture, dichlofluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulfur and sulfur preparations containing calcium polysulfide, thiram, tolylfluanid, zineb, ziram
Unknown mechanism
    amibromdol, benthiazol, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methyl sulfate, diphenylamine, ethaboxam, ferimzone, flumetover, flusulfamide, fluopicolide, fluoroimide, hexachlorobenzene, 8-hydroxy-quinoline sulfate, irumamycin, methasulfocarb, metrafenone, methyl isothiocyanate, mildiomycin, natamycin, nickel dimethyl dithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrol nitrin, quintozene, tecloftalam, tecnazene, triazoxide, trichlamide, zarilamid and 2,3,5,6-tetrachloro-4-(methylsulfonyl)pyridine, N-(4-chloro-2-nitrophenyl)-N-ethyl-4-methylbenzenesulfonamide, 2-amino-4-methyl-N-phenyl-5-thiazolecarboxamide, 2-chloro-N-(2,3-dihydro-1,1,3-trimethyl-1H-inden-4-yl)-3-pyridine-carboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)phenyl]ethylidene]-amino]oxy]methyl]phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxy-phenyl)imino]methyl]thio]methyl]-.alpha.-(methoxymethylene)benzacetate, 4-chloro-alpha-propynyloxy-N-[2-[3-methoxy-4-(2-propynyloxy)phenyl]ethyl]benzacetamide, (2S)-N-[2-[4-[[3-(4-chlorophenyl)-2-propynyl]oxy]-3-methoxyphenyl]ethyl]-3-methyl-2-[(methylsulfonyl)amino] butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidin-7-amine, 5-chloro-N-[(1R)-1,2-dimethylpropyl]-6-(2,4,6-trifluorophenyl)[1,2,4]triazolo[1,5-a]pyrimidin-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy)imino][6-(difluoromethoxy)-2,3-difluorophenyl]methyl}-2-benzacetamide, N-(3-ethyl-3,5,5-trimethylcyclohexyl)-3-formylamino-2-hydroxybenzamide, 2-[[[[1-[3-(1-fluoro-2-phenylethyl)oxy]phenyl]ethylidene]amino]oxy]methyl]-alpha-(methoxyimino)-N-methyl-alphaE-benzacetamide, N-{2-[3-chloro-5-(trifluoromethyl)pyridin-2-yl]ethyl}-2-(trifluoro-methyl)benzamide, N-(3',4'-dichloro-5-fluorobiphenyl-2-yl)-3-(difluoromethyl)-1-methyl-1H-pyrazole-4-carboxamide, N-(6-methoxy-3-pyridinyl)cyclopropanecarboxamide, 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide Bactericides:
bronopol, dichlorophen, nitrapyrin, nickel dimethyldithiocarbamate, kasugamycin, octhilinone, furancarboxylic acid, oxytetracycline, probenazole, streptomycin, tecloftalam, copper sulfate and other copper preparations.

Insecticides/Acaricides/Nematicides:
Acetylcholine esterase (ACHE) inhibitors
carbamates,
for example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, triazamate organophosphates,
for example acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulfone, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion Sodium channel modulators/voltage-dependent sodium channel blockers
pyrethroids,
for example acrinathrin, allethrin (d-cis-trans, d-trans), beta-cyfluthrin, bifenthrin, bioallethrin, bioallethrin-S-cyclopentyl isomer, bioethanomethrin, biopermethrin, bioresmethrin, chlovaporthrin, cis-cypermethrin, cis-resmethrin, cis-permethrin, clocythrin, cyprothrin, cyfluthrin, cyhalothrin, cypermethrin (alpha-, beta-, theta-, zeta-), cyphenothrin, deltamethrin, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans-isomer), prallethrin, profluthrin, protrifenbute, pyresmethrin, resmethrin, RU 15525, silafluofen, tau-fluvalinate, tefluthrin, terallethrin, tetramethrin (-1R-isomer), tralomethrin, transfluthrin, ZXI 8901, pyrethrins (pyrethrum)

DDT
oxadiazines,
for example indoxacarb
semicarbazones,
for example metaflumizone (BAS 320 1)

Acetylcholine receptor agonists/antagonists
chloronicotinyls,
for example acetamiprid, clothianidin, dinotefuran, imidacloprid, nitenpyram, nithiazine, thiacloprid, thiamethoxam
nicotine, bensultap, cartap Acetylcholine receptor modulators
spinosyns,
for example spinosad GABA-controlled chloride channel antagonists
organochlorines,
for example camphechlor, chlordane, endosulfan, gamma-HCH, HCH, heptachlor, lindane, methoxychlor
fiproles,
for example acetoprole, ethiprole, fipronil, pyrafluprole, pyriprole, vaniliprole Chloride channel activators
mectins,
for example avermectin, emamectin, emamectin-benzoate, ivermectin, milbemycin Juvenile hormone mimetics,
for example diofenolan, epofenonane, fenoxycarb, hydroprene, kinoprene, methoprene, pyriproxifen, triprene Ecdysone agonists/disruptors
diacylhydrazines,
for example chromafenozide, halofenozide, methoxyfenozide, tebufenozide Chitin biosynthesis inhibitors
benzoylureas,
for example bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron
buprofezin
cyromazine Oxidative phosphorylation inhibitors, ATP disruptors
diafenthiuron
organotin compounds,
for example azocyclotin, cyhexatin, fenbutatin-oxide Oxidative phosphorylation decouplers acting by interrupting the H-proton gradient
pyrroles,
for example chlorfenapyr
dinitrophenols,
for example binapacyrl, dinobuton, dinocap, DNOC
Side-I electron transport inhibitors
METIs,
for example fenazaquin, fenpyroximate, pyrimidifen, pyridaben, tebufenpyrad, tolfenpyrad
hydramethylnon
dicofol
Side-II electron transport inhibitors
rotenone
Side-III electron transport inhibitors
acequinocyl, fluacrypyrim
Microbial disruptors of the insect gut membrane
*Bacillus thuringiensis* strains
Lipid synthesis inhibitors
tetronic acids,
for example spirodiclofen, spiromesifen
tetramic acids,
for example spirotetramat
carboxamides,
for example flonicamid
octopaminergic agonists,
for example amitraz
Inhibitors of magnesium-stimulated ATPase,
propargite
ryanodine receptor effectors
a) benzoic acid dicarboxamides,
for example flubendiamide
b) anthranilamides, for example
Rynaxapyr (3-bromo-N-{4-chloro-2-methyl-6-[(methylamino)carbonyl]phenyl}-1-(3-chloropyridin-2-yl)-1H-pyrazole-5-carboxamide)
nereistoxin analogs,
for example thiocyclam hydrogen oxalate, thiosultap-sodium
Biologicals, hormones or pheromones
azadirachtin, *Bacillus* spec., *Beauveria* spec., *codlemone*, *Metarrhizium* spec., *Paecilomyces* spec., *thuringiensin*, *Verticillium* spec.
Active compounds with unknown or unspecific mechanisms of action
fumigants,
for example aluminium phosphide, methyl bromide, sulfuryl fluoride
antifeedants,
for example cryolite, flonicamid, pymetrozine
Mite growth inhibitors,
for example clofentezine, etoxazole, hexythiazox
amidoflumet, benclothiaz, benzoximate, bifenazate, bromopropylate, buprofezin, chinomethionat, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulfluramid, tetradifon, tetrasul, triarathene, verbutin A mixture with other known active compounds, such as herbicides, fertilizers, growth regulators, safeners, semiochemicals, or else with agents for improving the plant properties, is also possible.

When used as insecticides, the active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

When used as insecticides, the active compounds according to the invention can furthermore be present in their commercially available formulations and in the use forms, prepared from these formulations, as a mixture with inhibitors which reduce degradation of the active compound after use in the environment of the plant, on the surface of parts of plants or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

The compounds are employed in a customary manner appropriate for the use forms.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The transgenic plants or plant cultivars (obtained by genetic engineering) which are preferably to be treated according to the invention include all plants which, by virtue of the genetic modification, received genetic material which imparted particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular increased defence of the plants against insects, arachnids, nematodes and slugs and snails by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulfonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulfonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated according to the invention in a particularly advantageous manner with the compounds of the general formula I and/or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Wemeckiella* spp., *Lepikentron* spp., *Damalina* spp., *Trichodectes* spp., *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example, *Pulex* spp., *Ctenocephalides* spp., *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattela germanica, Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey, etc.) should be diminished, so that more economic and easier animal husbandry is possible by use of the active compounds according to the invention.

The active compounds according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of molded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10,000-fold dilution, or they can be used as a chemical bath.

It has furthermore been found that the compounds according to the invention also have a strong insecticidal action against insects which destroy industrial materials.

The following insects may be mentioned as examples and as preferred—but without any limitation:

Beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus;*

Hymenopterons, such as *Sirex juvencus, Urocerus gigas, Urocerus gigas taignus, Urocerus augur;*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;*

Bristletails, such as *Lepisma saccharina.*

Industrial materials in the present connection are to be understood as meaning non-living materials, such as, preferably, plastics, adhesives, sizes, papers and cardboards, leather, wood and processed wood products and coating compositions.

The ready-to-use compositions may, if appropriate, comprise further insecticides and, if appropriate, one or more fungicides.

With respect to possible additional additives, reference may be made to the insecticides and fungicides mentioned above.

The compounds according to the invention can likewise be employed for protecting objects which come into contact with saltwater or brackish water, such as hulls, screens, nets, buildings, moorings and signalling systems, against fouling.

Furthermore, the compounds according to the invention, alone or in combinations with other active compounds, may be employed as antifouling agents.

In domestic, hygiene and stored-product protection, the active compounds are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus.*

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, *Aviculariidae, Araneidae.*

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedestaeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga camaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Pemphigus* spp., *Phylloera vastatrix, Phthirus pubis.*

From the order of the Heteroptera, for example, *Cimex hemipterus, Cimex lectularius, Rhodinus prolixus, Triatoma infestans.*

In the field of household insecticides, they are used alone or in combination with other suitable active compounds, such as phosphoric esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

The active compounds/active compound combinations according to the invention can also be used as defoliants, desiccants, haulm killers and, in particular, as weed killers. Weeds in the broadest sense are understood as meaning all plants which grow at locations where they are undesired. Whether the substances according to the invention act as nonselective or selective herbicides depends essentially on the application rate.

The active compounds/active compound combinations according to the invention can be used for example in the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopo-*

*dium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindemia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.*

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Monocotyledonous crops of the genera: *Allium, Ananas, Asparagus, Avena, Hordeum, Oryza, Panicum, Saccharum, Secale, Sorghum, Triticale, Triticum, Zea.*

However, the use of the active compounds/active compound combinations according to the invention is in no way restricted to these genera, but extends in the same manner to other plants.

Depending on the concentration, the active compounds/active compound combinations according to the invention are suitable for the nonselective weed control on, for example, industrial terrains and railway tracks and on paths and locations with and without trees. Likewise the active compounds according to the invention can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The compounds of the formula (I)/active compound combinations according to the invention have strong herbicidal activity and a broad activity spectrum when used on the soil and on aerial plant parts. To a certain extent, they are also suitable for the selective control of monocotyledonous and dicotyledonous weeds in monocotyledonous and dicotyledonous crops, both pre- and post-emergence.

At certain concentrations or application rates, the active compounds/active compound combinations according to the invention can also be employed for controlling animal pests and fungal or bacterial plant diseases. If appropriate, they can also be used as intermediates or precursors for the synthesis of other active compounds.

The active compounds/active compound combinations can be converted into the customary formulations, such as solutions, emulsions, wettable powders, suspensions, powders, dusting agents, pastes, soluble powders, granules, suspoemulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If the extender used is water, it is also possible to use, for example, organic solvents as auxiliary solvents. Suitable liquid solvents are essentially: aromatics, such as xylene, toluene or alkyl-naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulfoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates, suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and protein hydrolysates; suitable dispersants are: for example lignosulfite waste liquors and methylcellulose.

Tackifiers such as carboxymethylcellulose and natural and synthetic polymers in the form of powders, granules or latices, such as gum arabic, polyvinyl alcohol and polyvinyl acetate, and also natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds/active compound combinations according to the invention, as such or in their formulations, can also be used for weed control purposes as a mixture with known herbicides and/or with substances which improve crop plant tolerance ("safeners"), ready mixes or tank mixes being possible. Mixtures with herbicide products which contain one or more known herbicides and a safener are hence also possible.

Herbicides which are suitable for the mixtures are known herbicides, for example acetochlor, acifluorfen (-sodium), aclonifen, alachlor, alloxydim (-sodium), ametryne, amicarb-azone, amidochlor, amidosulfuron, aminopyralid, anilofos, asulam, atrazine, azafenidin, azimsulfuron, beflubutamid, benazolin (-ethyl), benfuresate, bensulfuron (-methyl), bentazone, bencarbazone, benzfendizone, benzobicyclon, benzofenap, benzoylprop (-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlomitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (-P), diclofop (-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxysulfuron, etobenzanid, fenoxaprop (-P-ethyl), fentrazamide, flamprop (-isopropyl, -isopropyl-L, -methyl), flazasulfuron, florasulam, fluazifop (-P-butyl), fluazolate, flucarbazone (-sodium), flufenacet, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulfuron (-methyl, -sodium), flurenol (-butyl), fluridone, fluoroxypyr (-butoxypropyl, -meptyl), flurprimidol, flurtamone, fluthiacet (-methyl), fluthiamide, fomesafen, foramsulfuron, glufosinate (-ammonium), glyphosate (-isopropylammonium), halosafen, haloxyfop (-ethoxyethyl, -P-methyl), hexazinone, HOK-201, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyrifop, lactofen, lenacil, linuron, MCPA, mecoprop, mefenacet, mesosulfurone, mesotrione, metamifop, metamitron, metazachlor, methabenzthiazuron, metobenzuron, metobromuron, (alpha-) metolachlor, metosulam, metoxuron, metribuzin, metsulfuron (-methyl), molinate, monolinuron, naproanilide, napropamide, neburon, nicosulfuron, norflurazon, orbencarb, orthosulfamuron, oryzalin, oxadiargyl, oxadiazon, oxasulfuron, oxaziclomefone, oxyfluorfen, paraquat, pelargonic acid, pendimethalin, pendralin, penoxsulam, pentoxazone, phenmedipham, picolinafen, pinoxaden, piperophos, pretilachlor, primisulfuron (-methyl), profluazol, prometryn, propachlor, propanil, propaquizafop, propisochlor, propoxycarbazone (-sodium), propyzamide, prosulfocarb, prosulfuron, pyraflufen (-ethyl), pyrasulfotole, pyrazogyl, pyrazolate, pyrazosulfuron (-ethyl), pyrazoxyfen, pyribenzoxim, pyributicarb, pyridate, pyridatol, pyriftalide, pyriminobac (-methyl), pyrimisulfan, pyrithiobac (-sodium), pyroxsulam, pyroxasulfone, quinchlorac, quinmerac, quinoclamine, quizalofop (-P-ethyl, -P-tefuryl), rimsulfuron, sethoxydim, simazine, simetryn, sulcotrione, sulfentrazone, sulfometuron (-methyl), sulfosate, sulfosulfuron, tebutam, tebuthiuron, tembotrione, tepraloxydim, terbuthylazine, terbutryn, thenylchlor, thiafluamide, thiazopyr, thidiazimin, thiencarbazone-methyl, thifensulfuron (-methyl), thiobencarb, tiocarbazil, topramezone, tralkoxydim, triallate, triasulfuron, tribenuron (-methyl), triclopyr, tridiphane, trifluralin, trifloxysulfuron, triflusulfuron (-methyl), tritosulfuron and

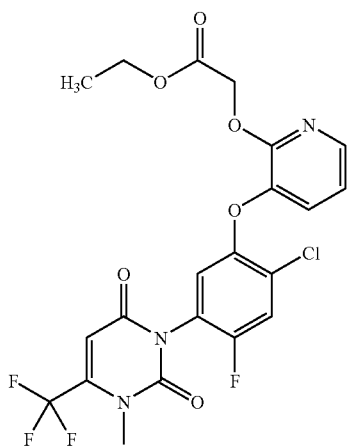

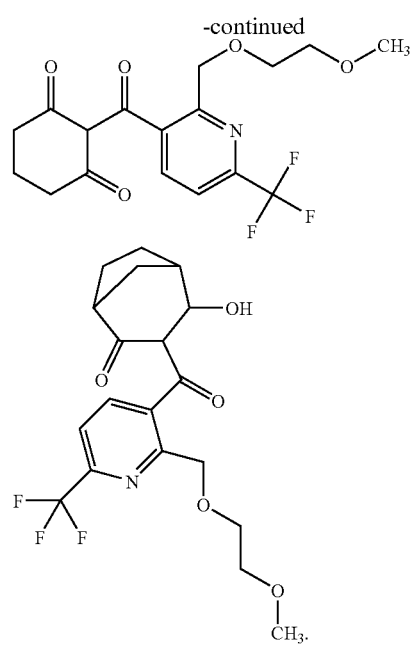

A mixture with other known active compounds, such as fungicides, insectides, acaricides, nematicides, bird repellents, plant nutrients and soil conditioners, is also possible.

The active compounds or active compound combinations can be applied as such, in the form of their formulations or the use forms prepared therefrom by further dilution, such as ready-to-use solutions, suspensions, emulsions, powders, pastes and granules. They are applied in the customary manner, for example by pouring, spraying, atomizing, spreading.

The active compounds or active compound combinations according to the invention can be applied both before and after plant emergence. They can also be incorporated into the soil prior to planting.

The application rate of active compound can vary within a substantial range. Essentially, it depends on the nature of the desired effect. In general, the application rates are between 1 g and 10 kg of active compound per hectare of soil area, preferably between 5 g and 5 kg per ha.

The advantageous effect of the compatibility with crop plants of the active compound combinations according to the invention is particularly pronounced at certain concentration ratios. However, the weight ratios of the active compounds in the active compound combinations can be varied within relatively wide ranges. In general, salts from 0.001 to 1000 parts by weight, preferably from 0.01 to 100 parts by weight, particularly preferably 0.05 to 20 parts by weight, of one of the compounds which improves crop plant compatibility (antidotes/safeners) mentioned above under (b') are present per part by weight of active compound of the formula (I).

The active compound combinations according to the invention are generally applied in the form of finished formulations. However, the active compounds contained in the active compound combinations can, as individual formulations, also be mixed during use, i.e. be applied in the form of tank mixes.

For certain applications, in particular by the post-emergence method, it may furthermore be advantageous to include, as further additives in the formulations, mineral or vegetable oils which are tolerated by plants (for example the commercial preparation "Rako Binol"), or ammonium salts, such as, for example, ammonium sulfate or ammonium thiocyanate.

The novel active compound combinations can be used as such, in the form of their formulations or the use forms prepared therefrom by further dilution, such as ready-to-use solutions, suspensions, emulsions, powders, pastes and granules. Application is in the customary manner, for example by pouring, spraying, atomizing, dusting or scattering.

The application rates of the active compound combinations according to the invention can be varied within a certain range; they depend, inter alia, on the weather and on soil factors. In general, the application rates are between 0.001 and 5 kg per ha, preferably between 0.005 and 2 kg per ha, particularly preferably between 0.01 and 0.5 kg per ha.

The active compound combinations according to the invention can be applied before and after emergence of the plants, that is to say by the pre-emergence and post-emergence method.

Depending on their properties, the safeners to be used according to the invention can be used for pretreating the seed of the crop plant (seed dressing) or can be introduced into the seed furrows prior to sowing or be used separately prior to the herbicide or together with the herbicide, before or after emergence of the plants.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

*Xanthomonas* species, such as, for example, *Xanthomonas campestris* pv. *oryzae*;

*Pseudomonas* species, such as, for example, *Pseudomonas syringae* pv. *lachrymans*;

*Erwinia* species, such as, for example, *Erwinia amylovora*;

*Pythium* species, such as, for example, *Pythium ultimum*;

*Phytophthora* species, such as, for example, *Phytophthora infestans*;

*Pseudoperonospora* species, such as, for example, *Pseudoperonospora humuli* or *Pseudoperonospora cubensis*;

*Plasmopara* species, such as, for example, *Plasmopara viticola*;

*Bremia* species, such as, for example, *Bremia lactucae*;

*Peronospora* species, such as, for example, *Peronospora pisi* or *P. brassicae*;

*Erysiphe* species, such as, for example, *Erysiphe graminis*;

*Sphaerotheca* species, such as, for example, *Sphaerotheca fuliginea*;

*Podosphaera* species, such as, for example, *Podosphaera leucotricha*;

*Venturia* species, such as, for example, *Venturia inaequalis*;

*Pyrenophora* species, such as, for example, *Pyrenophora teres* or *P. graminea*
(conidia form: *Drechslera*, syn: *Helminthosporium*);

*Cochliobolus* species, such as, for example, *Cochliobolus sativus*
(conidia form: *Drechslera*, syn: *Helminthosporium*);

*Uromyces* species, such as, for example, *Uromyces appendiculatus*;

*Puccinia* species, such as, for example, *Puccinia recondita*;

*Sclerotinia* species, such as, for example, *Sclerotinia sclerotiorum*;

*Tilletia* species, such as, for example, *Tilletia caries*;

*Ustilago* species, such as, for example, *Ustilago nuda* or *Ustilago avenae*;

*Pellicularia* species, such as, for example, *Pellicularia sasakii*;

*Pyricularia* species, such as, for example, *Pyricularia oryzae*;

*Fusarium* species, such as, for example, *Fusarium culmorum*;

*Botrytis* species, such as, for example, *Botrytis cinerea*;

*Septoria* species, such as, for example, *Septoria nodorum*;

*Leptosphaeria* species, such as, for example, *Leptosphaeria nodorum*;

*Cercospora* species, such as, for example, *Cercospora canescens*;

*Alternaria* species, such as, for example, *Alternaria brassicae*; and

*Pseudocercosporella* species, such as, for example, *Pseudocercosporella herpotrichoides*.

The active compounds according to the invention also have very good fortifying action in plants. Accordingly, they can be used for mobilizing the defences of the plant against attack by unwanted microorganisms.

In the present context, plant-fortifying (resistance-inducing) substances are to be understood as meaning those substances which are capable of stimulating the defence system of plants such that, when the treated plants are subsequently inoculated with unwanted microorganisms, they show substantial resistance against these microorganisms.

In the present case, unwanted microorganisms are to be understood as meaning phytopathogenic fungi, bacteria and viruses. Accordingly, the substances according to the invention can be used to protect plants for a certain period after the treatment against attack by the pathogens mentioned. The period for which protection is provided generally extends over 1 to 10 days, preferably 1 to 7 days, after the treatment of the plants with the active compounds.

The fact that the active compounds are well tolerated by plants at the concentrations required for controlling plant diseases permits the treatment of above-ground parts of plants, of propagation stock and seeds, and of the soil.

The active compounds according to the invention are also suitable for increasing the yield of crops. In addition, they show reduced toxicity and are well tolerated by plants.

At certain concentrations and application rates, the active compounds according to the invention can, if appropriate, also be used as herbicides, for influencing plant growth and for controlling animal pests. If appropriate, they can also be used as intermediates and precursors for the synthesis of further active compounds.

In the protection of materials, the substances according to the invention can be employed for protecting industrial materials against infection with, and destruction by, unwanted microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms.

The active compounds according to the invention preferably act against fungi, in particular molds, wood-discoloring and wood-destroying fungi (Basidiomycetes), and against slime organisms and algae.

Microorganisms of the following genera may be mentioned as examples:

Alternaria, such as *Alternaria tenuis*,
Aspergillus, such as *Aspergillus niger*,
Chaetomium, such as *Chaetomium globosum*,
Coniophora, such as *Coniophora puetana*,
Lentinus, such as *Lentinus tigrinus*,
Penicillium, such as *Penicillium glaucum*,
Polyporus, such as *Polyporus versicolor*,
Aureobasidium, such as *Aureobasidium pullulans*,
Sclerophoma, such as *Sclerophoma pityophila*,
Trichoderma, such as *Trichoderma viride*,
Escherichia, such as *Escherichia coli*,
Pseudomonas, such as *Pseudomonas aeruginosa*,
Staphylococcus, such as *Staphylococcus aureus*.

Depending on their particular physical and/or chemical properties, the active compounds can be converted into the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates, or else protein hydrolysates. Suitable dispersants are: for example lignosulfite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention can be used as such or in their formulations, also in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Examples of suitable mixing components are the compounds mentioned above (fungicides, bactericides, insecticides, acaricides, nematicides).

A mixture with other known active compounds, such as herbicides, or with fertilizers and growth regulators, is also possible.

In addition, the compounds of the formula (I) according to the invention also have very good antimycotic activity. They have a very broad antimycotic activity spectrum in particular against dermatophytes and yeasts, molds and diphasic fungi (for example against *Candida* species, such as *Candida albicans*, *Candida glabrata*), and *Epidermophyton floccosum*, *Aspergillus* species, such as *Aspergillus niger* and *Aspergillus fumigatus*, *Trichophyton* species, such as *Trichophyton mentagrophytes*, *Microsporon* species such as *Microsporon canis* and *audouinii*. The list of these fungi by no means limits the mycotic spectrum covered, but is only for illustration.

The active compounds can be used as such, in the form of their formulations or the use forms prepared therefrom, such as ready-to-use solutions, suspensions, wettable powders, pastes, soluble powders, dusting agents and granules. Application is carried out in a customary manner, for example by pouring, spraying, atomizing, broadcasting, dusting, foaming, spreading, etc. It is furthermore possible to apply the active compounds by the ultra-low-volume method, or to inject the active compound preparation or the active compound itself into the soil. It is also possible to treat the seeds of the plants.

When using the active compounds according to the invention as fungicides, the application rates can be varied within a relatively wide range, depending on the kind of application. For the treatment of parts of plants, the active compound application rates are generally between 0.1 and 10,000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10,000 g/ha, preferably between 1 and 5000 g/ha.

The term "active compound" includes the active compound combinations mentioned, and also the formulated compositions comprising ammonium salts and/or phosphonium salts and, if appropriate, penetrants.

The preparation and the use of the active compounds according to the invention are illustrated by the examples below.

PREPARATION EXAMPLES

Example I-1-a-1

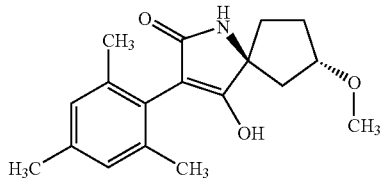

Potassium tert-butoxide is initially charged in 2 ml of dimethylacetamide and heated to 100° C. At this temperature, 3 ml of a solution according to Example II-1 in dimethylacetamide are added in 10 portions over a period of 1 h. The mixture is stirred at 100° C. for 2 h, and 20 ml of water are then added and the pH is adjusted to 1 using concentrated hydrochloric acid. The mixture is then concentrated and taken up in 50 ml of dichloromethane, dried with sodium sulfate and concentrated. Purification by column chromatography (gradient (n-heptane/ethyl acetate 4:1 to ethyl acetate) gives 80 mg of target product (yield: 42% of theory) of m.p.: 209-217° C.

Analogously to Example (I-1-a-1) and in accordance with the general statements on the preparation, the following compounds of the formula (I-1-a) are obtained:

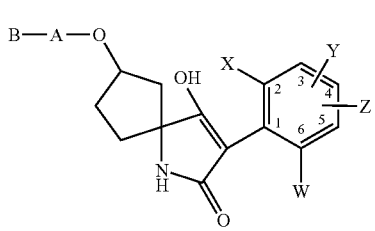

(I-1-a)

| Ex.-No. | W | X | Y | Z | A | B | M.p. ° C. | Isomer |
|---|---|---|---|---|---|---|---|---|
| I-1-a-2 | $C_2H_5$ | Br | 4-$CH_3$ | H | $CH_2$ | H | solidified foam<br>*2.41 (m, 2H, Ar—$CH_2$)<br>3.23 (s, 3H, $OCH_3$)<br>3.92 (m, 1H, $CHOCH_3$) | cis |
| I-1-a-3 | $C_2H_5$ | Br | 4-$CH_3$ | H | $CH_2$ | H | oil<br>*2.41 (m, 2H, Ar—$CH_2$)<br>3.20 (s, 3H, $OCH_3$)<br>4.01 (m, 1H, $CHOCH_3$) | trans |
| I-1-a-4 | $OCH_3$ | $C_2H_5$ | 4-Cl | H | $CH_2$ | H | solidified glass<br>*2.45 (m, 2H, Ar—$CH_2$)<br>3.27 (s, 3H, $CHOCH_3$)<br>4.01, 4.06 (2m, Σ 1H, $CHOCH_3$) | trans |
| I-1-a-5 | $OCH_3$ | $C_2H_5$ | 4-Cl | H | $CH_2$ | H | 171-178 | cis |
| I-1-a-6 | $CH_3$ | $CH_3$ | 4-$CH_3$ | H | $CH_2$ | H | 232 | cis |
| I-1-a-7 | $C_2H_5$ | Br | 4-$CH_3$ | H | $CH_2$ | $CH_3$ | 182-186 | cis |
| I-1-a-8 | $OCH_3$ | $C_2H_5$ | 4-Cl | H | — | H | viscous oil<br>*1.00, 1.09 (dt, 3H, Ar—$CH_2$—$CH_3$)<br>4.14, 4.24 (2 m, Σ, 1H, CHOH) | cis |
| I-1-a-9 | $CH_3$ | $CH_3$ | 4-$CH_3$ | H | $CH_2$ | $CH_3$ | 199-206 | cis |
| I-1-a-10 | $CH_3$ | $CH_3$ | 4-Br | H | $CH_2$ | H | 242 | cis |
| I-i-a-11 | $CH_3$ | Cl | 4-$CH_3$ | H | $CH_2$ | H | 243 | cis |
| I-1-a-12 | $C_2H_5$ | Br | 4-$CH_3$ | H | $CH_2$ | $C_3H_7$ | 70-82 | cis |
| I-1-a-13 | $CH_3$ | $CH_3$ | 4-$CH_3$ | H | $CH_2$ | $C_3H_7$ | 180-188 | cis |
| I-1-a-14 | $C_2H_5$ | Br | 4-$CH_3$ | H | $CH_2$ | $C_3H_7$ | 69-76 | trans |
| I-1-a-15 | $CH_3$ | $CH_3$ | 4-$CH_3$ | H | $CH_2$ | $C_3H_7$ | oil<br>*6.84 ppm (s, 2H, Ar—H), 4.10 ppm (m, 1H, CH—O), 3.37 ppm (t, 2H, CH—$OCH_2$), | trans |
| I-1-a-16 | H | $CH_3$ | 5-(4-Cl-Ph) | H | $CH_2$ | H | 231-233 | cis |
| I-1-a-17 | $CH_3$ | $CH_3$ | 4-$CH_3$ | H | $CH_2$ | $C_2H_5$ | 224 | cis |
| I-1-a-18 | $CH_3$ | $CH_3$ | 4-$CH_3$ | H | $CH_2$ | $C_2H_5$ | solidified foam<br>*6.84 ppm (s, 2H, Ar—H), 4.11 ppm (m, 1H, CH—O), 3.33 ppm (t, 2H, CH—$OCH_2$), | trans |
| I-1-a-19 | $C_2H_5$ | Br | 4-$CH_3$ | H | $CH_2$ | $C_2H_5$ | 172-174 | cis |
| I-1-a-20 | $C_2H_5$ | Br | 4-$CH_3$ | H | $CH_2$ | $C_2H_5$ | solidified foam<br>*7.30 and 7.02 ppm (in each case s, 1H, Ar—H), 4.10 ppm (m, 1H, CH—O), 3.32 ppm (t, 2H, CH—$OCH_2$), | cis |
| I-1-a-21 | $C_2H_5$ | Br | 4-$CH_3$ | H | $CH_2$ | △— | solidified foam<br>*4.04 ppm (m, 1H CH—O), 3.21 ppm (d, 2H, CH—$OCH_2$), 2.30 ppm (s, 3H, Ar—$CH_3$), | cis |

-continued (I-1-a)

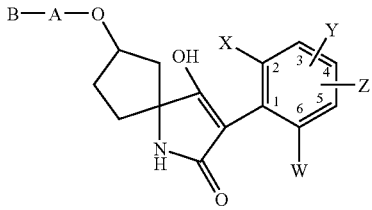

| Ex.-No. | W | X | Y | Z | A | B | M.p. °C. | Isomer |
|---|---|---|---|---|---|---|---|---|
| I-1-a-22 | C$_2$H$_5$ | Br | 4-CH$_3$ | H | CH$_2$ | △ | solidified foam *4.15 ppm (m, 1H, CH—O), 3.21 ppm (d, 2H, CH—OCH$_2$), 2.30 ppm (s, 3H, Ar—CH$_3$), | trans |
| I-1-a-23 | CH$_3$ | CH$_3$ | 4-CH$_3$ | H | CH$_2$ | △ | 217-221 | cis |
| I-1-a-24 | CH$_3$ | CH$_3$ | 4-CH$_3$ | H | CH$_2$ | △ | solidified foam *6.84 ppm (s, 2H, Ar—H), 4.15 ppm (m, 1H, CH—O), 3.22 ppm (d, 2H, CH—OCH$_2$), | trans |
| I-1-a-25 | H | CH$_3$ | 5-(4-Cl—Ph) | H | CH$_2$ | △ | 211 | cis |
| I-1-a-26 | H | CH$_3$ | 5-(4-Cl—Ph) | H | CH$_2$ | △ | solidified foam *433 ppm (m, 1H, CH—O), 3.24 ppm (d, 2H, CH—OCH$_2$), 2.23 ppm (s, 3H, Ar—CH$_3$), | trans |
| I-1-a-27 | C$_2$H$_5$ | Br | 4-CH$_3$ | H | —(CH$_2$)$_2$— | OCH$_3$ | solidified foam *4.04 ppm (m, 1H CH—O), 3.27 ppm (s, 3H, OCH$_3$), 2.29 ppm (s, 3H, Ar—CH$_3$), | cis |
| I-1-a-28 | C$_2$H$_5$ | Br | 4-CH$_3$ | H | —(CH$_2$)$_2$— | OCH$_3$ | solidified foam *4.15 ppm (m, 1H, CH—O), 3.25 ppm (s, 3H, OCH$_3$), 2.29 ppm (s, 3H, Ar—CH$_3$), | trans |
| I-1-a-29 | CH$_3$ | CH$_3$ | 4-CH$_3$ | H | —(CH$_2$)$_2$— | OCH$_3$ | solidified foam *6.85 ppm (s, 2H, Ar—H), 4.15 ppm (m, 1H, CH—O, 3.25 ppm (s, 3H, OCH$_3$), | trans |
| I-1-a-30 | CH$_3$ | CH$_3$ | 4-CH$_3$ | H | —(CH$_2$)$_2$— | OCH$_3$ | solidified foam *6.84 ppm (s, 2H, Ar—H), 4.05 ppm (m, 1H, CH—O), 3.27 ppm (s, 3H, OCH$_3$), | cis |
| I-1-a-31 | C$_2$H$_5$ | Cl | 4-Cl | H | CH$_2$ | △ | solidified foam **7.44 and 7.28 ppm (in each case s, 1H, Ar—H), 4.04 ppm (m, 1H, CH—O), 0.47 and 0.18 ppm (in each case m2, 2H, CH-Cyclopropyl) | cis |

-continued

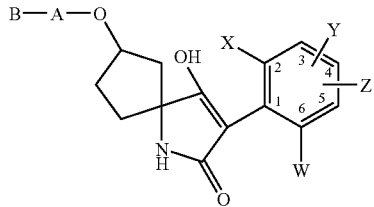
(I-1-a)

| Ex.-No. | W | X | Y | Z | A | B | M.p. °C. | Isomer |
|---|---|---|---|---|---|---|---|---|
| I-1-a-32 | C₂H₅ | Cl | 4-Cl | H | CH₂ | △ | solidified foam **744 and 7.28 ppm (in each case s, 1H, Ar—H), 4.14 ppm (m, 1H, CH—O), 0.47 and 0.18 ppm (in each case m, 2H, CH-Cyclopropyl), | trans |

*¹H-NMR (400 MHz, d₆-DMSO): shift δ in ppm
**¹H-NMR (300 MHz, d₆-DMSO): shift δ in ppm
Ph = phenyl Example I-1-b-1

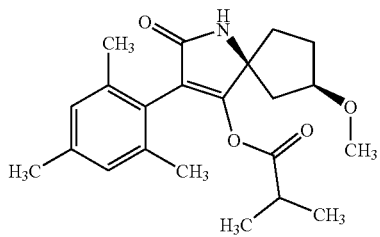

0.18 g of the compound according to Example I-1-a-6 is initially charged in 8 ml of ethyl acetate, 0.1 ml of triethylamine and 1.5 mg of 4-N,N'-dimethylaminopyridine are added and the mixture is heated to 60° C. A solution of 0.07 g of isobutyryl chloride in 2 ml of ethyl acetate is added in 7 portions over a period of 60 min, and the mixture is stirred at 60° C. for 6 h. The mixture is allowed to stand overnight, half-concentrated sodium chloride solution is then added and the organic phase is separated off and purified by column chromatography (gradient EtOAc/n-heptane 1:9 to ethyl acetate/n-heptane 100:0) on silica gel. This gives 85 mg of a colorless solid (38% of theoretical yield). M.p. 126-134° C.

Analogously to Example (I-1-b-1) and in accordance with the general statements on the preparation, the following compounds of the formula (I-1-b) are obtained:

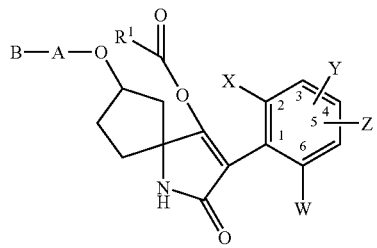
(I-1-b)

| Ex.-No. | W | X | Y | Z | A | B | R¹ | M.p. °C. | Isomer |
|---|---|---|---|---|---|---|---|---|---|
| I-1-b-2 | C₂H₅ | Br | 4-CH₃ | H | CH₂ | H | i-C₃H₇ | viscous resin *4.00 ppm (m, 1 H, CH—OCH₃), 2.27 ppm (s, 3 H, Ar—CH₃) 1.04 ppm (m, 6 H, CH(CH₃)₂) | cis |
| I-1-b-3 | C₂H₅ | OCH₃ | 4-Cl | H | CH₂ | H | i-C₃H₇ | 163 | cis |
| I-1-b-4 | C₂H₅ | Br | 4-CH₃ | H | CH₂ | C₃H₇ | i-C₃H₇ | oil *7.28 and 7.01 ppm (m each case s, 1 H, Ar—H), 4.07 ppm (m, 1 H, CH—OCH₂), 3.41 ppm (t, 2 H, CH—OCH₂), 1.05 ppm (m, 6 H, CH(CH₃)₂) | cis |

-continued

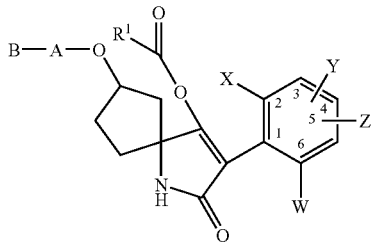

(I-1-b)

| Ex.-No. | W | X | Y | Z | A | B | R¹ | M.p. °C. | Isomer |
|---|---|---|---|---|---|---|---|---|---|
| I-1-b-5 | CH₃ | CH₃ | 4-CH₃ | H | CH₂ | C₃H₇ | i-C₃H₇ | 76-85 | cis |
| I-1-b-6 | C₂H₅ | Br | 4-CH₃ | H | CH₂ | △ | i-C₃H₇ | oil *4.13 ppm (m, 1 H, CH—O), 2.29 ppm (s, 3 H, Ar—CH₃), 1.04 ppm (m, 6 H, CH(CH₃)₂), 0.56 ppm (m, 2 H, CH-Cyclopropyl) | cis |
| I-1-b-7 | C₂H₅ | Br | 4-CH₃ | H | CH₂ | △ | i-C₃H₇ | oil *4.16 ppm (m, 1 H, CH—O), 2.29 ppm (s, 3 H, Ar—CH₃), 1.05 ppm (m, 6 H, CH(CH₃)₂), 0.52 ppm (m, 2 H, CH-Cyclopropyl) | trans |
| I-1-b-8 | CH₃ | CH₃ | 4-CH₃ | H | CH₂ | △ | i-C₃H₇ | 105 | cis |
| I-1-b-9 | CH₃ | CH₃ | 4-CH₃ | H | CH₂ | △ | i-C₃H₇ | 142 | trans |
| I-1-b-10 | H | CH₃ | 5-(4-Cl-Ph) | H | CH₂ | △ | i-C₃H₇ | 136 | cis |
| I-1-b-11 | H | CH₃ | 5-(4-Cl-Ph) | H | CH₂ | △ | i-C₃H₇ | 154-156 | trans |
| I-1-b-12 | C₂H₅ | Br | 4-CH₃ | H | —(CH₂)₂— | OCH₃ | i-C₃H₇ | oil *4.15 ppm (m, 1 H, CH—O), 3.43 ppm (d, 3 H, OCH₃), 2.30 ppm (s, 3 H, Ar—CH₃), 1.03 ppm (m, 6 H, CH(CH₃)₂) | cis |
| I-1-b-13 | C₂H₅ | Br | 4-CH₃ | H | —(CH₂)₂— | OCH₃ | i-C₃H₇ | oil *4.18 ppm (m, 1 H, CH—O), 3.37 ppm (d, 3 H, OCH₃), 2.29 ppm (s, 3 H, Ar—CH₃), 1.05 ppm (m, 6 H, CH(CH₃)₂) | trans |
| I-1-b-14 | CH₃ | CH₃ | 4-CH₃ | H | —(CH₂)₂— | OCH₃ | i-C₃H₇ | wax *6.82 ppm (s, 2 H, Ar—H), 4.15 ppm (m, 1 H, CH—O), 3.42 ppm (d, 3 H, OCH₃), 1.00 ppm (m, 6 H, CH(CH₃)₂) | cis |
| I-1-b-15 | CH₃ | CH₃ | 4-CH₃ | H | —(CH₂)₂— | OCH₃ | i-C₃H₇ | wax *6.84 ppm (s, 2 H, Ar—H), 4.17 ppm (m, 1 H, CH—O), 3.37 ppm (d, 3 H, OCH₃), 1.01 ppm (m, 6 H, CH(CH₃)₂) | trans |
| I-1-b-16 | C₂H₅ | Br | 4-CH₃ | H | —(CH₂)₂— | OCH₃ | 2-Cl-Ph | 127-147 | cis |

*¹H-NMR (400 MHz, CDCl₃): shift δ in ppm
Ph = phenyl

Example I-1-c-1

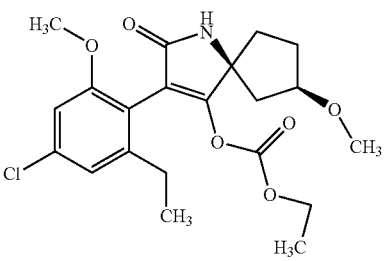

0.077 g according to Example I-1-a-5 (0.219 mmol) is dissolved in 3 ml of dichloromethane, 0.04 ml of triethylamine (1.2 eq) is added and the mixture is stirred at room temperature for 10 min. 0.02 ml of ethyl chloroformate (1.1 eq) is then added, and the mixture is stirred at room temperature overnight. After extraction with 4% strength $Na_2CO_3$ solution, the organic phase is dried, concentrated and purified by column chromatography on silica gel (gradient n-heptane/ethyl acetate 9:1 to ethyl acetate). This gives 44 mg of product as a solidified glass (yield: 47% of theory).

$^1$H-NMR (400 MHz, $CDCl_3$) δ=3.32 (s, 3H, CH—O$\underline{CH_3}$), 3.76 (s, 3H, Ar—O$\underline{CH_3}$), 4.05 (q, 2H, O$\underline{CH_2}$) ppm.

Example (I-1-c-2) is obtained analogously to Example (I-1-c-1).

(I-1-c-2)

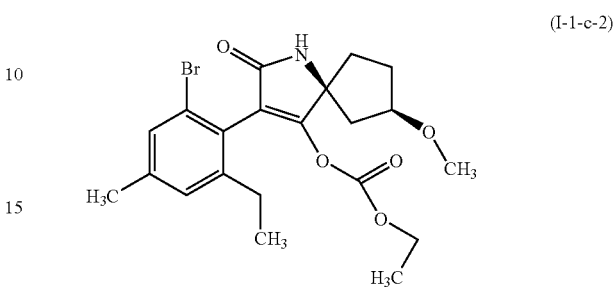

$^1$H-NMR (400 MHz, $CDCl_3$) δ=3.32 (s, 3H, CH—O$\underline{CH_3}$), 2.58 (m, 2H, Ar—$\underline{CH_2}$), 4.07 (q, 2H, O$\underline{CH_2}$) ppm.

Analogously to Example (I-1-c-1), (I-1-c-2) and in accordance with the general statements on the preparation, the following compounds of the formula (I-1-c) are obtained:

(I-1-c)

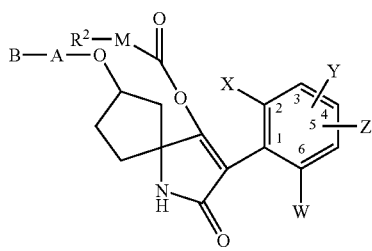

| Ex.-No. | W | X | Y | Z | A | B | M | R¹ | M.p. °C. | Isomer |
|---|---|---|---|---|---|---|---|---|---|---|
| I-1-c-3 | $CH_3$ | $CH_3$ | 4-$CH_3$ | H | $CH_2$ | H | O | $C_2H_5$ | 114-117 | cis |
| I-1-c-4 | $CH_3$ | $CH_3$ | 4-$CH_3$ | H | $CH_2$ | H | O | $C_2H_5$ | 174-178 | trans |
| I-1-c-5 | $CH_3$ | Br | 4-$CH_3$ | H | $CH_2$ | H | O | $C_2H_5$ | oil *7.24 and 6.99 ppm (in each case s, 1 H, Ar—H), 4.07 ppm (q, 2 H, $CH_2$—O), 4.00 ppm (m, 1 H, CH—O$CH_3$) | cis |
| I-1-c-6 | $CH_3$ | Cl | 4-$CH_3$ | H | $CH_2$ | H | O | $C_2H_5$ | 119-123 | cis |
| I-1-c-7 | $C_2H_5$ | $CH_3$ | 4-Br | H | $CH_2$ | $C_3H_7$ | O | $C_2H_5$ | oil *7.24 and 7.01 ppm (in each case s, 1 H, Ar—H), 4.07 ppm (m, 3 H, $CH_2$—O and CH—O$CH_2$), 3.41 ppm (t, 2 H, CH—O$CH_2$) | cis |
| I-1-c-8 | $CH_3$ | $CH_3$ | 4-$CH_3$ | H | $CH_2$ | $C_3H_7$ | O | $C_2H_5$ | oil *6.86 ppm (s, 2 H, Ar—H), 4.08 ppm (m, 1 H, CH—O), 4.01 ppm (q, 2 H, $CH_2$—O), 3.42 ppm (t, 2 H, CH—O$CH_2$) | cis |
| I-1-c-9 | $C_2H_5$ | Br | 4-$CH_3$ | H | $CH_2$ | $C_3H_7$ | O | $C_2H_5$ | oil *7.24 and 7.01 ppm (in each case s, 1 H, Ar—H), 4.10 ppm (m, 3 H, $CH_2$—O and CH—O$CH_2$) 3.37 ppm (t, 2 H, CH—O$CH_2$) | trans |
| I-1-c-10 | $CH_3$ | $CH_3$ | 4-$CH_3$ | H | $CH_2$ | $C_3H_7$ | O | $C_2H_5$ | 126-129 | trans |
| I-1-c-11 | $C_2H_5$ | Br | 4-$CH_3$ | H | $CH_2$ | $CH_3$ | O | $C_2H_5$ | 94-96 | cis |

-continued

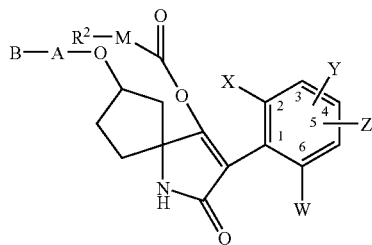
(I-1-c)

| Ex.-No. | W | X | Y | Z | A | B | M | R¹ | M.p. °C. | Isomer |
|---|---|---|---|---|---|---|---|---|---|---|
| I-1-c-12 | $C_2H_5$ | Br | 4-$CH_3$ | H | $CH_2$ | $CH_3$ | O | $C_2H_5$ | oil<br>*7.28 and 7.01 ppm (in each case s, 1 H, Ar—H),<br>4.13 ppm (m, 1 H, CH—O$CH_2$),<br>4.07 ppm (q, 2 H, $CH_2$—O),<br>3.45 ppm (t, 2 H, CH—O$CH_2$) | trans |
| I-1-c-13 | $CH_3$ | $CH_3$ | 4-$CH_3$ | H | $CH_2$ | $CH_3$ | O | $C_2H_5$ | oil<br>*6.87 ppm (s, 2 H, Ar—H), 4.13 ppm (m, 1 H, CH—O), 4.01 ppm (q, 2 H, $CH_2$—O), 3.47 ppm (t, 2 H, CH—O$CH_2$) | cis |
| I-1-c-14 | $CH_3$ | $CH_3$ | 4-$CH_3$ | H | $CH_2$ | $CH_3$ | O | $C_2H_5$ | 120-125 | trans |
| I-1-c-15 | H | $CH_3$ | 5-(4-Cl-Ph) | H | $CH_2$ | H | O | $C_2H_5$ | viscous oil<br>**4.03 ppm (m, 3 H, CH—O$CH_3$, $CH_2$—O), 2.32 (s, 3 H, Ar—$CH_3$) | cis |
| I-1-c-16 | H | $CH_3$ | 5-(4-Cl-Ph) | H | $CH_2$ | H | O | $C_2H_5$ | 167-171 | trans |
| I-1-c-17 | $CH_3$ | $CH_3$ | 4-$CH_3$ | H | $CH_2$ | $C_2H_5$ | O | $C_2H_5$ | oil<br>*6.87 ppm (s, 2 H, Ar—H),<br>4.08 ppm (m, 1 H, CH—O),<br>4.01 ppm (q, 2 H, $CH_2$—O),<br>3.37 ppm (t, 2 H, CH—O$CH_2$) | cis |
| I-1-c-18 | $C_2H_5$ | Br | 4-$CH_3$ | H | $CH_2$ | $C_2H_5$ | O | $C_2H_5$ | 102-105 | cis |
| I-1-c-19 | $CH_3$ | $CH_3$ | 4-$CH_3$ | H | $CH_2$ | $C_2H_5$ | O | $C_2H_5$ | 110-113 | trans |
| I-1-c-20 | $C_2H_5$ | Br | 4-$CH_3$ | H | $CH_2$ | $C_2H_5$ | O | $C_2H_5$ | oil<br>*7.24 and 7.01 ppm (in each case s, 1 H, Ar—H),<br>4.08 ppm (m, 3 H, CH—O and $CH_2$—O),<br>3.37 ppm (t, 2 H, CH—O$CH_2$) | trans |
| I-1-c-21 | $C_2H_5$ | Br | 4-$CH_3$ | H | $CH_2$ | △ | O | $C_2H_5$ | 127-129 | cis |
| I-1-c-22 | $CH_3$ | $CH_3$ | 4-$CH_3$ | H | $CH_2$ | △ | O | $C_2H_5$ | 113 | cis |
| I-1-c-23 | H | $CH_3$ | 5-(4-Cl-Ph) | H | $CH_2$ | △ | O | $C_2H_5$ | solidified foam<br>*4.15 ppm (m, 1 H, CH—O),<br>4.01 ppm (q, 2 H, $CH_2$—O),<br>3.27 ppm (d, 2 H, CH—O$CH_2$),<br>2.34 ppm (s, 3 H, Ar—$CH_3$) | cis |
| I-1-c-24 | $C_2H_5$ | Br | 4-$CH_3$ | H | $CH_2$ | △ | O | $C_2H_5$ | oil<br>*4.15 ppm (m, 1 H, CH—O),<br>4.05 ppm (q, 2 H, $CH_2$—O),<br>3.23 ppm (d, 2 H, CH—O$CH_2$),<br>2.30 ppm (s, 3 H, Ar—$CH_3$) | trans |
| I-1-c-25 | $CH_3$ | $CH_3$ | 4-$CH_3$ | H | $CH_2$ | △ | O | $C_2H_5$ | solidified foam<br>*6.86 ppm (s, 2 H, Ar—H), 4.15 ppm (m, 1 H, CH—O), 4.03 ppm (q, 2 H, $CH_2$—O), 3.23 ppm (d, 2 H, CH—O$CH_2$) | trans |
| I-1-c-26 | H | $CH_3$ | 5-(4-Cl-Ph) | H | $CH_2$ | △ | O | $C_2H_5$ | solidified foam<br>*4.18 ppm (m, 1 H, CH—O),<br>4.01 ppm (q, 2 H, $CH_2$—O),<br>3.23 ppm (d, 2 H, CH—O$CH_2$),<br>2.31 ppm (s, 3 H, Ar—$CH_3$) | trans |

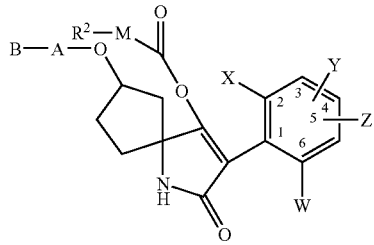

(I-1-c)

| Ex.-No. | W | X | Y | Z | A | B | M | R¹ | M.p. °C. | Isomer |
|---|---|---|---|---|---|---|---|---|---|---|
| I-1-c-27 | $C_2H_5$ | Br | 4-$CH_3$ | H | —$(CH_2)_2$— | $OCH_3$ | O | $C_2H_5$ | oil<br>*4.16 ppm (m, 1 H, CH—O),<br>4.05 ppm (q, 2 H, $CH_2$—O),<br>3.42 ppm (s, 3 H, $OCH_3$),<br>2.30 ppm (s, 3 H, Ar—$CH_3$), | cis |
| I-1-c-28 | $C_2H_5$ | Br | 4-$CH_3$ | H | —$(CH_2)_2$— | $OCH_3$ | O | $C_2H_5$ | oil<br>*4.18 ppm (m, 1 H, CH—O),<br>4.05 ppm (q, 2 H, $CH_2$—O),<br>3.38 ppm (s, 3 H, $OCH_3$),<br>2.30 ppm (s, 3 H, Ar—$CH_3$), | trans |
| I-1-c-29 | $CH_3$ | $CH_3$ | 4-$CH_3$ | H | —$(CH_2)_2$— | $OCH_3$ | O | $C_2H_5$ | solidified foam<br>*6.85 ppm (s, 2 H, Ar—H),<br>4.15 ppm (m, 1 H, CH—O),<br>4.01 ppm (q, 2 H, $CH_2$—O),<br>3.42 ppm (s, 3 H, $OCH_3$) | cis |
| I-1-c-30 | $CH_3$ | $CH_3$ | 4-$CH_3$ | H | —$(CH_2)_2$— | $OCH_3$ | O | $C_2H_5$ | oil<br>*6.86 ppm (s, 2 H, Ar—H),<br>4.17 ppm (m, 1 H, CH—O),<br>4.01 ppm (q, 2 H, $CH_2$—O),<br>3.37 ppm (s, 3 H, CH—O—$CH_3$ | trans |
| I-1-c-31 | $C_2H_5$ | Br | 4-$CH_3$ | H | —$(CH_2)_2$— | $OCH_3$ | O | $CH_2$=CH—$CH_2$ | oil<br>*4.48 ppm (d, 2 H, $CH_2$=CH—$CH_2$O),<br>4.16 ppm (m, 1 H, CH—O),<br>3.42 ppm (d, 3 H, $OCH_3$),<br>2.30 ppm (s, 3 H, Ar—$CH_3$), | cis |
| I-1-c-32 | $C_2H_5$ | Cl | 4-Cl | H | $CH_2$ | △ | O | $C_2H_5$ | oil<br>*7.29 and 7.18 ppm (in each case s, 1 H, Ar—H),<br>4.15 ppm (m, 1 H, CH—O),<br>4.07 ppm (q, 2 H, C(=O)$OCH_2$),<br>1.04 ppm (m, 1 H, CH-Cyclopropyl) | cis |
| I-1-c-33 | $C_2H_5$ | Cl | 4-Cl | H | $CH_2$ | △ | O | $C_2H_5$ | oil<br>*7.29 and 7.18 ppm (in each case s, 1 H, Ar—H),<br>4.17 ppm (m, 1 H, CH—O),<br>4.08 ppm (q, 2 H, C(=O)$OCH_2$),<br>1.04 ppm (m, 1 H, CH-Cyclopropyl) | trans |

*¹H-NMR (400 MHz, $CDCl_3$): shift δ in ppm
**¹H-NMR (300 MHz, $CDCl_3$): shift δ in ppm
Ph = phenyl Example I-1-d-1

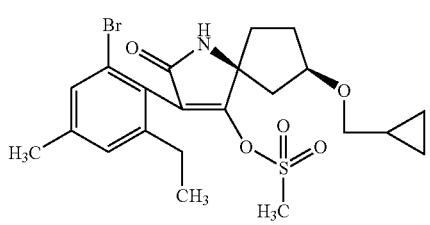

0.156 g of the compound according to Ex. I-1-a-21 is dissolved in 10 ml of dichloromethane and 0.06 ml of triethlamine is added. 0.032 ml of methanesulfonyl chloride is added to this solution, and the mixture is stirred at room temperature for 20 h. The mixture is then stirred with 5 ml of 5% strength sodium bicarbonate solution for 0.5 h, the organic solution is separated off, dried with sodium sulfate and concentrated using a rotary evaporator, and the residue obtained is purified by column chromatography (gradient n-heptane+ethyl acetate 9:1 to ethyl acetate).

Yield: 0.14 g (76% of theory)

¹H-NMR ($CDCl_3$, 400 MHz): δ=4.16 ppm (m, 1H, CH—O), 2.62 ppm (s, 3H, $SO_2\underline{CH_3}$), 2.32 ppm, (s, 3H, Ar—$\underline{CH_3}$), 1.03 ppm (m, 1H, $\underline{CH}$-cyclopropyl).

Example I-1-f-1

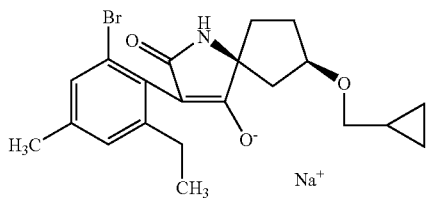

0.1 g of the compound according to Ex. I-1-a-21 is dissolved in 7 ml of anhydrous methanol, and 0.045 ml of 30% strength sodium methoxide solution is added. After 2 h, the solution is concentrated using a rotary evaporator, concentrated 2 more times on a rotary evaporator, in each case with 5 ml of anhydrous methanol, and dried under high vacuum.

Yield: 0.095 g (90% of theory)

$^1$H-NMR (d6-DMSO, 400 MHz): δ=5.01 ppm (m, 1H, CH—O), 2.21 ppm (s, 3H, Ar—CH$_3$), 0.45 and 0.16 ppm (in each case m, 2H, CH-cyclopropyl).

Example I-1-g-1

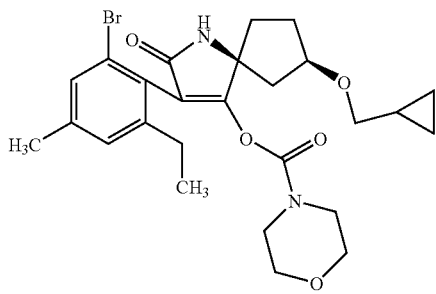

0.158 g of the compound according to Ex. I-1-a-21 is dissolved in 10 ml of chloroform, and 0.08 ml of diisopropylethylamine and 2 mg of DMAP are added. 0.048 ml of morpholine-N-carbonyl chloride is added, and the solution is stirred at room temperature for 20 h. The mixture is then stirred with 5 ml of 5% strength sodium bicarbonate solution for 0.5 h, the organic solution is separated off, dried with sodium sulfate and concentrated using a rotary evaporator and the residue obtained is purified by column chromatography (gradient n-heptane+ethyl acetate 9:1 to ethyl acetate).

Yield: 0.14 g (63% of theory)

$^1$H-NMR (CDCl$_3$, 400 MHz): δ=4.14 ppm (m, 1H, CH—O), 36-31 ppm (a plurality of multiplets, 10H, CH$_2$O and CH$_2$N signals), 2.32 ppm (s, 3H, Ar—CH$_3$).

Example II-1

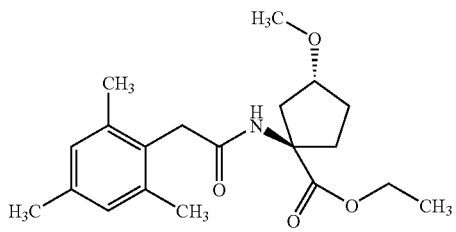

0.41 g according to Example II-10 (1.23 mmol) is dissolved in 15 ml of dichloromethane. 0.29 g of 1,8-bisdimethylaminonaphthalene (1.1 eq) and 0.20 g of trimethyloxonium tetrafluoroborate (1.1 eq) are added, and the mixture is stirred at room temperature. Then, in each case after 4 hours, once 0.3 eq each of trimethyloxonium tetrafluoroborate and 1,8-bismethylaminonaphthalene are added, and the mixture is again stirred overnight. 20 ml of 5% strength citric acid are then added, the mixture is stirred for 45 min, and the organic phase is separated off, dried with sodium sulfate and purified chromatographically on silica gel (gradient n-heptane/ethyl acetate 4:1 to ethyl acetate).

This gives 0.27 g of product (63% of theoretical yield).

$^1$H-NMR (400 MHz, CDCl$_3$) δ=4.16 (q, 2H, CH—OCH$_2$), 3.93 (m, 1H, CH—OCH$_3$), 3.56 (s, 2H, CH$_2$—Ar), 3.26 (s, 3H, OCH$_3$) ppm.

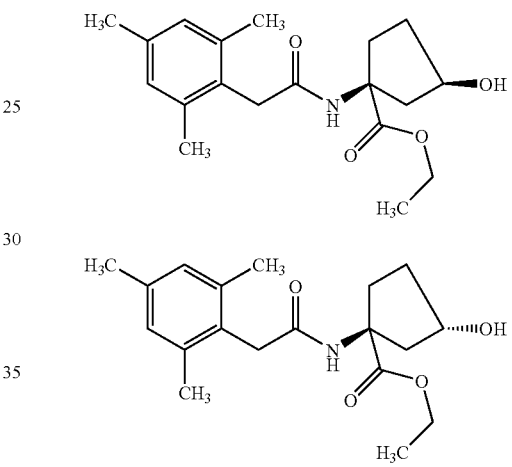

1.05 g of mesityleneacetic acid (5.89 mmol), 6 ml of thionyl chloride and two drops of N,N-dimethylformamide are heated to the boil under reflux. After the formation of gas has ceased, the mixture is concentrated and taken up in 20 ml of dichloromethane (solution 1). 1.25 g of triethylamine (2.1 eq) are added to a solution of ethyl 3-hydroxy-1-aminocyclopentanecarboxylate (5.89 mmol), and the mixture is stirred for 10 min. At room temperature, solution 1 is added dropwise over a period of 20 min. The mixture is allowed to stir at room temperature overnight. The mixture is washed with 15 ml of water, and the organic phase is dried with sodium sulfate and purified by column chromatography on silica gel (gradient ethyl acetate/n-heptane 0:100 to 100:0). This gives 0.95 g of cis-isomer (yield 48% of theory) and 0.43 g of trans-isomers (yield 22% of theory).

trans-isomer Ex. II-10

$^1$H-NMR (400 MHz, CDCl$_3$) δ=4.38 (m, 1H, CHOH), 3.53 (s, 2H, Ar—CH$_2$) ppm.

cis-isomer Ex. II-9

$^1$H-NMR (400 MHz, CDCl$_3$) δ=4.21 ppm (m, 1H, CHOH), 3.60 (s, 2H, Ar—CH$_2$) ppm.

Example II-34

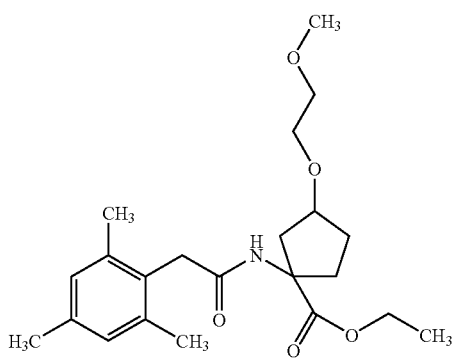

1.87 g of mesitylacetic acid and 6.25 g of thionyl chloride are initially charged, and 2 drops of dimethylformamide are added. The mixture is then heated until the evolution of gas has ceased, concentrated and dissolved in 25 ml of dichloromethane (solution 1). 2.49 of the compound according to Example (XIV-2) are dissolved in 25 ml of dichloromethane, and 3.06 ml of triethylamine are added, solution 1 is then added dropwise over a period of 30 min and the mixture is stirred at room temperature overnight. Half-concentrated sodium chloride solution is added, the phases are separated and the organic phase is concentrated, dried with sodium sulfate and purified by column chromatography (gradient ethyl acetate/heptane 5:95 to 70:30 ethyl acetate).

Yield: 1.91 g (38% of theory).

$^1$H-NMR (400 MHz, CDCl$_3$) δ=6.89 ppm (d, 1H, Ar—H)

3.35 ppm (d, 3H, OCH$_3$)

1.24 ppm (t, 3H, CH$_3$—CH$_2$O).

Analogously to Examples (II-1), (II-9), (II-10) and (II-34) and in accordance with the general statements on the preparation, the following compounds of the formula (II) are obtained:

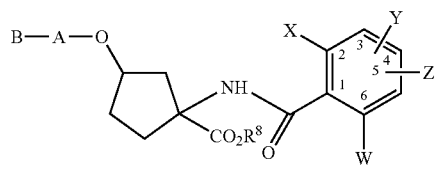

(II)

| Ex.-No. | W | X | Y | Z | A | B | R$^8$ | M.p. ° C. | Isomer |
|---|---|---|---|---|---|---|---|---|---|
| II-2 | OCH$_3$ | C$_2$H$_5$ | 4-Cl | H | CH$_2$ | H | C$_2$H$_5$ | oil<br>*3.07 (s, 3 H, CHOCH$_3$)<br>3.55 (s, 2 H, ArCH$_2$—CO)<br>3.84 (m, 1 H, CH—OCH$_3$)<br>and s, 3 H, Ar—OCH$_3$)<br>4.13 (q, 2 H, O—CH$_2$—CH$_3$) | cis |
| II-3 | CH$_3$ | CH$_3$ | 4-CH$_3$ | H | CH$_2$ | H | C$_2$H$_5$ | oil<br>*3.01 (s, 3 H, CH—OCH$_3$)<br>3.52 (s, 2 H, Ar—CH$_2$—CO)<br>3.81 (m, 1 H, CH—OCH$_3$)<br>4.16 (q, 2 H, O—CH$_2$—CH$_3$) | cis |
| II-4 | C$_2$H$_5$ | Br | 4-CH$_3$ | H | CH$_2$ | H | C$_2$H$_5$ | oil<br>*3.05 (m, 3 H, CHOCH$_3$)<br>3.76 (s, 2 H, Ar—CH$_2$—CO)<br>3.84, (m, 1 H, CHOCH$_3$)<br>4.16 (q, 2 H, O—CH$_2$—CH$_3$) | cis |
| II-5 | C$_2$H$_5$ | Br | 4-CH$_3$ | H | CH$_2$ | H | C$_2$H$_5$ | oil<br>*3.29 (s, 3 H, CH—OCH$_3$)<br>3.75 (s, 2 H, Ar—CH$_2$—CO)<br>4.03, (m, 1 H, CH—OCH$_3$)<br>4.16 (q, 1 H, O—CH$_2$—CH$_3$) | trans |
| II-6 | OCH$_3$ | C$_2$H$_5$ | 4-Cl | H | CH$_2$ | H | C$_2$H$_5$ | oil<br>was converted without further characterization into Ex. No. I-1-a-4 | trans |
| II-7 | C$_2$H$_5$ | Br | 4-CH$_3$ | H | CH$_2$ | CH$_3$ | C$_2$H$_5$ | oil<br>*3.29 (s, 2 H, CH—OCH$_2$—CH$_3$)<br>3.76 (s, 2 H, Ar—CH$_2$—CO)<br>3.95, (m, 1 H, CH—O—CH$_2$CH$_3$)<br>4.15 (q, 2 H, O—CH$_2$—CH$_3$) | cis |
| II-8 | C$_2$H$_5$ | Br | 4-CH$_3$ | H | CH$_2$ | CH$_3$ | C$_2$H$_5$ | oil<br>*3.43 (s, 2 H, CH—OCH$_2$—CH$_3$)<br>3.75 (s, 2 H, Ar—CH$_2$—CO)<br>4.14, (m, 2 H + 1 H,<br>CH—OCH$_2$CH$_3$ and O—CH$_2$—CH$_3$) | trans |
| II-9 | CH$_3$ | CH$_3$ | 4-CH$_3$ | H | — | H | C$_2$H$_5$ | see procedure | cis |
| II-10 | CH$_3$ | CH$_3$ | 4-CH$_3$ | H | — | H | C$_2$H$_5$ | see procedure | trans |
| II-11 | C$_2$H$_5$ | Br | 4-CH$_3$ | H | — | H | C$_2$H$_5$ | oil<br>*3.80 (s, 2 H, Ar—CH$_2$—CO)<br>4.36 (m, 1 H CH—OH) | cis |

-continued

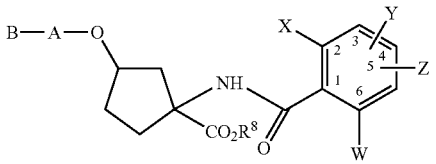
(II)

| Ex.-No. | W | X | Y | Z | A | B | R⁸ | M.p. °C. | Isomer |
|---|---|---|---|---|---|---|---|---|---|
| II-12 | C₂H₅ | Br | 4-CH₃ | H | — | H | C₂H₅ | oil<br>*3.76 (s, 2 H, Ar—CH₂CO)<br>4.43 (m, 1 H CH—OH) | trans |
| II-13 | OCH₃ | C₂H₅ | 4-Cl | H | — | H | C₂H₅ | oil<br>*3.60 (s, 2 H, Ar—CH₂—CO)<br>4.34 (m, 1 H CH—OH) | cis |
| II-14 | OCH₃ | C₂H₅ | 4-Cl | H | — | H | C₂H₅ | oil<br>*3.55 (s, 2 H, Ar—CH₂—CO)<br>4.43 (m, 1 H CH—OH) | trans |
| II-15 | CH₃ | CH₃ | 4-CH₃ | H | CH₂ | CH₃ | C₂H₅ | oil<br>*6.86 ppm (in each case s, 1 H, Ar—H), 1.25 and 0.99 ppm (in each case t, 3 H, CH₃—CH₂O) | cis |
| II-16 | CH₃ | CH₃ | 4-CH₃ | H | CH₂ | CH₃ | C₂H₅ | oil<br>*6.86 ppm (in each case s, 1 H, Ar—H), 1.24 and 1.15 ppm (in each case t, 3 H, CH₃—CH₂O) | trans |
| II-17 | CH₃ | Br | 4-CH₃ | H | — | H | C₂H₅ | oil<br>*7.28 and 6.99 ppm (in each case s, 1 H, Ar—H), 4.36 ppm (m, 1 H, CH—O), 4.15 ppm (m, 2 H, CH₂—O) | cis |
| II-18 | CH₃ | Br | 4-CH₃ | H | — | H | C₂H₅ | oil<br>*7.28 and 6.99 ppm (in each case s, 1 H, Ar—H), 4.44 ppm (m, 1 H, CH—O), 4.16 ppm (m, 2 H, CH₂—O) | trans |
| II-19 | CH₃ | Br | 4-CH₃ | H | CH₂ | H | C₂H₅ | oil<br>*7.24 and 6.99 ppm (in each case s, 1 H, Ar—H), 4.16 ppm (m, 2 H, CH₂—O), 3.84 ppm (m, 1 H, CH—OCH₃) | cis |
| II-20 | CH₃ | Cl | 4-CH₃ | H | — | H | C₂H₅ | oil<br>*7.13 and 6.96 ppm (in each case s, 1 H, Ar—H), 4.35 ppm (m, 1 H, CH—O), 4.16 ppm (m, 2 H, CH₂—O) | cis |
| II-21 | CH₃ | Cl | 4-CH₃ | H | — | H | C₂H₅ | solidified foam<br>*7.13 and 6.96 ppm (in each case s, 1 H, Ar—H), 4.45 ppm (m, 1 H, CH₂—O), 4.16 ppm (m, 2 H, CH₂—O) | trans |
| II-22 | CH₃ | Cl | 4-CH₃ | H | CH₂ | H | C₂H₅ | 95-99 | cis |
| II-23 | CH₃ | CH₃ | 4-CH₃ | H | CH₂ | C₃H₇ | C₂H₅ | oil<br>*6.91 and 6.88 ppm (in each case s, 2 H in total, Ar—H), 4.16 ppm (m, 2 H, CH₂—O), 4.00 and 3.92 ppm (in each case m, 1 H in total, CH—O) | mixture cis/trans |
| II-24 | C₂H₅ | Br | 4-CH₃ | H | CH₂ | C₃H₇ | C₂H₅ | oil<br>*7.30 and 7.27 ppm (in each case s, 1 H in total, Ar—H), 7.00 and 6.99 ppm (in each case s, 1 H in total, AR—H), 4.16 ppm (m, 2 H, CH₂—O), 4.08 and 3.95 ppm (in each case m, 1 H in total CH—O) | mixture cis/trans |
| II-25 | H | CH₃ | 5-(4-Cl-Ph) | H | — | H | C₂H₅ | solidified foam<br>**4.43 ppm (m, 1 H, CH—CO)<br>4.16 (m, 2 H CH₂—O), 2.34 (s, 3 H, Ar—CH₃) | trans |
| II-26 | H | CH₃ | 5-(4-Cl-Ph) | H | — | H | C₂H₅ | solidified foam<br>**4.37 ppm (m, 1 H, CH—CO)<br>4.16 (m, 2 H CH₂—O), 2.34 (s, 3 H, Ar—CH₃) | cis |
| II-27 | H | CH₃ | 5-(4-Cl-Ph) | H | CH₂ | H | C₂H₅ | solidified foam<br>**4.16 ppm (m, 2 H, CH₂—O)<br>4.03 ppm (m, 1 H CH—O), 2.36 (s, 3 H, Ar—CH₃) | trans |

-continued

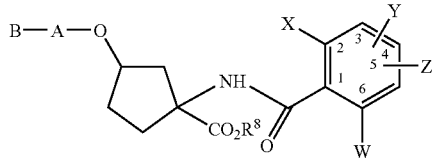

(II)

| Ex.-No. | W | X | Y | Z | A | B | R⁸ | M.p. °C. | Isomer |
|---|---|---|---|---|---|---|---|---|---|
| II-28 | H | $CH_3$ | 5-(4-Cl-Ph) | H | $CH_2$ | H | $C_2H_5$ | oil<br>**4.16 ppm (m, 2 H, $CH_2$—O)<br>3.82 ppm (m, 1 H CH—O), 2.37 (s,<br>3 H, Ar—$CH_3$) | cis |
| II-29 | $CH_3$ | $CH_3$ | 4-$CH_3$ | H | $CH_2$ | $C_2H_5$ | $C_2H_5$ | oil<br>*6.91 and 6.88 ppm (in each case s,<br>2 H in total, Ar—H), 4.16 ppm (m,<br>2 H, $CH_2$—O), 4.01 and 3.90 (in<br>each case m, 1 H in total, CH—O) | mixture<br>cis/trans |
| II-30 | $C_2H_5$ | Br | 4-$CH_3$ | H | $CH_2$ | $C_2H_5$ | $C_2H_5$ | oil<br>*7.30 and 7.27 ppm (in each case s,<br>1 H in total, Ar—H), 7.00 and 6.99<br>ppm (in each case s, 1 H in total,<br>AR—H), 4.16 ppm (m, 2 H, $CH_2$—O),<br>4.09 and 3.93 (in each case m,<br>1 H in total CH—O) | mixture<br>cis/trans |
| II-31 | $CH_3$ | $CH_3$ | 4-$CH_3$ | H | $CH_2$ | cyclopropyl | $C_2H_5$ | oil<br>*6.88 ppm (d, 1 H, Ar—H), 1.25 ppm<br>(t, 3 H, $CH_3$—$CH_2$O), 0.51 ppm (m,<br>2 H, CH (Cyclopropyl)) | mixture<br>cis/trans |
| II-32 | $C_2H_5$ | Br | 4-$CH_3$ | H | $CH_2$ | cyclopropyl | $C_2H_5$ | oil<br>*2.30 ppm (d, 2 H, Ar—$CH_3$),<br>1.25 ppm (m, 6 H, $CH_3$—$CH_2$O) and<br>Ar—$CH_2$—$CH_3$), 0.49 ppm (m, 2 H,<br>CH (Cyclopropyl)) | mixture<br>cis/trans |
| II-33 | H | $CH_3$ | 5-(4-Cl-Ph) | H | $CH_2$ | cyclopropyl | $C_2H_5$ | oil<br>*2.35 ppm (d, 2 H, Ar—$CH_3$),<br>1.25 ppm (m, 3 H, $CH_3$—$CH_2$O) 0.50<br>and 0.40 ppm (in each case m, 2 H<br>in total CH (Cyclopropyl)) | mixture<br>cis/trans |
| II-34 | $CH_3$ | $CH_3$ | 4-$CH_3$ | H | —$(CH_2)_2$— | $OCH_3$ | $C_2H_5$ | oil<br>*6.89 ppm (d, 1 H, Ar—H), 3.35 ppm<br>(d, 3 H, $OCH_3$), 1.24 ppm (t, 3 H,<br>$CH_3$—$CH_2$O) | mixture<br>cis/trans |
| II-35 | $C_2H_5$ | Br | 4-$CH_3$ | H | —$(CH_2)_2$— | $OCH_3$ | $C_2H_5$ | oil<br>**3.37 ppm (s, 3 H, $OCH_3$), 2.30<br>ppm (d, 3 H, Ar—$CH_3$), 1.24 ppm (m,<br>6 H, $CH_3$—$CH_2$O and Ar—$CH_2CH_3$) | mixture<br>cis/trans |
| II-36 | $CH_3$ | $CH_3$ | 4-Br | H | — | H | $C_2H_5$ | wax<br>*4.41 ppm (m, 1 H, CH—OH), 4.18<br>ppm (m, 2 H, $CH_2$—O), 3.52 (s, 2 H,<br>Ar—$CH_2$) | trans |

-continued

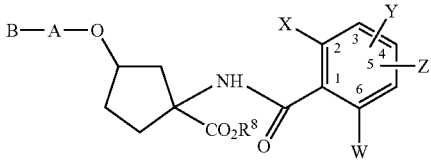

(II)

| Ex.-No. | W | X | Y | Z | A | B | $R^8$ | M.p. °C. | Isomer |
|---|---|---|---|---|---|---|---|---|---|
| II-37 | $CH_3$ | $CH_3$ | 4-Br | H | — | H | $C_2H_5$ | wax *4.37 ppm (m, 1 H, CH—OH), 4.15 ppm (m, 2 H, $CH_2$—O) | cis |

*$^1$H-NMR (400 MHz, $CDCl_3$): shift δ in ppm
**$^1$H-NMR (300 MHz, $CDCl_3$): shift δ in ppm
Ph = phenyl Ethyl 3-hydroxy-1-amino-1-cyclopentanecarboxylate

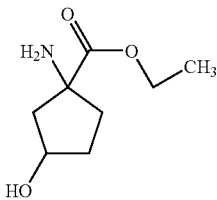

analogously to WO 02/46128

9.188 g sodium hydride (60%, 2.2. eq) are suspended in 400 ml of anhydrous tetrahydrofuran, and 27.914 g of ethyl N-(diphenylmethyleneglycinate (1 e.q.) in 100 ml of tetrahydrofuran are added dropwise over a period of 30 min. The mixture is stirred for 30 min, and dibromide A*, dissolved in 100 ml of tetrahydrofuran, is then added dropwise over a period of 30 min. The mixture is stirred initially under reflux for 4 h and then at room temperature overnight.

0.6 l of water and 1.2 l of acetic acid are then added, and the solution is allowed to stir at an internal temperature of 55° C. for 8 h. The mixture is allowed to stand overnight and then concentrated, 0.6 l of water is added, the pH is adjusted with sodium bicarbonate to pH=7 and the mixture is again concentrated. Three times, in each case 0.4 l of dichloromethane is added to the residue obtained in this manner, and the combined organic phases are dried with sodium sulfate. This gives 9.8 g of product as a viscous oil. (54.2% of theoretical yield)

$^1$H-NMR ($CDCl_3$, 400 MHz): δ=4.20 (m, 2H, $OCH_2$), 4.35 and 4.50 (in each case m, together 1H, CH—OH) ppm.

*Dibromide A=1,4-dibromo-2-(2'-tetrahydropyranyl)oxybutane

Ethyl 3-methoxy-1-amino-1-cyclopentanecarboxylate (XIV-1)

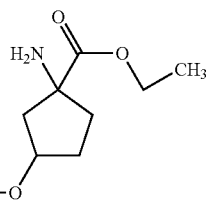

analogously to A. Börner et. al, Chem. Ber. 128, 767 (1995)
Ma, Dawei et. al., Tetrahedron Asymmetry 8, 825 (1997)

0.637 g of sodium hydride (60%, 2.2. eq) is suspended in 20 ml of anhydrous tetrahydrofuran, and 1.935 g of ethyl N-(diphenylmethyleneglycinate (1 e.q.), dissolved in 100 ml of tetrahydrofuran, are added dropwise over a period of 30 min. The mixture is allowed to stir for 30 min, and bismesylate A*, dissolved in 10 ml of tetrahydrofuran, is then added over a period of 30 min. The mixture is stirred initially at reflux for 4 h and then at room temperature overnight.

40 ml of water and 80 ml of acetic acid are then added to the solution, and the mixture is allowed to stir at an internal temperature of 55° C. for 8 h. The mixture is allowed to stand overnight and then concentrated, 50 ml of water are added, the pH is adjusted with sodium bicarbonate to pH=7 and the mixture is concentrated again. Three times, in each case 0.1 l of dichloromethane is added to the residue obtained, and the combined organic phases are dried with sodium sulfate. This gives 0.75 g of product as a viscous oil. (52.7% of theoretical yield).

*Bismesylate A=2-methoxy-1,4-butanediol-bismesylate

Analogously to Example (XIV-1) and in accordance with the general statements on the preparation, the following compounds of the formula (XIV) are obtained:

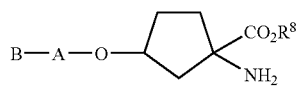

(XIV)

| Ex.-No. | A | B | $R^8$ | M.p. °C. | Isomer |
|---|---|---|---|---|---|
| XIV-2 | $(CH_2)_2$ | $OCH_3$ | $C_2H_5$ | oil was directly reacted further | mixture cis/trans |

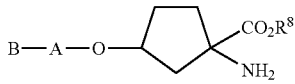

(XIV)

| Ex.-No. | A | B | R⁸ | M.p. °C. | Isomer |
|---|---|---|---|---|---|
| XIV-3 | CH₂ | △ | C₂H₅ | oil<br>0.52 (m, 1 H, CH-cyclopropyl, 1.28 ppm (m, 3 H, O—CH₂—CH₃), 3.24 ppm (m, 2 H, O—CH₂-cyclopropyl) | mixture cis/trans |
| XIV-4 | CH₂ | CH₃ | C₂H₅ | oil<br>was directly reacted further | mixture cis/trans |
| XIV-5 | CH₂ | C₂H₅ | C₂H₅ | oil<br>4.18 ppm (m, 2 H, CH₂—O), 4.18 and 4.01 ppm (in each case m, 1 H in total, CH—O), 3.39 ppm (m, 2 H, OCH₂) | mixture cis/trans |
| XIV-6 | CH₂ | C₃H₇ | C₂H₅ | oil<br>4.18 ppm (m, 2 H, CH₂—O), 4.18 and 4.01 ppm (in each case m, 1 H in total, CH—O), 3.39 ppm (m, 2 H, OCH₂) | mixture cis/trans |

*¹H-NMR (300 MHz, CDCl₃): shift δ in ppm

Use Examples

Example 1

Phaedon Test (PHAECO Spray Treatment)

| Solvents: | 78 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration.

Disks of Chinese cabbage (*Brassica pekinensis*) are sprayed with an active compound preparation of the desired concentration and, after drying, populated with larvae of the mustard beetle (*Phaedon cochleariae*).

After the desired period of time, the effect in % is determined. 100% means that all beetle larvae have been killed; 0% means that none of the beetle larvae have been killed.

In this test, for example, the following compounds of the Preparation Examples show, at an application rate of 500 g/ha, an efficacy of ≧80%: I-1-a-1, I-1-a-2, I-1-a-6, I-1-a-9, I-1-a-10, I-1-a-13, I-1-a-16, I-1-a-17, I-1-a-18, I-1-b-5, I-1-c-4, I-1-c-5, I-1-c-6, I-1-c-10, I-1-c-13, I-1-c-14, I-1-c-15, I-1-c-16, I-1-c-17, I-1-c-20.

Example 2

Myzus Test (MYZUPE Spray Treatment)

| Solvents: | 78 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration.

Disks of Chinese cabbage (*Brassica pekinensis*) which are infested by all stages of the green peach aphid (*Myzus persicae*) are sprayed with an active compound preparation of the desired concentration.

After the desired period of time, the effect in % is determined. 100% means that all aphids have been killed; 0% means that none of the aphids have been killed.

In this test, for example, the following compounds of the Preparation Examples show, at an application rate of 500 g/ha, an efficacy of ≧80%: I-1-a-1, I-1-a-2, I-1-a-3, I-1-a-6, I-1-a-7, I-1-a-9, I-1-a-10, I-1-a-11, I-1-a-12, I-1-a-13, I-1-a-15, I-1-a-16, I-1-a-17, I-1-a-18, I-1-a-19, I-1-a-21, I-1-a-22, I-1-a-24, I-1-a-25, I-1-a-26, I-1-b-1, I-1-b-2, I-1-b-5, I-1-c-2, I-1-c-3, I-1-c-4, I-1-c-5, I-1-c-6, I-1-c-8, I-1-c-14, I-1-c-15, I-1-c-16, I-1-c-17, I-1-c-19, I-1-c-20, I-1-c-22, I-1-c-23, I-1-c-24, I-1-c-25, I-1-c-26, I-1-c-27, I-1-c-28, I-1-c-29.

Example 3

*Spodoptera frugiperda* Test (SPODFR Spray Treatment)

| Solvents: | 78 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration.

Disks of maize leaves (*Zea mays*) are sprayed with an active compound preparation of the desired concentration and, after drying, populated with caterpillars of the armyworm (*Spodoptera frugiperda*).

After the desired period of time, the effect in % is determined. 100% means that all caterpillars have been killed; 0% means that none of the caterpillars have been killed.

In this test, for example, the following compounds of the Preparation Examples show, at an application rate of 500 g/ha, an efficacy of ≧80%: I-1-a-1, I-1-a-10, I-1-a-11, I-1-a-16, I-1-a-25, I-1-a-26, I-1-b-5, I-1-c-6, I-1-c-15, I-1-c-16, I-1-c-20.

Example 4

Tetranychus Test; OP Resistant (TETRUR Spray Treatment)

| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Disks of bean leaves (*Phaseolus vulgaris*) which are infested by all stages of the greenhouse rat spider mite (*Tetranychus urticae*) are sprayed with an active compound preparation of the desired concentration.

After the desired period of time, the effect in % is determined. 100% means that all spider mites have been killed; 0% means that none of the spider mites have been killed.

In this test, for example, the following compounds of the Preparation Examples show, at an application rate of 100 g/ha, an efficacy of ≧80%: I-1-a-10 I-1-a-21, I-1-a-22, I-1-a-24, I-1-a-25, I-1-a-26, I-1-b-1, I-1-b-4, I-1-b-5, I-1-c-3, I-1-c-4, I-1-c-5, I-1-c-13, I-1-c-14, I-1-c-15, I-1-c-16, I-1-c-20, I-1-c-21, I-1-c-22, I-1-c-23, I-1-c-24, I-1-c-25, I-1-c-26, I-1-c-27, I-1-c-28, I-1-c-29.

Example 5

Herbicidal Pre-Emergence Action

Seeds of monocotyledonous and dicotyledonous weed and crop plants are placed in sandy loam in wood fibre pots and covered with soil. The test compounds, formulated in the form of wettable powders (WP) or as emulsion concentrates (EC), are then, as an aqueous suspension with a water application rate of 800 l/ha (converted), with 0.2% of wetting agent added, applied to the surface of the covering soil.

After the treatment, the pots are placed in a greenhouse and kept under good growth conditions for the test plants. The visual assessment of the damage on the test plants is carried out after a trial period of 3 weeks by comparison with untreated controls (herbicidal activity in percent (%): 100% activity=the plants have died, 0% activity=like control plants).

Applied by the pre-emergence method at 320 g of a.i./ha, the following compounds show an efficacy of ≧80% against *Lolium multiflorum* and *Setaria viridis*: I-1-a-2, I-1-a-8.

Applied by the pre-emergence method at 320 g of a.i./ha, the following compounds show an efficacy of ≧80% against *Lolium multiflorum* and *Echinohcloa crus-gali*: I-1-a-2, I-1-a-3, I-1-a-5, I-1-a-6, I-1-a-7, I-1-a-10, I-1-a-11, I-1-a-12, I-1-a-19, I-1-a-20, I-1-b-2, I-1-b-3, I-1-b-4, I-1-c-1, I-1-c-2, I-1-c-3, I-1-c-7, I-1-c-9, I-1-c-10, I-1-c-11, I-1-c-15, I-1-c-16, I-1-c-18, I-1-c-20.

Herbicidal Post-Emergence Action

Seeds of monocotyledonous and dicotyledonous weed and crop plants are placed in sandy loam in wood fibre pots, covered with soil and cultivated in a greenhouse under good growth conditions. 2 to 3 weeks after sowing, the test plants are treated at the one-leaf stage. The test compounds, formulated as wettable powders (WP) or as emulsion concentrates (EC), are then, with a water application rate of 800 l/ha (converted), with 0.2% of wetting agent added, sprayed onto the green parts of the plants as an aqueous suspension. After the test plants have been kept in the greenhouse under optimum growth conditions for about 3 weeks, the activity of the preparations is rated visually in comparison to treated controls (herbicidal activity in percent (%): 100% activity=the plants have died, 0% activity=like control plants).

Applied by the post-emergence method at 320 g of a.i./ha, the following compounds show an efficacy of ≧80% against *Avena fatua, Lolium multiflorum* and *Setaria viridis* and *Echinochloa crus-galli*: I-1-a-2, I-1-a-3, I-1-a-7, I-1-a-8, I-1-a-12, I-1-a-20, I-1-b-2, I-1-b-3, I-1-c-1, I-1-c-2, I-1-c-11, I-1-c-20.

Example 6

Herbicidal Post-Emergence Action

Seeds of monocotyledonous and dicotyledonous weed and crop plants are placed into sandy loam in wood fiber pots or in plastic pots, covered with soil and cultivated in a greenhouse, during the vegetation period also outdoors outside of the greenhouse, under good growth conditions. 2 to 3 weeks after sowing, the test plants are treated at the one- to three-leaf stage. The test compounds, formulated as wettable powders (WP) or liquid (EC), are, in various dosages at a water application rate of 300 l/ha (converted), with wetting agent (0.2 to 0.3%) added, sprayed onto the plants and the surface of the soil. 3 to 4 weeks after the treatment of the test plants, the effect of the preparations is rated visually in comparison to untreated controls (herbicidal effect in percent (%): 100% effect=the plants have died, 0% effect=like control plants).

Use of Safeners

If it is additionally to be tested as to whether safeners can improve the plant compatibility of test substances in the case of crop plants, the following options are used for applying the safener:

seeds of the crop plants are, before sowing, dressed with the safener substance (the amount of safener stated in percent, based on the weight of the seed)

before the application of the test substances, the crop plants are sprayed with the safener at a certain application rate per hectare (usually 1 day before the application of the test substances)

the safener is applied together with the test substance as a tank mix (the amount of safener is stated in g/ha or as a ratio, based on the herbicide).

By comparing the effect of test substances on crop plants without or with safener treatment, it is possible to assess the effect of the safener substance.

Container Trials with Cereal Outdoors ('Bird Cage')

Mefenpyr 1 Day Prior to Herbicide Application

|  | Application rate g ai/ha | Summer barley after 28 d observed (%) |
|---|---|---|
| Example (I-1-c-2) | 50 | 90 |
|  | 25 | 65 |
| Example (I-1-c-2) + mefenpyr | 50 + 100 | 30 |
|  | 25 + 100 | 15 |

-continued

| | Application rate g ai/ha | Summer wheat after 10 d observed (%) |
|---|---|---|
| Example (I-1-a-4) | 50 | 40 |
| | 25 | 25 |
| Example (I-1-a-4) + mefenpyr | 50 + 100 | 20 |
| | 25 + 100 | 10 |

| | Application rate g ai/ha | Summer wheat after 28 d observed (%) |
|---|---|---|
| Example (I-1-a-3) | 50 | 70 |
| | 25 | 40 |
| Example (I-1-a-3) + mefenpyr | 50 + 100 | 30 |
| | 25 + 100 | 20 |

Container Trials with Cereal in the Greenhouse and Outdoors ('Bird Cage')

Mefenpyr 1 Day Prior to Herbicide Application

| | 28 days after application | | |
|---|---|---|---|
| | Application rate g ai/ha | Summer barley observed (%) | Summer wheat observed (%) |
| Example (I-1-a-2) | 100 | 95 | 75 |
| | 50 | 70 | 70 |
| | 25 | 50 | 40 |
| Example (I-1-a-2) + mefenpyr | 100 + 100 | 50 | 30 |
| | 50 + 100 | 40 | 25 |
| | 25 + 100 | 30 | 20 |

| | 10 days after application | |
|---|---|---|
| | Application rate g ai/ha | Summer barley observed (%) |
| Example (I-1-a-3) | 50 | 70 |
| | 25 | 70 |
| | 12.5 | 60 |
| | 6.25 | 20 |
| Example (I-1-a-3) + mefenpyr | 50 + 100 | 40 |
| | 25 + 100 | 10 |
| | 12.5 + 100 | 5 |
| | 6.25 + 100 | 0 |

| | 28 days after application | |
|---|---|---|
| | Application rate g ai/ha | Summer wheat observed (%) |
| Example (I-1-c-2) | 50 | 70 |
| | 25 | 50 |
| | 12.5 | 30 |
| | 6.25 | 20 |
| Example (I-1-c-2) + mefenpyr | 50 + 100 | 20 |
| | 25 + 100 | 15 |
| | 12.5 + 100 | 10 |
| | 6.25 + 100 | 10 |

| | Application rate g ai/ha | Summer barley observed (%) | Summer wheat observed (%) |
|---|---|---|---|
| | 28 days after application | | |
| Example (I-1-a-5) | 25 | 85 | |
| | 12.5 | 70 | 80 |
| | 6.25 | 30 | 70 |
| | 3.125 | | 30 |
| Example (I-1-a-5) + mefenpyr | 25 + 100 | 60 | |
| | 12.5 + 100 | 30 | 60 |
| | 6.25 + 100 | 10 | 15 |
| | 3.125 + 100 | | 0 |

| | 10 days after application | | |
|---|---|---|---|
| Example (I-1-a-7) | 100 | 60 | 50 |
| | 50 | 60 | 50 |
| | 25 | 40 | 40 |
| Example (I-1-a-7) + mefenpyr | 100 + 100 | 15 | 10 |
| | 50 + 100 | 10 | 5 |
| | 25 + 100 | 5 | 3 |

Example 7

Heliothis virescens Test—Treatment of Transgenic Plants

| Solvent: | 7 parts by weight of acetone |
|---|---|
| Emulsifier: | 1 part by weight of alkylaryl polyglycol ether |

To produce a suitable preparation of active compound, 1 part by weight of active compound is mixed with the stated amounts of solvent and the stated amount of emulsifier, and the concentrate is diluted with water to the desired concentration.

Soybean shoots (Glycine max) of the cultivar Roundup Ready (trademark of Monsanto Comp. USA) are treated by being dipped into the preparation of active compound of the desired concentration and are populated with the tobacco bud worm Heliothis virescens while the leaves are still moist.

After the desired period of time, the kill of the insects is determined.

Example 8

Critical Concentration Test/Soil Insects—Treatment of Transgenic Plants

| Test insect: | Diabrotica balteata - larvae in the soil |
|---|---|
| Solvent: | 7 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil. Here, the concentration of active compound in the preparation is virtually immaterial; only the amount by weight of active compound per volume unit of soil, which is stated in ppm (mg/l), matters. The soil is filled into 0.25 l pots, and these are allowed to stand at 20° C.

Immediately after the preparation, 5 pregerminated maize corns of the cultivar YIELD GUARD (trademark of Monsanto Comp., USA) are placed into each pot. After 2 days, the appropriate test insects are placed into the treated soil. After a further 7 days, the efficacy of the active compound is determined by counting the maize plants that have emerged (1 plant=20% activity).

The invention claimed is:

1. A compound of formula (I)

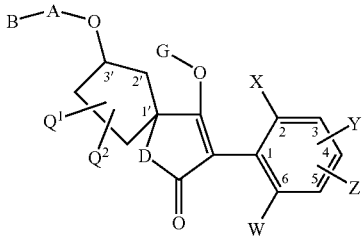

(I)

in which
W represents hydrogen, alkyl, alkenyl, alkynyl, halogen, alkoxy, haloalkyl, haloalkoxy or cyano,
X represents halogen, alkyl, alkenyl, alkynyl, alkoxy, alkoxyalkoxy, haloalkyl, haloalkoxy or cyano,
Y represents hydrogen, halogen, alkyl, alkenyl, alkynyl, alkoxy, cyano, haloalkyl, haloalkoxy, represents in each case optionally substituted phenyl or hetaryl,
Z represents hydrogen, halogen, alkyl, haloalkyl, cyano, alkoxy or haloalkoxy,
A represents an optionally substituted alkanediyl group or represents cycloalkyl which is optionally substituted and/or optionally interrupted by a heteroatom,
B represents hydrogen or in each case optionally substituted alkyl, alkenyl, alkoxy, alkoxy-alkoxy, phenyl, hetaryl or represents cycloalkyl which is optionally substituted and/or optionally interrupted by heteroatoms and/or C=O,
or A represents a bond and B represents hydrogen,
D represents NH or oxygen,
$Q^1$ represents hydrogen, represents in each case optionally substituted alkyl, alkoxy, alkoxyalkyl or alkylthioalkyl, represents in each case optionally substituted cycloalkyl in which optionally one methylene group is replaced by heteroatoms or represents optionally substituted phenyl, hetaryl, phenylalkyl or hetarylalkyl,
$Q^2$ represents hydrogen or alkyl,
$Q^1$ and $Q^2$ together with the carbon to which they are attached represent an optionally substituted $C_3$-$C_6$-ring which may optionally be interrupted by a heteroatom, or
$Q^1$ and $Q^2$ together with the carbon atoms to which they are attached represent an optionally substituted $C_3$-$C_6$-ring which may optionally be interrupted by a heteroatom,
G represents hydrogen (a) or represents one of the groups

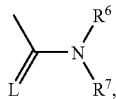

(b)

(c)

(d)

(e)

E, or (f)

(g)

 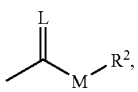 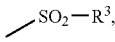 

in which
E represents a metal ion or an ammonium ion,
L represents oxygen or sulfur,
M represents oxygen or sulfur,
$R^1$ represents in each case optionally halogen- or cyano-substituted alkyl, alkenyl, alkoxyalkyl, alkylthioalkyl or polyalkoxyalkyl or represents in each case optionally halogen-, alkyl- or alkoxy-substituted cycloalkyl or heterocyclyl or represents in each case optionally substituted phenyl, phenylalkyl, hetaryl, phenoxyalkyl or hetaryloxyalkyl,
$R^2$ represents in each case optionally halogen- or cyano-substituted alkyl, alkenyl, alkoxyalkyl or polyalkoxyalkyl or represents in each case optionally substituted cycloalkyl, phenyl or benzyl,
$R^3$, $R^4$ and $R^5$ independently of one another represent in each case optionally halogen-substituted alkyl, alkoxy, alkylamino, dialkylamino, alkylthio, alkenylthio or cycloalkylthio or represent in each case optionally substituted phenyl, benzyl, phenoxy or phenylthio,
$R^6$ and $R^7$ independently of one another represent hydrogen, represent in each case optionally halogen- or cyano-substituted alkyl, cycloalkyl, alkenyl, alkoxy, alkoxyalkyl, represent in each case optionally substituted phenyl or benzyl, or together with the N atom to which they are attached form an optionally substituted cycle which optionally contains oxygen or sulfur.

2. The compound of the formula (I) as claimed in claim 1 in which
W represents hydrogen, $C_1$-$C_6$-alkyl, $C_2$-$C_6$-alkenyl, $C_2$-$C_6$-alkynyl, halogen, $C_1$-$C_6$-alkoxy, $C_1$-$C_4$-haloalkyl, $C_1$-$C_4$-haloalkoxy or cyano,
X represents halogen, $C_1$-$C_6$-alkyl, $C_2$-$C_6$-alkenyl, $C_2$-$C_6$-alkynyl, $C_1$-$C_6$-alkoxy, $C_1$-$C_6$-alkoxy-$C_1$-$C_4$-alkoxy, $C_1$-$C_4$-haloalkyl, $C_1$-$C_4$-haloalkoxy or cyano,
Y represents hydrogen, halogen, $C_1$-$C_6$-alkyl, $C_2$-$C_6$-alkenyl, $C_2$-$C_6$-alkynyl, $C_2$-$C_6$-alkoxy, cyano, $C_1$-$C_4$-haloalkyl, haloalkoxy, represents $V^1$- and $V^2$-substituted phenyl or pyridyl,
$V^1$ represents halogen, $C_1$-$C_{12}$-alkyl, $C_1$-$C_6$-alkoxy, $C_1$-$C_4$-haloalkyl, $C_1$-$C_4$-haloalkoxy, cyano or nitro,
$V^2$ represents hydrogen, halogen, $C_1$-$C_6$-alkyl, $C_1$-$C_6$-alkoxy or $C_1$-$C_4$-haloalkyl,
$V^1$ and $V^2$ together represent $C_3$-$C_4$-alkanediyl which may optionally be substituted by halogen and/or $C_1$-$C_2$-alkyl and which may optionally be interrupted by one or two oxygen atoms,
Z represents hydrogen, halogen, $C_1$-$C_6$-alkyl, $C_1$-$C_4$-haloalkyl, cyano, $C_1$-$C_6$-alkoxy or $C_1$-$C_4$-haloalkoxy,
A represents an optionally $C_1$-$C_4$-alkyl-substituted $C_1$-$C_4$-alkanediyl group or represents optionally $C_1$-$C_4$-alkyl-substituted $C_5$-$C_8$-cycloalkyl in which optionally one methylene group is replaced by oxygen,
B represents hydrogen or represents in each case optionally halogen-substituted $C_1$-$C_8$-alkyl, $C_2$-$C_8$-alkenyl, $C_1$-$C_6$-alkoxy, $C_1$-$C_6$-alkoxy-$C_1$-$C_4$-alkoxy, $C_1$-$C_4$-alkoxy-bis-$C_1$-$C_4$-alkoxy, represents optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl, represents optionally halogen-, $C_1$-$C_4$-alkyl- or $C_1$-$C_2$-haloalkyl-substituted pyridyl, pyrimidyl, thiazolyl or thienyl or represents optionally halogen-, $C_1$-$C_4$-alkyl-, $C_1$-$C_4$-alkoxy- or $C_1$-$C_2$-haloalkyl-substituted $C_3$-$C_8$-cycloalkyl in which optionally one or two not directly adjacent methylene groups are replaced by oxygen, two methylene groups are replaced by the radical —O—CO— or three methylene groups are replaced by the radical —O—CO—O—, or A represents a bond and B represents hydrogen, D represents NH or oxygen, $Q^1$ represents hydrogen or represents in each case optionally halogen-substituted $C_1$-$C_6$-alkyl, $C_1$-$C_6$-alkoxy, $C_1$-$C_4$-alkoxy-$C_1$-$C_4$-alkyl, $C_1$-$C_4$-alkylthio-$C_1$-$C_4$-alkyl or represents optionally halogen-, $C_1$-$C_4$-alkyl- or $C_1$-$C_4$-alkoxy-substituted $C_3$-$C_6$-cycloalkyl in which optionally one methylene group is replaced by oxygen or represents phenyl, phenyl-$C_1$-$C_2$-alkyl or hetaryl, each of which is optionally mono- or disubstituted by halogen, $C_1$-$C_4$-alkyl, $C_1$-$C_4$-alkoxy, $C_1$-$C_4$-haloalkyl or $C_1$-$C_4$-haloalkoxy, $Q^2$ represents hydrogen or $C_1$-$C_6$-alkyl, or $Q^1$ and $Q^2$ together with the carbon to which they are attached represent a $C_3$-$C_6$-ring which is optionally mono- or disubstituted by fluorine, chlorine, $C_1$-$C_4$-alkyl, $C_1$-$C_4$-alkoxy or trifluoromethyl and in which optionally one methylene group may be replaced by oxygen, or $Q^1$ and $Q^2$ together with the carbon atoms to which they are attached represent a $C_3$-$C_6$-ring which is optionally mono- or disubstituted by fluorine, chlorine, $C_1$-$C_4$-alkyl, $C_1$-$C_4$-alkoxy or trifluoromethyl and in which optionally one methylene group may be replaced by oxygen, G represents hydrogen (a) or represents one of the groups

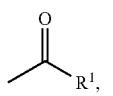

(b)

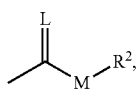

(c)

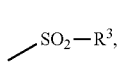

(d)

(e)

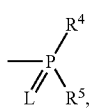

E, or (f)

(g)

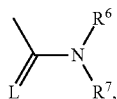

in which

E represents a metal ion or an ammonium ion,

L represents oxygen or sulfur and

M represents oxygen or sulfur, $R^1$ represents in each case optionally halogen- or cyano-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl or poly-$C_1$-$C_8$-alkoxy-$C_1$-$C_8$-alkyl or represents optionally halogen-, $C_1$-$C_6$-alkyl- or $C_1$-$C_6$-alkoxy-substituted $C_3$-$C_8$-cycloalkyl in which optionally one or two not directly adjacent methylene groups are replaced by oxygen and/or sulfur, or represents optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkylsulfonyl-substituted phenyl, or represents optionally halogen-, nitro-, cyano-, $C_1$-$C_6$-alkyl-, $C_1$-$C_6$-alkoxy-, $C_1$-$C_6$-haloalkyl- or $C_1$-$C_6$-haloalkoxy-substituted phenyl-$C_1$-$C_6$-alkyl, or represents optionally halogen- or $C_1$-$C_6$-alkyl-substituted 5- or 6-membered hetaryl having one or two heteroatoms from the group consisting of oxygen, sulfur and nitrogen, or represents optionally halogen- or $C_1$-$C_6$-alkyl-substituted phenoxy-$C_1$-$C_6$-alkyl or represents optionally halogen-, amino- or $C_1$-$C_6$-alkyl-substituted 5- or 6-membered hetaryloxy-$C_1$-$C_6$-alkyl having one or two heteroatoms from the group consisting of oxygen, sulfur and nitrogen, $R^2$ represents in each case optionally halogen- or cyano-substituted $C_1$-$C_{20}$-alkyl, $C_2$-$C_{20}$-alkenyl, $C_1$-$C_8$-alkoxy-$C_2$-$C_8$-alkyl or poly-$C_1$-$C_8$-alkoxy-$C_2$-$C_8$-alkyl, or represents optionally halogen-, $C_1$-$C_6$-alkyl- or $C_1$-$C_6$-alkoxy-substituted $C_3$-$C_8$-cycloalkyl or represents in each case optionally halogen-, cyano-, nitro-, $C_1$-$C_6$-alkyl-, $C_1$-$C_6$-alkoxy-, $C_1$-$C_6$-haloalkyl- or $C_1$-$C_6$-haloalkoxy-substituted phenyl or benzyl, $R^3$ represents optionally halogen-substituted $C_1$-$C_8$-alkyl or in each case optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl, $R^4$ and $R^5$ independently of one another represent in each case optionally halogen-substituted $C_1$-$C_8$-alkyl, $C_1$-$C_8$-alkoxy, $C_1$-$C_8$-alkylamino, di-($C_1$-$C_8$-alkyl)amino, $C_1$-$C_8$-alkylthio or $C_3$-$C_8$-alkenylthio or represent in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-halo-alkylthio-, $C_1$-$C_4$-alkyl- or $C_1$-$C_4$-haloalkyl-substituted phenyl, phenoxy or phenyl-thio, and $R^6$ and $R^7$ independently of one another represent hydrogen, represent in each case optionally halogen- or cyano-substituted $C_1$-$C_8$-alkyl, $C_3$-$C_8$-cycloalkyl, $C_1$-$C_8$-alkoxy, $C_3$-$C_8$-alkenyl or $C_1$-$C_8$-alkoxy-$C_2$-$C_8$-alkyl, represent in each case optionally halogen-, $C_1$-$C_8$-alkyl-, $C_1$-$C_8$-haloalkyl- or $C_1$-$C_8$-alkoxy-substituted phenyl or benzyl or together represent an optionally $C_1$-$C_6$-alkyl-substituted $C_3$-$C_6$-alkylene radical in which optionally one methylene group is replaced by oxygen or sulfur.

3. The compound of the formula (I) as claimed in claim 1 in which

W represents hydrogen, chlorine, bromine, iodine, $C_1$-$C_4$-alkyl, $C_2$-$C_4$-alkenyl, $C_2$-$C_4$-alkynyl, $C_1$-$C_4$-alkoxy, $C_1$-$C_2$-haloalkyl or $C_1$-$C_2$-haloalkoxy, X represents chlorine, bromine, iodine, $C_1$-$C_4$-alkyl, $C_2$-$C_4$-alkenyl, $C_2$-$C_4$-alkynyl, $C_1$-$C_4$-alkoxy, $C_1$-$C_4$-alkoxy-$C_1$-$C_3$-alkoxy, $C_1$-$C_2$-haloalkyl, $C_1$-$C_2$-haloalkoxy or cyano, Y in the 4-position represents hydrogen, fluorine, chlorine, bromine, iodine, methoxy, ethoxy, cyano, trifluoromethyl, difluoromethoxy or trifluoromethoxy, Z represents hydrogen; or W represents hydrogen, chlorine, bromine or $C_1$-$C_4$-alkyl, X represents chlorine, bromine, $C_1$-$C_4$-alkyl, $C_1$-$C_4$-alkoxy, $C_1$-$C_2$-haloalkyl, $C_1$-$C_2$-haloalkoxy or cyano, Y in the 4-position represents $C_2$-$C_4$-alkenyl, $C_2$-$C_4$-alkynyl or represents the radical

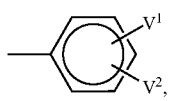

Z represents hydrogen, $V^1$ represents fluorine, chlorine, $C_1$-$C_4$-alkyl, $C_1$-$C_4$-alkoxy, $C_1$-$C_2$-haloalkyl or $C_1$-$C_2$-haloalkoxy, $V^2$ represents hydrogen, fluorine, chlorine, $C_1$-$C_4$-alkyl, $C_1$-$C_4$-alkoxy or $C_1$-$C_2$-haloalkyl, $V^1$ and $V^2$ together represent —O—$CH_2$—O— and —O—$CF_2$—O—; or W represents hydrogen, chlorine, bromine or $C_1$-$C_4$-alkyl, X represents chlorine, bromine, $C_1$-$C_4$-alkyl or $C_1$-$C_2$-haloalkyl, Y in the 5-position represents $C_2$-$C_4$-alkenyl, $C_2$-$C_4$-alkynyl, represents the radical

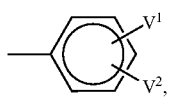

Z in the 4-position represents hydrogen, $C_1$-$C_4$-alkyl or chlorine, $V^1$ represents fluorine, chlorine, $C_1$-$C_4$-alkyl, $C_1$-$C_4$-alkoxy, $C_1$-$C_2$-haloalkyl or $C_1$-$C_2$-haloalkoxy, $V^2$ represents hydrogen, fluorine, chlorine, $C_1$-$C_4$-alkyl, $C_1$-$C_4$-alkoxy or $C_1$-$C_2$-haloalkyl, $V^1$ and $V^2$ together represent —O—$CH_2$—O— or —O—$CF_2$—O—; or W represents hydrogen, $C_1$-$C_4$-alkyl, $C_2$-$C_4$-alkenyl, $C_2$-$C_4$-alkynyl, $C_1$-$C_4$-alkoxy, chlorine, bromine, iodine or trifluoromethyl, X represents chlorine, bromine, iodine, $C_1$-$C_4$-alkyl, $C_2$-$C_4$-alkenyl, $C_2$-$C_4$-alkynyl, $C_1$-$C_4$-alkoxy, $C_1$-$C_4$-alkoxy-$C_1$-$C_3$-alkoxy, $C_1$-$C_2$-haloalkyl, $C_1$-$C_2$-haloalkoxy or cyano, Y in the 4-position represents $C_1$-$C_4$-alkyl, Z represents hydrogen; or W represents hydrogen, chlorine, bromine, iodine, $C_1$-$C_4$-alkyl or $C_1$-$C_4$-alkoxy, X represents chlorine, bromine, iodine, $C_1$-$C_4$-alkyl, $C_1$-$C_4$-alkoxy, $C_1$-$C_2$-haloalkyl, $C_1$-$C_2$-haloalkoxy or cyano, Y in the 4-position represents hydrogen, chlorine, bromine, $C_1$-$C_4$-alkyl, $C_1$-$C_2$-haloalkyl or $C_1$-$C_2$-haloalkoxy, Z in the 3- or 5-position represents fluorine, chlorine, bromine, iodine, $C_1$-$C_4$-alkyl, $C_1$-$C_2$-haloalkyl, $C_1$-$C_4$-alkoxy or $C_1$-$C_2$-haloalkoxy; and A represents an optionally $C_1$-$C_2$-alkyl-substituted $C_1$-$C_3$-alkanediyl group or represents $C_5$-$C_6$-cycloalkyl in which optionally one methylene group is replaced by oxygen, B represents hydrogen or $C_1$-$C_6$-alkyl, $C_2$-$C_6$-alkenyl, $C_1$-$C_4$-alkoxy, $C_1$-$C_4$-alkoxy-$C_1$-$C_3$-alkoxy, $C_1$-$C_4$-alkoxy-bis-$C_1$-$C_3$-alkoxy, each of which is optionally mono- to trisubstituted by fluorine or chlorine, represents phenyl which is optionally mono- to trisubstituted by fluorine, chlorine, bromine, $C_1$-$C_4$-alkyl, $C_1$-$C_4$-alkoxy, $C_1$-$C_2$-haloalkyl, $C_1$-$C_2$-haloalkoxy, cyano or nitro, represents pyridyl, pyrimidyl, thiazolyl or thienyl, each of which is optionally mono- or disubstituted by fluorine, chlorine, bromine, methyl, ethyl or trifluoromethyl or represents $C_3$-$C_6$-cycloalkyl which is optionally mono- or disubstituted by fluorine, chlorine, methyl, methoxy or trifluoromethyl, in which optionally one or two not directly adjacent methylene groups are replaced by oxygen, or A represents a bond and B represents hydrogen, D represents NH or oxygen, $Q^1$ represents hydrogen, represents $C_1$-$C_4$-alkyl which is optionally mono- to trisubstituted by fluorine, $Q^2$ represents hydrogen or $C_1$-$C_4$-alkyl, $Q^1$ and $Q^2$ together with the carbon atom to which they are attached represent a $C_3$-$C_6$-ring which is optionally monosubstituted by fluorine, methyl, methoxy or trifluoromethyl and in which one methylene group may be replaced by oxygen, or $Q^1$ and $Q^2$ together with the carbon atoms to which they are attached represent a $C_3$-$C_6$-ring which is optionally monosubstituted by fluorine, methyl, methoxy or trifluoromethyl and in which one methylene group may be replaced by oxygen, G represents hydrogen (a) or represents one of the groups

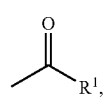
(b)

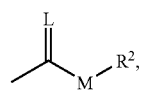
(c)

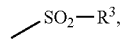
(d)

(e)

E, or
(f)

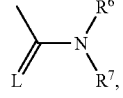
(g)

in which

E represents a metal ion or an ammonium ion,

L represents oxygen or sulfur and

M represents oxygen or sulfur, $R^1$ represents $C_1$-$C_{16}$-alkyl, $C_2$-$C_{16}$-alkenyl, $C_1$-$C_6$-alkoxy-$C_1$-$C_4$-alkyl, $C_1$-$C_6$-alkylthio-$C_1$-$C_4$-alkyl or poly-$C_1$-$C_6$-alkoxy-$C_1$-$C_4$-alkyl, each of which is optionally mono- to trisubstituted by fluorine or chlorine, or represents $C_3$-$C_7$-cycloalkyl which is optionally mono- to disubstituted by fluorine, chlorine, $C_1$-$C_5$-alkyl or $C_1$-$C_5$-alkoxy and in which optionally one or two not directly adjacent methylene groups are replaced by oxygen and/or sulfur, or represents phenyl which is optionally mono- to trisubstituted by fluorine, chlorine, bromine, cyano, nitro, $C_1$-$C_4$-alkyl, $C_1$-$C_4$-alkoxy, $C_1$-$C_3$-haloalkyl, $C_1$-$C_3$-haloalkoxy, $C_1$-$C_4$-alkylthio or $C_1$-$C_4$-alkylsulfonyl, or represents phenyl-$C_1$-$C_4$-alkyl which is optionally mono- to disubstituted by fluorine, chlorine, bromine, $C_1$-$C_4$-alkyl, $C_1$-$C_4$-alkoxy, $C_1$-$C_3$-haloalkyl or $C_1$-$C_3$-haloalkoxy, or represents pyrazolyl, thiazolyl, pyridyl, pyrimidyl, furanyl or thienyl, each of which is optionally mono- to disubstituted by fluorine, chlorine, bromine or $C_1$-$C_4$-alkyl, or represents phenoxy-$C_1$-$C_5$-alkyl which is optionally mono- to disubstituted by fluorine, chlorine, bromine or $C_1$-$C_4$-alkyl or represents pyridyloxy-$C_1$-$C_5$-alkyl, pyrimidyloxy-$C_1$-$C_{15}$-alkyl or thiazolyloxy-$C_1$-$C_5$-alkyl, each of which is optionally mono- to disubstituted by fluorine, chlorine, bromine, amino or $C_1$-$C_4$-alkyl, $R^2$ represents $C_1$-$C_{16}$-alkyl, $C_2$-$C_{16}$-alkenyl, $C_1$-$C_6$-alkoxy-$C_2$-$C_6$-alkyl or poly-$C_1$-$C_6$-alkoxy-$C_2$-$C_6$-alkyl, each of which is optionally mono- to trisubstituted by fluorine or chlorine, or represents $C_3$-$C_7$-cycloalkyl which is optionally mono- to disubstituted by fluorine, chlorine, $C_1$-$C_4$-alkyl or $C_1$-$C_4$-alkoxy or represents phenyl or benzyl, each of which is optionally mono- to trisubstituted by fluorine, chlorine, bromine, cyano, nitro, $C_1$-$C_4$-alkyl, $C_1$-$C_3$-alkoxy, $C_1$-$C_3$-haloalkyl or $C_1$-$C_3$-haloalkoxy, $R^3$ represents $C_1$-$C_6$-alkyl which is optionally mono- to trisubstituted by fluorine or chlorine or represents phenyl or benzyl, each of which is optionally mono- to disubstituted by fluorine, chlorine, bromine, $C_1$-$C_4$-alkyl, $C_1$-$C_4$-alkoxy, $C_1$-$C_2$-haloalkoxy, $C_1$-$C_2$-haloalkyl, cyano or nitro, $R^4$ and $R^5$ independently of one another represent $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio or $C_3$-$C_4$-alkenylthio, each of which is optionally mono- to trisubstituted by fluorine or chlorine, or represent phenyl, phenoxy or phenylthio, each of which is optionally mono- to disubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl or $C_1$-$C_3$-haloalkyl, and $R^6$ and $R^7$ independently of one another represent hydrogen, represent $C_1$-$C_6$-alkyl, $C_3$-$C_6$-cycloalkyl, $C_1$-$C_6$-alkoxy, $C_3$-$C_6$-alkenyl or $C_1$-$C_6$-alkoxy-$C_2$-$C_6$-alkyl, each of which is optionally mono- to trisubstituted by fluorine or chlorine, represent phenyl or benzyl, each of which is optionally mono- to trisubstituted by fluorine, chlorine, bromine, $C_1$-$C_5$-haloalkyl, $C_1$-$C_5$-alkyl or $C_1$-$C_5$-alkoxy, or together represent an optionally $C_1$-$C_4$-alkyl-substituted $C_3$-$C_6$-alkylene radical in which optionally one methylene group is replaced by oxygen or sulfur.

4. The compound of the formula (I) as claimed in claim 1 in which

W represents hydrogen, chlorine, bromine, iodine methyl, ethyl, methoxy, ethoxy or trifluoromethyl, X represents chlorine, bromine, iodine, methyl, ethyl, propyl, methoxy, ethoxy, propoxy, methoxyethoxy, ethoxyethoxy, trifluoromethyl, difluoromethoxy, trifluoromethoxy or cyano, Y in the 4-position represents hydrogen, chlorine, bromine, iodine, trifluoromethyl or trifluoromethoxy, Z represents hydrogen; or W represents hydrogen, chlorine, bromine, methyl or ethyl, X represents chlorine, bromine, methyl, ethyl, propyl, methoxy, trifluoromethyl, difluoromethoxy or cyano, Y in the 4-position represents vinyl, ethynyl, propynyl or represents the radical

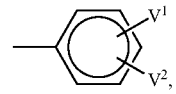

Z represents hydrogen,
$V^1$ represents fluorine, chlorine, methyl, methoxy, trifluoromethyl or trifluoromethoxy,
$V^2$ represents hydrogen, fluorine, chlorine, methyl, methoxy or trifluoromethyl; or W represents hydrogen, chlorine or methyl, X represents chlorine, methyl or trifluoromethyl, Y likewise very particularly preferably in the 5-position represents vinyl, ethynyl, propynyl or represents the radical

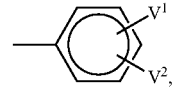

Z in the 4-position represents hydrogen or methyl,
$V^1$ represents fluorine, chlorine, methyl, methoxy, trifluoromethyl or trifluoromethoxy,
$V^2$ represents hydrogen, fluorine, chlorine, methyl, methoxy or trifluoromethyl; or W represents hydrogen, methyl, ethyl, methoxy, ethoxy, chlorine, bromine or iodine, X represents chlorine, bromine, iodine, methyl, ethyl, propyl, methoxy, ethoxy, propoxy, methoxy-ethoxy, ethoxy-ethoxy, trifluoromethyl, difluoromethoxy, trifluoromethoxy or cyano, Y in the 4-position represents methyl or ethyl, Z represents hydrogen; or W represents hydrogen, chlorine, bromine, iodine, methyl or ethyl, X represents chlorine, bromine, iodine, methyl, ethyl, methoxy, trifluoromethyl, difluoromethoxy or trifluoromethoxy, Y in the 4-position represents hydrogen, chlorine, bromine, iodine, methyl or ethyl, Z in the 3- or 5-position represents fluorine, chlorine, bromine, iodine, methyl, ethyl, trifluoromethyl or trifluoromethoxy; and A represents —$CH_2$—, —$CHCH_3$—, —$CH_2$—$CH_2$—, —$CH_2$—$CHCH_3$—, $CH_2$—$CH_2$—$CH_2$—, B represents hydrogen, methyl, ethyl, propyl, isopropyl, butyl, isobutyl, $C_2$-$C_4$-alkenyl, methoxy, ethoxy, propoxy, isopropoxy, butoxy, isobutoxy, methoxy-ethoxy, ethoxy-ethoxy, represents phenyl which is optionally mono- or disubstituted by fluorine, chlorine, bromine, methyl, methoxy, trifluoromethyl, trifluoromethoxy, cyano or nitro, represents cyclopropyl, represents cyclopentyl or cyclohexyl in which optionally one methylene group is replaced by oxygen, or A represents a bond and B represents hydrogen, D represents NH or oxygen, $Q^1$ represents hydrogen, methyl or ethyl, $Q^2$ represents hydrogen, methyl or ethyl, $Q^1$ and $Q^2$ together with the carbon atom to which they are attached represent cyclopropyl, cyclopentyl or cyclohexyl, or $Q^1$ and $Q^2$ together with the carbon atoms to which they are attached represent a $C_5$-$C_6$-ring which is optionally interrupted by oxygen, G represents hydrogen (a) or represents one of the groups

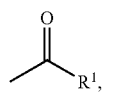
(b)

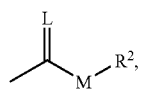
(c)

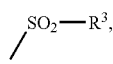
(d)

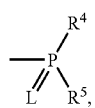
(e)

E or (f)

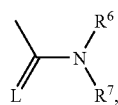
(g)

in which

E represents a metal ion or an ammonium ion,

L represents oxygen or sulfur and

M represents oxygen or sulfur, $R^1$ represents $C_1$-$C_{10}$-alkyl, $C_2$-$C_{10}$-alkenyl, $C_1$-$C_4$-alkoxy-$C_1$-$C_2$-alkyl, $C_1$-$C_4$-alkylthio-$C_1$-$C_2$-alkyl, each of which is optionally mono- to trisubstituted by fluorine or chlorine, or represents $C_3$-$C_6$-cycloalkyl which is optionally monosubstituted by fluorine, chlorine, methyl, ethyl or methoxy, or represents phenyl which is optionally mono- to disubstituted by fluorine, chlorine, bromine, cyano, nitro, methyl, ethyl, n-propyl, isopropyl, methoxy, ethoxy, trifluoromethyl or trifluoromethoxy, or represents furanyl, thienyl or pyridyl, each of which is optionally monosubstituted by chlorine, bromine or methyl, $R^2$ represents $C_1$-$C_{10}$-alkyl, $C_2$-$C_{10}$-alkenyl or $C_1$-$C_4$-alkoxy-$C_2$-$C_4$-alkyl, each of which is optionally mono- to trisubstituted by fluorine or chlorine, or represents cyclopentyl or cyclohexyl or represents phenyl or benzyl, each of which is optionally mono- to disubstituted by fluorine, chlorine, cyano, nitro, methyl, ethyl, methoxy, trifluoromethyl or trifluoromethoxy, $R^3$ represents methyl, ethyl, propyl or isopropyl, each of which is optionally mono- to trisubstituted by fluorine or chlorine, or represents phenyl which is optionally monosubstituted by fluorine, chlorine, bromine, methyl, ethyl, isopropyl, tert-butyl, methoxy, ethoxy, isopropoxy, trifluoromethyl, trifluoromethoxy, cyano or nitro, $R^4$ and $R^5$ independently of one another represent $C_1$-$C_4$-alkoxy or $C_1$-$C_4$-alkylthio or represent phenyl, phenoxy or phenylthio, each of which is optionally monosubstituted by fluorine, chlorine, bromine, nitro, cyano, methyl, methoxy, trifluoromethyl or trifluoromethoxy, and $R^6$ and $R^7$ independently of one another represent hydrogen, represent $C_1$-$C_4$-alkyl, $C_3$-$C_6$-cycloalkyl, $C_1$-$C_4$-alkoxy, $C_3$-$C_4$-alkenyl or $C_1$-$C_4$-alkoxy-$C_2$-$C_4$-alkyl, represent phenyl which is optionally mono- to disubstituted by fluorine, chlorine, bromine, methyl, methoxy or trifluoromethyl, or together represent a $C_5$-$C_6$-alkylene radical in which optionally one methylene group is replaced by oxygen or sulfur.

5. The compound of the formula (I) as claimed in claim 1 wherein

W represents methyl, ethyl or methoxy,

X represents chlorine, methyl, ethyl or methoxy,

Y in the 4-position represents chlorine or bromine,

Z represents hydrogen; or

W represents hydrogen,

X represents methyl,

Y in the 5-position represents the radical

Z in the 4-position represents hydrogen; or

W represents methyl or ethyl,

X represents chlorine, bromine or methyl,

Y in the 4-position represents methyl,

Z represents hydrogen; and

A represents —$CH_2$— or —$CH_2$—$CH_2$—,

B represents hydrogen, methyl, ethyl, propyl, methoxy or cyclopropyl, or A represents a bond and B represents hydrogen, D represents NH, $Q^1$ represents hydrogen, $Q^2$ represents hydrogen, G represents hydrogen (a) or represents one of the groups

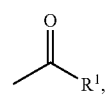
(b)

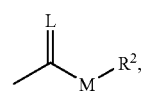
(c)

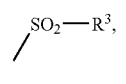
(d)

E, or (f)

-continued

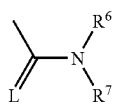
(g)

in which

E represents a metal ion, wherein

L represents oxygen and oxygen,

M represents oxygen.oxygen, $R^1$ represents $C_1$-$C_{10}$-alkyl, represents or phenyl which is optionally monosubstituted by chlorine, $R^2$ represents $C_1$-$C_{10}$-alkyl or $C_2$-$C_{10}$-alkenyl, $R^3$ represents methyl, and $R^6$ and $R^7$ together represent a $C_5$-$C_6$-alkylene radical in which optionally one methylene group is replaced by oxygen.

6. A process for preparing compounds of the formula (I) as claimed in claim 1, characterized in that to obtain (A) compounds of the formula (I-1-a)

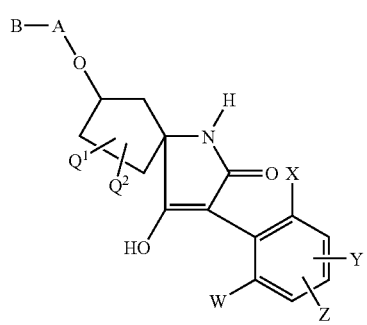
(I-1-a)

in which

A, B, $Q^1$, $Q^2$, W, X, Y and Z are as defined above, compounds of the formula (II)

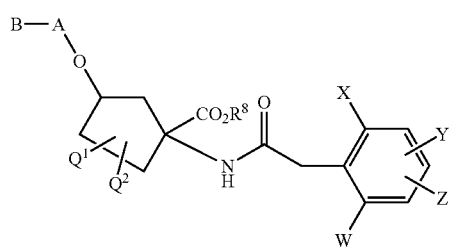
(II)

in which

A, B, $Q^1$, $Q^2$, W, X, Y and Z are as defined above, and $R^8$ represents alkyl, are condensed intramolecularly in the presence of a diluent and in the presence of a base, (B) compounds of the formula (I-2-a)

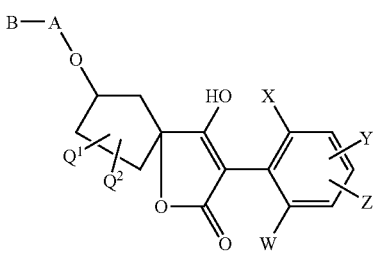
(I-2-a)

in which

A, B, $Q^1$, $Q^2$, W, X, Y and Z are as defined above, compounds of the formula (III)

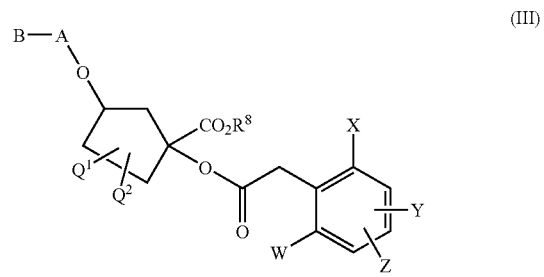
(III)

in which

A, B, $Q^1$, $Q^2$, W, X, Y, Z and $R^8$ are as defined above, are condensed intramolecularly in the presence of a diluent and in the presence of a base, (C) compounds of the formula (I-1-b) to (I-2-b) shown above in which $R^1$, A, B, $Q^1$, $Q^2$, W, X, Y and Z are as defined above, compounds of the formula (I-1-a) to (I-2-a) shown above in which A, B, $Q^1$, $Q^2$, W, X, Y and Z are as defined above are in each case reacted α) with compounds of the formula (IV)

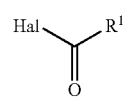
(IV)

in which $R^1$ is as defined above and

Hal represents halogen or

β) with carboxylic anhydrides of the formula (V)

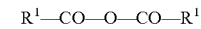

$R^1$—CO—O—CO—$R^1$ (V)

in which $R^1$ is as defined above, if appropriate in the presence of a diluent and if appropriate in the presence of an acid binder, (D) compounds of the formula (I-1-c) to (I-2-c) shown above in which $R^2$, A, B, $Q^1$, $Q^2$, W, M, X, Y and Z are as defined above and L represents oxygen, compounds of the formula (I-1-a) to (I-2-a) shown above in which A, B, $Q^1$, $Q^2$, W, X, Y and Z are as defined above are in each case reacted with chloroformic esters or chloroformic thioesters of the formula (VI)

 (VI)

in which
R² and M are as defined above,
if appropriate in the presence of a diluent and if appropriate in the presence of an acid binder,
(E) compounds of the formulae (I-1-c) to (I-2-c) shown above in which R², A, B, Q¹, Q², W, M, X, Y and Z are as defined above and L represents sulfur, compounds of the formulae (I-1-a) to (I-2-a) shown above in which A, B, Q¹, Q², W, X, Y and Z are as defined above are in each case
reacted with chloromonothioformic esters or chlorodithioformic esters of the formula (VII)

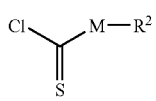 (VII)

in which
M and R² are as defined above,
if appropriate in the presence of a diluent and if appropriate in the presence of an acid binder,
(F) compounds of the formulae (I-1-d) to (I-2-d) shown above in which R³, A, B, W, Q¹, Q², X, Y and Z are as defined above, compounds of the formulae (I-1-a) to (I-2-a) shown above in which A, B, Q¹, Q², W, X, Y and Z are as defined above are in each case
reacted with sulfonyl chlorides of the formula (VIII)

 (VIII)

in which
R³ is as defined above,
if appropriate in the presence of a diluent and if appropriate in the presence of an acid binder,
(G) compounds of the formulae (I-1-e) to (I-2-e) shown above in which L, R⁴, R⁵, A, B, Q¹, Q², W, X, Y and Z are as defined above, compounds of the formulae (I-1-a) to (I-2-a) shown above in which A, B, Q¹, Q², W, X, Y and Z are as defined above are in each case
reacted with phosphorus compounds of the formula (IX)

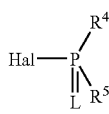 (IX)

in which
L, R⁴ and R⁵ are as defined above and
Hal represents halogen,
if appropriate in the presence of a diluent and if appropriate in the presence of an acid binder,
(H) compounds of the formulae (I-1-f) to (I-2-f) shown above in which E, A, B, Q¹, Q², W, X, Y and Z are as defined above, compounds of the formulae (I-1-a) to (I-2-a) shown above in which A, B, Q¹, Q², W, X, Y and Z are as defined above are in each case reacted with metal compounds or amines of the formulae (X) and (XI), respectively

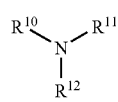 (XI)

in which
Me represents a mono- or divalent metal,
t represents the number 1 or 2 and
R¹⁰, R¹¹, R¹² independently of one another represent hydrogen or alkyl,
if appropriate in the presence of a diluent,
(I) compounds of the formulae (I-1-g) to (I-2-g) shown above in which L, R⁶, R⁷, A, B, Q¹, Q², W, X, Y and Z are as defined above, compounds of the formulae (I-1-a) to (I-2-a) shown above in which A, B, Q¹, Q², W, X, Y and Z are as defined above are in each case
α) reacted with isocyanates or isothiocyanates of the formula (XII)

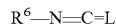 (XII)

in which
R⁶ and L are as defined above,
if appropriate in the presence of a diluent and if appropriate in the presence of a catalyst, or
β) reacted with carbamoyl chlorides or thiocarbamoyl chlorides of the formula (XIII)

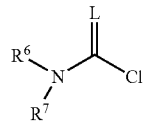 (XIII)

in which
L, R⁶ and R⁷ are as defined above,
if appropriate in the presence of a diluent and if appropriate in the presence of an acid binder.

7. A composition comprising an effective amount of an active compound combination comprising, as components,
(a') at least one compound of the formula (I) as claimed in claim 1, and
(b') at least one crop plant compatibility-improving compound selected from the group consisting of:
4-dichloroacetyl-1-oxa-4-azaspiro[4.5]decane, AD-67, MON-4660, 1-dichloroacetylhexahydro-3,3,8a-trimethylpyrrolo[1,2-a]pyrimidin-6(2H)-one, dicyclonon, BAS-145138, 4-dichloroacetyl-3,4-dihydro-3-methyl-2H-1,4-benzoxazine, benoxacor, 1-methylhexyl 5-chloroquinoline-8-oxyacetate, cloquintocet-mexyl, 3-(2-chlorobenzyl)-1-(1-methyl-1-phenylethyl)urea, cumyluron, α-(cyanomethoximino)phenylacetonitrile, cyometrinil, 2,4-dichlorophenoxyacetic acid (2,4-D), 4-(2,4-dichlorophenoxy)butyric acid, 2,4-DB, 1-(1-methyl-1-phenylethyl)-3-(4-methylphenyl)urea, daimuron, dymron, 3,6-dichloro-2-methoxybenzoic acid, dicamba, S-1-methyl-1-phenylethyl piperidine-1-thiocarboxylate, dimepiperate 2,2-dichloro-N-(2-oxo-2-(2-propenylamino)ethyl)-N-(2-propenyl)acetamide, DKA-24, 2,2-dichloro-N,N-di-2-propenylacetamide, dichlormid, 4,6-dichloro-2-phenylpyrimidine, fenclorim, ethyl 1-(2,4-dichlorophenyl)-5-trichloromethyl-1H-1,2,4-triazole-3-carboxylate, fenchlorazole-ethyl, phenylmethyl 2-chloro-4-trifluoromethylthiazole-5-carboxylate, flurazole, 4-chloro-N-(1,3-dioxolan-2-ylmethoxy)-α-trifluoroacetophenone oxime, fluxofenim, 3-dichloroacetyl-5-(2-furanyl)-2,2-dimethyloxazolidine, furilazole, MON-13900, ethyl 4,5-dihydro-5,5-diphenyl-3-isoxazolecarboxylate, isoxadifen-ethyl, 1-(ethoxycarbonyl)ethyl 3,6-dichloro-2-methoxybenzoate lactidichlor, (4-chloro-o-tolyloxy)acetic acid, MCPA, 2-(4-chloro-o-tolyloxy)propionic acid, mecoprop, diethyl 1-(2,4-dichorophenyl)-4,5-dihydro-5-methyl-1H-pyrazole-3,5-dicarboxylate, mefenpyr-diethyl, 2-dichloromethyl-2-methyl-1,3-dioxolane, MG-191, 2-propenyl-1-oxa-4-azaspiro[4.5]decane-4-carbodithioate, MG-838, 1,8-naphthalic anhydride, α-(1,3-dioxolan-2-ylmethoximino) phenylacetonitrile, oxabetrinil, 2,2-dichloro-N-(1,3-dioxolan-2-ylmethyl)-N-(2-propenyl)acetamide, PPG-1292, 3-dichloroacetyl-2,2-dimethyloxazolidine, R-28725, 3-dichloroacetyl-2,2,5-trimethyloxazolidine, R-29148, 4-(4-chloro-o-tolyl)butyric acid, 4-(4-chlorophenoxy)butyric acid, diphenylmethoxyacetic acid, methyl diphenylmethoxyacetate, ethyl diphenylmethoxyacetate, methyl 1-(2-chlorophenyl)-5-phenyl-1H-pyrazole-3-carboxylate, ethyl 1-(2,4-dichlorophenyl)-5-methyl-1H-pyrazole-3-carboxylate, ethyl 1-(2,4-dichlorophenyl)-5-isopropyl-1H-pyrazole-3-carboxylate, ethyl 1-(2,4-dichlorophenyl)-5-(1,1-dimethyl-ethyl)-1H-pyrazole-3-carboxylate, ethyl 1-(2,4-dichlorophenyl)-5-phenyl-1H-pyrazole-3-carboxylate, ethyl 5-(2,4-dichlorobenzyl)-2-isoxazoline-3-carboxylate, ethyl 5-phenyl-2-isoxazoline-3-carboxylate, ethyl 5-(4-fluorophenyl)-5-phenyl-2-isoxazoline-3-carboxylate, 1,3-dimethylbut-1-yl 5-chloroquinoline-8-oxyacetate, 4-allyloxybutyl 5-chloro-quinoline-8-oxyacetate, 1-allyloxyprop-2-yl 5-chloroquinoline-8-oxyacetate, methyl 5-chloroquinoxaline-8-oxyacetate, ethyl 5-chloroquinoline-8-oxyacetate, allyl 5-chloroquinoxaline-8-oxyacetate, 2-oxoprop-1-yl 5-chloroquinoline-8-oxyacetate, diethyl 5-chloroquinoline-8-oxymalonate, diallyl 5-chloroquinoxaline-8-oxymalonate, diethyl 5-chloroquinoline-8-oxymalonate, 4-carboxychroman-4-ylacetic acid, AC-304415, 4-chlorophenoxyacetic acid, 3,3'-dimethyl-4-methoxybenzophenone, 1-bromo-4-chloromethylsulfonylbenzene, 1-[4-(N-2-methoxybenzoyl-sulfamoyl)phenyl]-3-methylurea N-(2-methoxybenzoyl)-4-[(methylaminocarbonyl)amino]benzenesulfonamide), 1-[4-(N-2-methoxybenzoylsulfamoyl)phenyl]-3,3-dimethylurea, 1-[4-(N-4,5-dimethylbenzoyl-sulfamoyl)phenyl]-3-methylurea, and 1-[4-(N-naphthylsulfamoyl)phenyl]-3,3-dimethylurea, N-(2-methoxy-5-methylbenzoyl)-4-(cyclopropylaminocarbonyl)benzenesulfonamide, and/or one of the following compounds, defined by general formulae of the general formula (IIa)

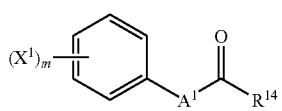

or of the general formula (IIb)

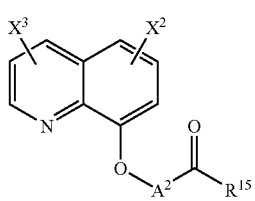

or of the formula (IIc)

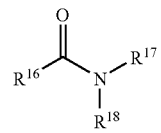

where
m represents a number 0, 1, 2, 3, 4 or 5,
$A^1$ represents one of the divalent heterocyclic groupings shown below

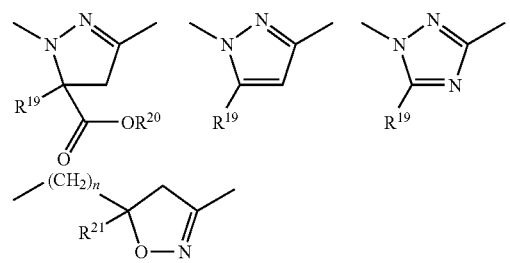

n represents a number 0, 1, 2, 3, 4 or 5,
$A^2$ represents optionally $C_1$-$C_4$-alkyl- and/or $C_1$-$C_4$-alkoxy-carbonyl- and/or $C_1$-$C_4$-alkenyloxycarbonyl-substituted alkanediyl having 1 or 2 carbon atoms,
$R^{14}$ represents hydroxyl, mercapto, amino, $C_1$-$C_6$-alkoxy, $C_1$-$C_6$-alkylthio, $C_1$-$C_6$-alkylamino or di($C_1$-$C_4$-alkyl) amino,
$R^{15}$ represents hydroxyl, mercapto, amino, $C_1$-$C_7$-alkoxy, $C_1$-$C_6$-alkenyloxy, $C_1$-$C_6$-alkenyloxy-$C_1$-$C_6$-alkoxy, $C_1$-$C_6$-alkylthio, $C_1$-$C_6$-alkylamino or di($C_1$-$C_4$-alkyl)-amino,
$R^{16}$ represents optionally fluorine-, chlorine- and/or bromine-substituted $C_1$-$C_4$-alkyl,
$R^{17}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl,
$R^{18}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, $R^{17}$ and $R^{18}$ also together represent $C_3$-$C_6$-alkanediyl or $C_2$-$C_5$-oxaalkanediyl, each of which is optionally substituted by $C_1$-$C_4$-alkyl, phenyl, furyl, a fused benzene ring or by two substituents which, together with the C atom to which they are attached, form a 5- or 6-membered carbocycle,
$R^{19}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl,
$R^{20}$ represents hydrogen, in each case optionally hydroxyl-, cyano-, halogen- or $C_1$-$C_4$-alkoxy-substituted $C_1$-$C_6$-alkyl, $C_3$-$C_6$-cycloalkyl or tri-($C_1$-$C_4$-alkyl)silyl, $R^{21}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $X^1$ represents nitro, cyano, halogen, $C_1$-$C_4$-alkyl, $C_1$-$C_4$-haloalkyl, $C_1$-$C_4$-alkoxy or $C_1$-$C_4$-haloalkoxy, $X^2$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, $X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, and/or the following compounds, defined by general formulae of the general formula (IId)

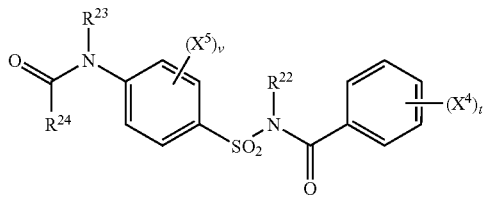

(IId)

or of the general formula (IIe)

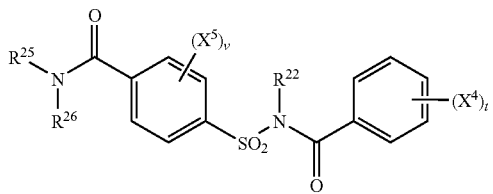

(IIe)

where t represents a number 0, 1, 2, 3, 4 or 5, v represents a number 0, 1, 2, 3, 4 or 5, $R^{22}$ represents hydrogen or $C_1$-$C_4$-alkyl, $R^{23}$ represents hydrogen or $C_1$-$C_4$-alkyl, $R^{24}$ represents hydrogen, in each case optionally cyano-, halogen- or $C_1$-$C_4$-alkoxy-substituted $C_1$-$C_6$-alkyl, $C_1$-$C_6$-alkoxy, $C_1$-$C_6$-alkylthio, $C_1$-$C_6$-alkylamino or di($C_1$-$C_4$-alkyl)amino, or in each case optionally cyano-, halogen- or $C_1$-$C_4$-alkyl-substituted $C_3$-$C_6$-cycloalkyl, $C_3$-$C_6$-cycloalkyloxy, $C_3$-$C_6$-cycloalkylthio or $C_3$-$C_6$-cycloalkylamino, $R^{25}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, or optionally cyano-, halogen- or $C_1$-$C_4$-alkyl-substituted $C_3$-$C_6$-cycloalkyl, $R^{26}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, optionally cyano-, halogen- or $C_1$-$C_4$-alkyl-substituted $C_3$-$C_6$-cycloalkyl, or optionally nitro-, cyano-, halogen-, $C_1$-$C_4$-alkyl-, $C_1$-$C_4$-halo-alkyl-, $C_1$-$C_4$-alkoxy- or $C_1$-$C_4$-haloalkoxy-substituted phenyl, or together with $R^{25}$ represents in each case optionally $C_1$-$C_4$-alkyl-substituted $C_2$-$C_6$-alkanediyl or $C_2$-$C_5$-oxaalkanediyl, $X^4$ represents nitro, cyano, carboxyl, carbamoyl, formyl, sulfamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy, and $X^5$ represents nitro, cyano, carboxyl, carbamoyl, formyl, sulfamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy.

8. The composition as claimed in claim 7, wherein the crop plant compatibility-improving compound is selected from the group consisting of:

cloquintocet-mexyl, fenchlorazole-ethyl, isoxadifen-ethyl, mefenpyr-diethyl, furilazole, fenclorim, cumyluron, dymron,

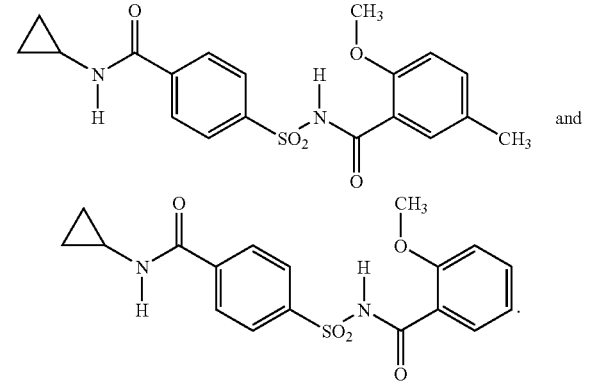

and

.

9. The composition as claimed in claim 7, wherein the crop plant compatibility-improving compound is cloquintocet-mexyl.

10. The composition as claimed in claim 7, wherein the crop plant compatibility-improving compound is mefenpyr-diethyl.

11. A composition comprising at least one compound of the formula (I) as claimed in claim 1 and at least one salt of the formula (III')

$$\left[ \begin{array}{c} R^{26} \\ R^{29}-D^{+}-R^{27} \\ R^{28} \end{array} \right]_n R^{30\,n-} \qquad (III')$$

in which

D represents nitrogen or phosphorus, $R^{26}$, $R^{27}$, $R^{28}$ and $R^{29}$ independently of one another represent hydrogen or in each case optionally substituted $C_1$-$C_8$-alkyl or mono- or polyunsaturated, optionally substituted $C_1$-$C_8$-alkylene, the substituents being selectable from halogen, nitro and cyano, n represents 1, 2, 3 or 4, $R^{30}$ represents an organic or inorganic anion.

12. The composition as claimed in claim 11, further comprising at least one penetrant.

13. A pesticide and/or a herbicide and/or a fungicide formulation, comprising at least one compound of formula (I) as claimed in claim 1.

14. A method for controlling fungi, comprising allowing a compound of formula (I) as claimed in claim 1 to act on a habitat thereof.

15. A compound of formula (I) as claimed in claim 1 that is used to control insects or arachnoids, and/or unwanted vegetation, and/or fungi.

16. A process for preparing pesticides and/or herbicides and/or fungicides, comprising mixing a compound of formula (I) as claimed in claim 1 with an extender and/or surfactant.

17. A method for controlling unwanted vegetation, comprising allowing a composition as claimed in claim 7 to act on a plant and/or habitat thereof.

18. A composition as claimed in claim 7 that is used for controlling unwanted vegetation.

19. A method for controlling unwanted vegetation, comprising allowing a compound of the formula (I) as claimed in claim 1 and a crop plant compatibility improving compound to act, separately in close temporal succession, on a plant and/or surroundings thereof.

20. A method for improving the activity of pesticides and/or herbicides comprising an active compound of the formula (I) as claimed in claim 1 comprising utilizing said compound in a ready-to-use composition spray liquor.

21. The method as claimed in claim 20, wherein the spray liquor is prepared using a penetrant.

22. The compound of the formula (I) as claimed in claim 1 wherein
W represents methyl or ethyl,
X represents chlorine, bromine, or methyl,
Y in the 4-position represents methyl,
Z represents hydrogen,
A represents —CH$_2$— or —CH$_2$—CH$_2$—,
B represents hydrogen, methyl, ethyl, propyl, methoxy or cyclopropyl,
   or A represents a bond and B represents hydrogen,
D represents NH,
Q$^1$ represents hydrogen,
Q$^2$ represents hydrogen,

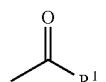
(b)

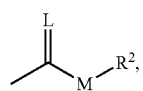
(c)

G represents hydrogen (a),
wherein
   L represents oxygen,
   M represents oxygen, R$^1$ represents C$_1$-C$_{10}$-alkyl or phenyl which is optionally monosubstituted by chlorine, and
R$^2$ represents C$_1$-C$_{10}$-alkyl or C$_2$-C$_{10}$-alkenyl.

23. The compound of the formula (I) as claimed in claim 1 wherein the compound is selected from the group consisting of:

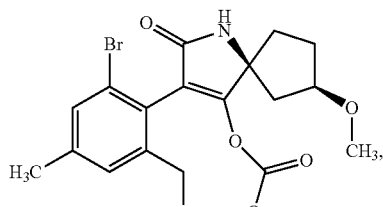

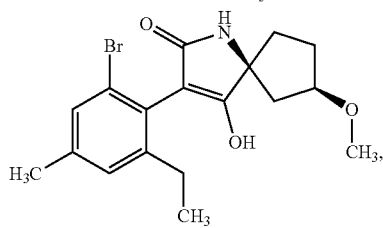

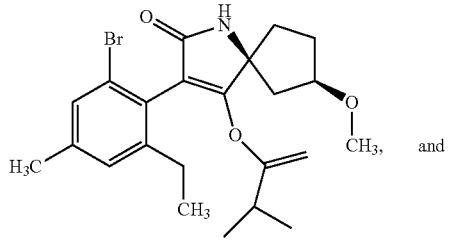 and

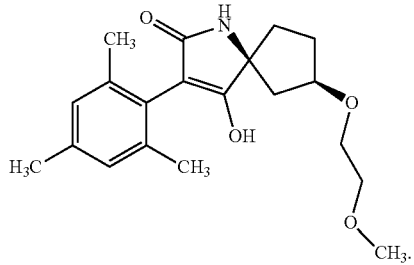

* * * * *